United States Patent
Yamaji

(10) Patent No.: US 10,201,316 B2
(45) Date of Patent: Feb. 12, 2019

(54) METHOD AND APPARATUS FOR DISPLAYING STATES

(71) Applicant: FUJITSU LIMITED, Kawasaki-shi, Kanagawa (JP)

(72) Inventor: Takayuki Yamaji, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/499,086

(22) Filed: Apr. 27, 2017

(65) Prior Publication Data

US 2017/0251986 A1 Sep. 7, 2017

Related U.S. Application Data

(63) Continuation of application No. PCT/JP2014/079056, filed on Oct. 31, 2014.

(51) Int. Cl.
*A61B 5/00* (2006.01)
*G06F 3/0485* (2013.01)
(Continued)

(52) U.S. Cl.
CPC .......... *A61B 5/743* (2013.01); *A61B 5/0205* (2013.01); *A61B 5/02055* (2013.01); *A61B 5/1118* (2013.01); *A61B 5/4806* (2013.01); *A61B 5/4812* (2013.01); *A61B 5/4815* (2013.01); *A61B 5/744* (2013.01); *G06F 3/0485* (2013.01);
(Continued)

(58) Field of Classification Search
CPC ............. A61B 5/4806–5/4818; G06F 3/0485
See application file for complete search history.

(56) References Cited

U.S. PATENT DOCUMENTS

2003/0128212 A1 7/2003 Pitkow
2006/0060198 A1* 3/2006 Aylsworth ........... A61B 5/0205
128/204.23
(Continued)

FOREIGN PATENT DOCUMENTS

JP 61-12764 U 1/1986
JP 7-56961 A 3/1995
(Continued)

OTHER PUBLICATIONS

International Search Report dated Jan. 27, 2015 in PCT/JP2014/079056, filed on Oct. 31, 2014.
(Continued)

*Primary Examiner* — Phong X Nguyen
(74) *Attorney, Agent, or Firm* — Oblon, McClelland, Maier & Neustadt, L.L.P.

(57) ABSTRACT

A disclosed state display method includes: obtaining measurement results of vital activities of a subject; and displaying temporal transition of states of the subject by a one-dimensional heat map based on the measurement results. And the displaying includes: first displaying, in association with a first period in which the measurement results represent a sleep state, a first color that represents a depth of sleep by shading and has a first hue corresponding to the sleep state; and second displaying, in association with a second period in which the measurement results represent a non-sleep state, a second color that represents an intensity of an activity by the shading and has a second hue corresponding to the non-sleep state.

6 Claims, 46 Drawing Sheets

(51) Int. Cl.
    *A61B 5/11*     (2006.01)
    *G06T 11/00*    (2006.01)
    *A61B 5/0205*   (2006.01)
    *G06T 11/20*    (2006.01)
    *G06F 3/0488*   (2013.01)

(52) U.S. Cl.
    CPC ........ *G06F 3/04883* (2013.01); *G06T 11/001* (2013.01); *G06T 11/206* (2013.01); *A61B 5/1116* (2013.01); *A61B 2560/0242* (2013.01)

(56) References Cited

U.S. PATENT DOCUMENTS

| | | | | |
|---|---|---|---|---|
| 2006/0235639 | A1* | 10/2006 | Piazza | G01K 7/42 |
| | | | | 702/130 |
| 2010/0167712 | A1* | 7/2010 | Stallings | G06F 3/0485 |
| | | | | 455/418 |
| 2011/0015495 | A1 | 1/2011 | Dothie et al. | |
| 2011/0224510 | A1* | 9/2011 | Oakhill | G16H 50/30 |
| | | | | 600/301 |
| 2012/0253485 | A1* | 10/2012 | Weast | G06F 1/163 |
| | | | | 700/91 |
| 2012/0317167 | A1* | 12/2012 | Rahman | A61B 5/1118 |
| | | | | 709/202 |
| 2013/0310662 | A1 | 11/2013 | Tsutsumi et al. | |
| 2013/0310712 | A1* | 11/2013 | Kanemitsu | A61B 5/11 |
| | | | | 600/595 |
| 2014/0039840 | A1* | 2/2014 | Yuen | A61B 5/6838 |
| | | | | 702/189 |
| 2014/0276245 | A1 | 9/2014 | Tsutsumi et al. | |
| 2015/0190072 | A1* | 7/2015 | Armstrong | G06F 19/3481 |
| | | | | 600/301 |
| 2015/0339792 | A1* | 11/2015 | Emori | G06Q 50/22 |
| | | | | 705/2 |

FOREIGN PATENT DOCUMENTS

| | | |
|---|---|---|
| JP | 9-244618 A | 9/1997 |
| JP | 2003-216298 A | 7/2003 |
| JP | 2010-148829 | 7/2010 |
| JP | 2011-36649 | 2/2011 |
| JP | 2012-187299 A | 10/2012 |
| JP | 2012-235920 | 12/2012 |
| JP | 2013-45336 | 3/2013 |
| WO | WO 2014/133146 A1 | 9/2014 |

OTHER PUBLICATIONS

Written Opinion dated Jan. 27, 2015 in PCT/JP2014/079056, filed on Oct. 31, 2014 (with English Translation).
Office Action dated May 9, 2018, in co-pending U.S. Appl. No. 15/499,183, 17 pages.
International Search Report dated Jan. 27, 2015 in PCT/JP2014/079055, 1 page.
Office Action issued in corresponding U.S. Appl. No. 15/499,183, dated Sep. 28, 2018.

\* cited by examiner

| MEASUREMENT DATE | MEASUREMENT TIME ZONE | LEVEL OF DEPTH OF SLEEP (P) |
|---|---|---|
| ⋮ | ⋮ | ⋮ |
| January 4 | 05:00 - 05:02 | 7 |
| January 4 | 05:02 - 05:04 | 7 |
| January 4 | 05:04 - 05:06 | 6 |
| January 4 | 05:06 - 05:08 | 6 |
| January 4 | 05:08 - 05:10 | 6 |
| ⋮ | ⋮ | ⋮ |
| January 4 | 09:00 - 09:02 | 0 |
| January 4 | 09:02 - 09:04 | 0 |
| January 4 | 09:04 - 09:06 | 0 |
| January 4 | 09:06 - 09:08 | 0 |
| January 4 | 09:08 - 09:10 | 0 |
| ⋮ | ⋮ | ⋮ |

FIG.6

| MEASUREMENT DATE | MEASUREMENT TIME ZONE | LEVEL OF AMOUNT OF ACTIVITY (Q) |
|---|---|---|
| ⋮ | ⋮ | ⋮ |
| January 4 | 05:00 - 05:02 | 0 |
| January 4 | 05:02 - 05:04 | 0 |
| January 4 | 05:04 - 05:06 | 0 |
| January 4 | 05:06 - 05:08 | 0 |
| January 4 | 05:08 - 05:10 | 0 |
| ⋮ | ⋮ | ⋮ |
| January 4 | 09:00 - 09:02 | 15 |
| January 4 | 09:02 - 09:04 | 15 |
| January 4 | 09:04 - 09:06 | 16 |
| January 4 | 09:06 - 09:08 | 16 |
| January 4 | 09:08 - 09:10 | 16 |
| ⋮ | ⋮ | ⋮ |

FIG.7

METHOD AND APPARATUS FOR DISPLAYING STATES

CROSS-REFERENCE TO RELATED APPLICATIONS

This application is a continuing application, filed under 35 U.S.C. section 111(a), of International Application PCT/JP2014/079056, filed on Oct. 31, 2014, the entire contents of which are incorporated herein by reference.

FIELD

This invention relates to a technique for visualizing states of vital activities.

BACKGROUND

One patent document discloses an example of displaying actions, daily activities, rest and sleep as a band graph in a system for collecting vital data of a user. Moreover, another patent document discloses an example in which sleep and awaking are displayed as a band graph in a sleep state evaluation apparatus. In both cases, the user can distinguish a sleep period and a period other than the sleep period, however, the user cannot know information other than information for each time band and length of the time band.

Moreover, another patent document discloses a band graph representing a sleep depth by shading of colors as a system for evaluating the sleep states. In this example, the user cannot know a relationship between sleep and activities.

Patent Document 1: Japanese Laid-open Patent Publication No. 2012-235920
Patent Document 2: Japanese Laid-open Patent Publication No. 2013-045336
Patent Document 3: Japanese Laid-open Patent Publication No. 2010-148829

Therefore, there is no technique for enabling the user to chronologically grasp a relation between a depth of sleep and an intensity of an activity.

SUMMARY

A state display method of one aspect includes: obtaining measurement results of vital activities of a subject; and displaying temporal transition of states of the subject by a one-dimensional heat map based on the measurement results. And the displaying includes: first displaying, in association with a first period in which the measurement results represent a sleep state, a first color that represents a depth of sleep by shading and has a first hue corresponding to the sleep state; and second displaying, in association with a second period in which the measurement results represent a non-sleep state, a second color that represents an intensity of an activity by the shading and has a second hue corresponding to the non-sleep state.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 6 is a diagram depicting an example of first data;
FIG. 7 is a diagram depicting an example of second data.

DESCRIPTION OF EMBODIMENTS

[Embodiment 1]

Figure 1:
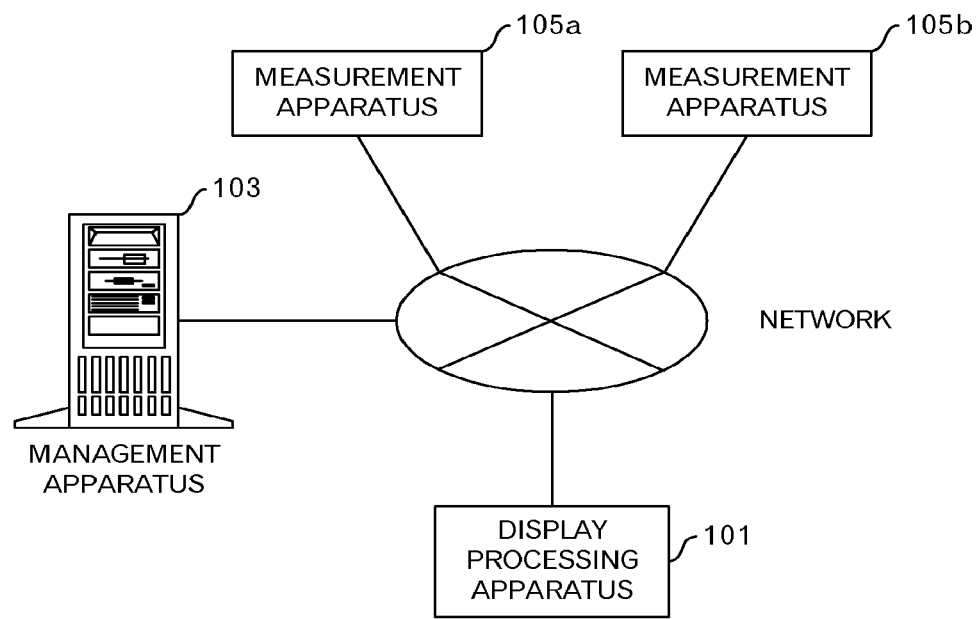
FIG. 1 is a diagram depicting an example of network configuration.

FIG. 1 illustrates an example of network configuration. A display processing apparatus 101 is an apparatus that visualizes a state of a vital activity of a subject. The display processing apparatus 101 has a display device such as a LCD (Liquid Crystal Display), for example. More specifically, the display processing apparatus 101 graphically displays a level of a depth of sleep and a level of an amount of activity. Furthermore, the display processing apparatus 101 displays data for results of analyzing the state of the vital activity. The network is, for example, a mobile communication network, the Internet, a LAN (Local Area Network) or the like.

A measurement apparatus 105a is an apparatus that measures a depth of sleep. The measurement apparatus 105a measures, for example, brain waves, a pulse, a body temperature, body movements, myoelectricity, blood pressure, a breathing rate or the like of a subject. The level of the depth of sleep is determined based on measurement results by the measurement apparatus 105a. The level of the depth of sleep, which is determined in the measurement apparatus 105a, is sent to a management apparatus 103 via a network, and the management apparatus 103 manages the level of the depth of sleep for each subject. Alternatively, measurement results may be sent via a network from the measurement apparatus 105a to the management apparatus 103, and the management apparatus 103 may determine the level of the depth of sleep. Sleep stages may be used, for example, as examples of the level of the depth of sleep.

A measurement apparatus 105b is an apparatus that measures an amount of activity of a subject. For example, when the measurement apparatus 105b is a portable device such as a smartphone or a wearable terminal, the measurement apparatus 105b measures acceleration related to movements of the measurement apparatus 105b itself. Alternatively, when the measurement apparatus 105b is a device that is located on a living environment or a working environment, for example, the measurement apparatus 105b measures a position, a posture, a heart rate and the like of a subject. The measurement apparatus 105b that is set up in this way may also measure the position and the posture of a subject by analyzing captured images or reactions to microwaves emitted by the measurement apparatus 105b. A level of an amount of activity is determined based on measurement results from the measurement apparatus 105b. The level of the amount of activity determined by the measurement apparatus 105b is sent via a network to the management apparatus 103, and the management apparatus 103 manages the level of the amount of activity for each subject. Alternatively, measurement results may be sent via a network from the measurement apparatus 105b to the management apparatus 103, and the management apparatus 103 may determine the level of the amount of activity. METs (Metabolic Equivalents) may also be used as an example of the level of the amount of activity, for example.

Moreover, the level of the amount of activity may also be determined based on measurement results by the measurement apparatus 105a. Furthermore, the level of the depth of sleep may be determined based on measurement results by the measurement apparatus 105b. The measurement apparatus 105a and the measurement apparatus 105b may also be the same apparatus.

The display processing apparatus 101 then obtains data representing the level of the depth of sleep relate to a specific subject (hereafter, referred to as first data) and data representing the level of the amount of activity (hereafter, referred to as second data) from the management apparatus 103 via a network. The first data and the second data represent vital activities measured in a time series.

The display processing apparatus 101 may also obtain first data directly from the measurement apparatus 105a. Similarly, the display processing apparatus 101 may also obtain second data directly from the measurement apparatus 105a. Similarly, the display processing apparatus 101 may also obtain second data directly from the measurement apparatus 105b. Similarly, the display processing apparatus 101 may also obtain first data directly from the measurement apparatus 105b.

The display processing apparatus 101 may also function as the measurement apparatus 105a. The display processing apparatus 101 may also function as the measurement apparatus 105b. The display processing apparatus 101 may also function as the management apparatus 103. When the display processing apparatus 101 itself performs measurement and generates first data and second data, the display processing apparatus 101 may not perform communication via a network.

Figure 2:
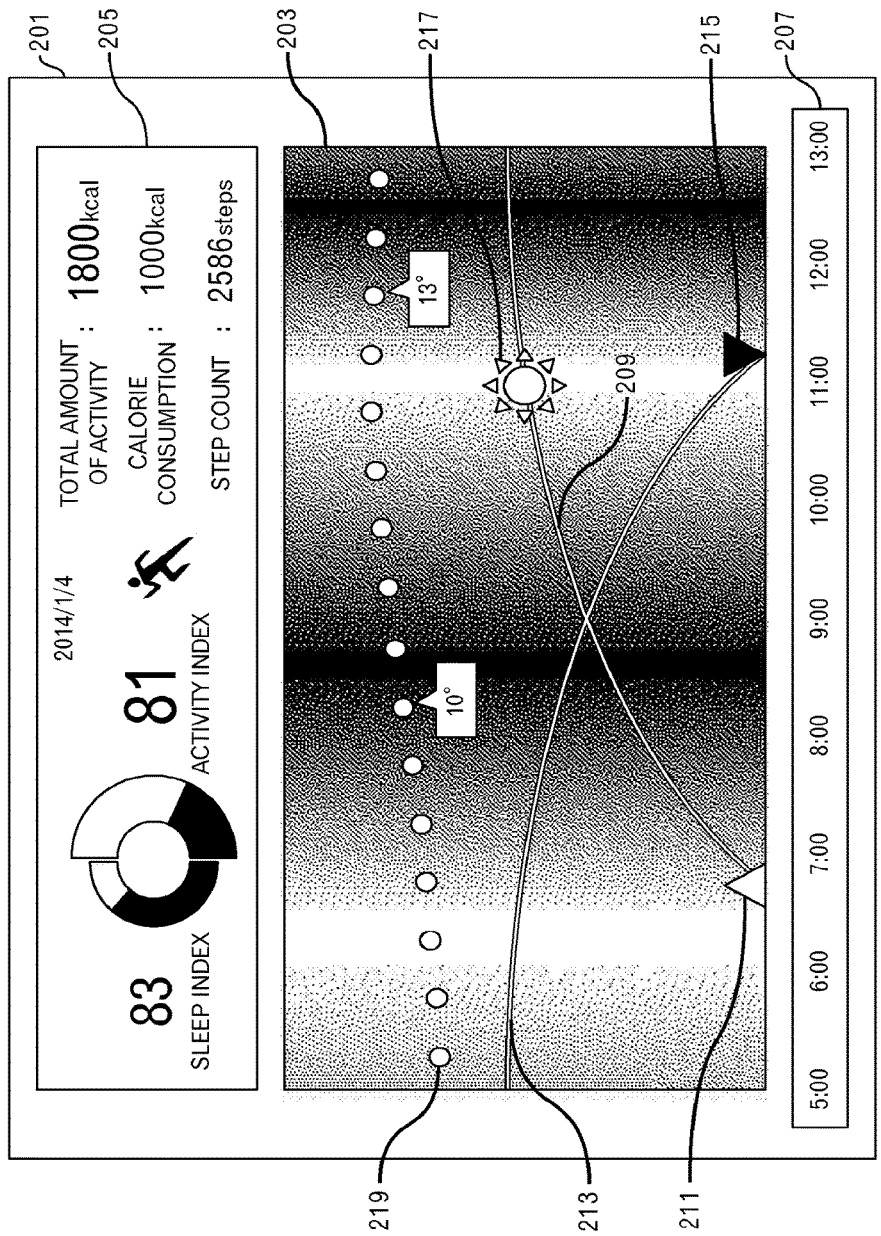
FIG. 2 is a diagram depicting an example of a main screen.

FIG. 2 illustrates an example of a main screen 201. The main screen 201 is a screen on which a state of a vital activity of a subject is visualized. The main screen 201 includes a first area 203, a second area 205 and a third area 207.

A graph image that represents a state of a vital activity of a subject is displayed in the first area 203. The target period for the graph display in an example in FIG. 2 is the period from Jan. 4, 2014 5:00 to 13:00. The time in the center of the target period in the graph display is called a center time. The center time in the example in FIG. 2 is Jan. 4, 2014 9:00.

In the example in FIG. 2, the period from about 6:20 to 13:00 represents a degree of an amount of activity. The area in this period is filled with a color having an "orange" hue. An area of a state where there is a large amount of activity is occupied by the dark color, and an area where there is a small amount of activity is occupied by the light color. In other words, the degree of an amount of activity is represented by a chroma of the color. The relationship between the degree of an amount of activity and the shading of the color is also the same in the following figures.

In the example in FIG. 2, the period from 5:00 to about 6:20 represents a degree of the depth of sleep. The area of this period is filled with a color having a "blue" hue. In an area for a state of deep sleep, the color is dark, and in an area of light sleep, the color is light. In other words, the degree of the depth of sleep is represented by a chroma of the color. The relationship between the degree of the depth of sleep and the shading of the color is also the same in the following figures.

In this way, the degree of a depth of sleep and the degree of an amount of activity in the first area 203 is color-coded into zones. This graph is in a form of a heat map that illustrates in one dimension a temporal transition of states of a subject. It is not necessary to limit an area that represents a degree of an amount of activity as an "orange" hue, and an area that represents a degree of a depth of sleep as a "blue" hue. However, by using different color type for each other, it is possible to easily distinguish between the display for sleep and the display for activity.

In this graph, it is possible to display the sleep state and the active state in a continuous state change in one graph with no breaks. For example, when taking a nap in a time zone in which the state should be the active state, the depth of sleep and the amount of activity before and after the sleep is represented as a continuous graph. Therefore, this is helpful to observe from a viewpoint of an activity condition in which the subject took a nap, a viewpoint of depth of sleep caused by the nap, or a viewpoint of how the subsequent activity condition changed due to the nap.

In the second area 205, an analysis screen is displayed that represents analysis results of the state of the vital activity of a subject. In this analysis screen, there are two kinds of screens: a first analysis screen and a second analysis screen.

When the non-sleep period is dominant in a target period of the graph display, or in other words, when the non-sleep period is longer than the sleep period, data related to an active state of the subject is displayed. The non-sleep period in a target period of the graph display is a period for which it is determined that the subject is in a non-sleep state. The sleep period in a target period of the graph display is a period for which it is determined that the subject is in a sleep state. In this example, in addition to an activity index, each value for a total amount of activity, calorie consumption, and a step count are displayed. This screen that displays these kinds of analysis results related to the active state of the subject is called the second analysis screen. The second analysis screen has a color tone in which a color having an "orange" hue is mainly used. A sleep index for the sleep state of the subject is also displayed.

Graphs for an environment in a target period of the graph display are also displayed over the first area 203. The line 209 represents a height of the sun. The mark 211 represents the time of the sunrise. In the following, this mark 211 will be called the sunrise mark. The line 213 represents the height of the moon. The mark 215 represents the time of the moonset. Hereafter, the mark 215 will be called the moonset mark. Moreover, the sun mark 217 represents that an overlapping line 209 corresponds to the height of the sun.

A mark 219 that represents the temperature is also displayed in the first area 203. The temperature is represented by a position in the vertical direction, which is pointed by the mark. In other words, in the example in the figure, an axis that represents high/low temperature is provided in the vertical direction with respect to the time axis that is arranged in the horizontal direction. The displayed temperature may be outdoor temperature, or may be indoor temperature of the room where the subject is. Moreover, in this example, the temperature at several timings is displayed as a numerical value.

The third area 207 represents a transition of time in a target period of the graph display. In this example, the third area 207 is close to the first area 203. The third area 207 may be in contact with the first area 203. Alternatively, the third area 207 may overlap the first area 203.

In this embodiment, as the user swipes in the horizontal direction over the first area 203, the graph inside the first area 203 slides. Moreover, the type and contents of the analysis screen displayed in the second area 205 is changed based on the target period of the graph display confirmed by the swiping.

Figure 3:
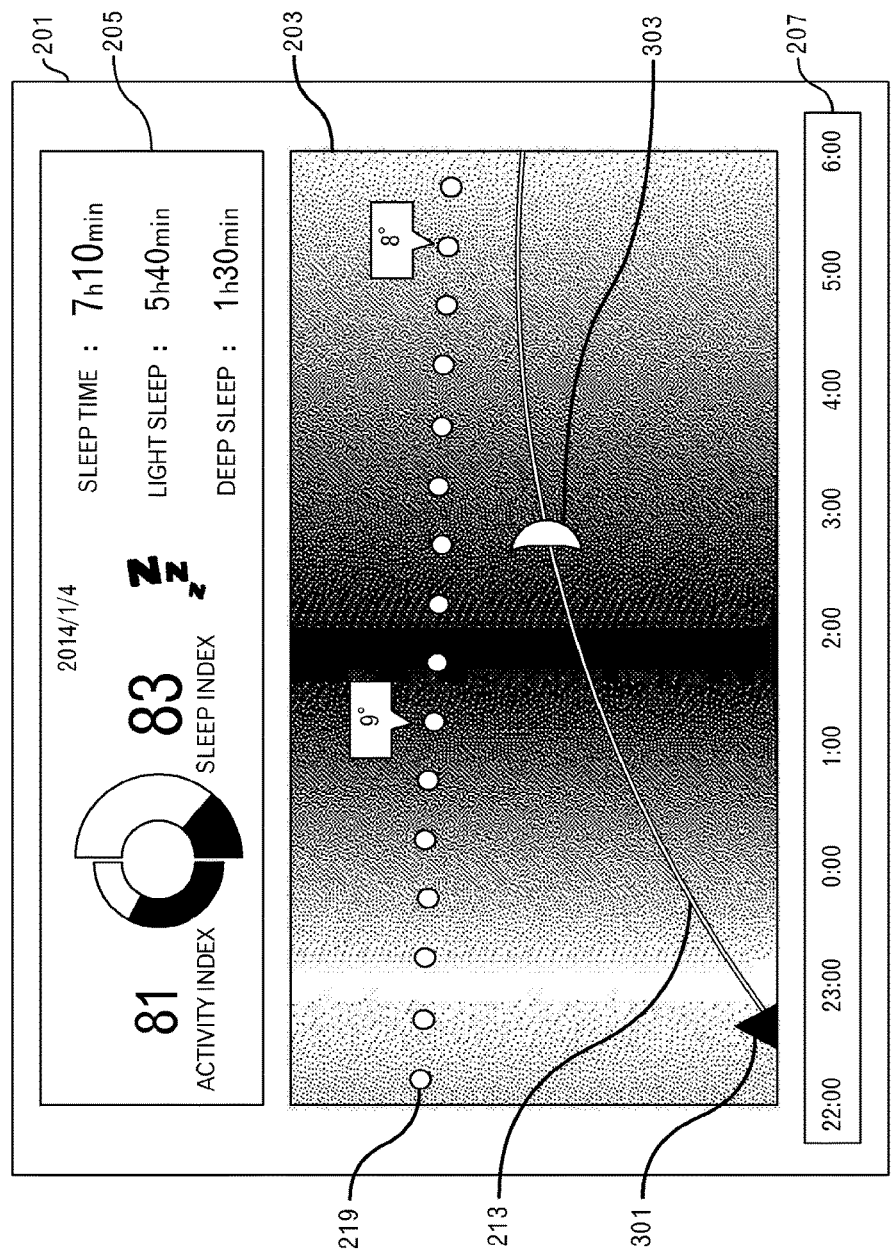
FIG. 3 is a diagram depicting an example of the main screen.

Next, an example of a display when the target period of the graph display is changed by swiping in the horizontal direction will be explained. FIG. 3 illustrates an example of the main screen 201 after swiping. The target period of the graph display in the example in FIG. 3 is the period from Jan. 3, 2014 22:00 to Jan. 4, 2014 6:00. The center time in the example in FIG. 3 is Jan. 4, 2014 2:00. That is, the target period of the graph display in FIG. 3 is set 7 hours before the target period of the graph display in FIG. 2.

In the example in FIG. 3, the period from Jan. 3, 2014 22:00 to about 23:00 represents a degree of the amount of activity. As described above, the area for this period is filled with a color having an "orange" hue. Similarly, a degree of an amount of activity is represented by the shading of the color. Moreover, the period from about Jan. 3, 2014 23:00 to about Jan. 4, 2014 6:00 represents the degree of a depth of sleep. As described above, the area of this period is filled with a color having a "blue" hue. Similarly, a depth of sleep is represented by the shading of the color.

When the sleep period is dominant in the target period of the graph display, or in other words, when the sleep period is longer than the non-sleep period, data related to the sleep state of the subject is displayed. In this example, in addition to the sleep index, each value for an overall sleep time (displayed as "sleep time" on this screen), a light sleep time (displayed as "light sleep" on this screen) and a deep sleep time (displayed as "deep sleep" on this screen) are displayed. The screen like this, which represents the analysis results for the sleep state of a subject, is referred to as a first analysis screen. The first analysis screen has a color tone in which a color having a "blue" hue is mainly used. The activity index related to the active state of subject is also displayed. It is not necessary to limit the first analysis screen to a color tone in which a color having a "blue" hue is used, and the second analysis screen to a color tone in which a color having an "orange" hue is used. However, by using different color type for each other, it is possible to easily view and distinguish between the display for sleep and the display for activity. Moreover, by matching the hues used for the first area 203 and the hues used for the first analysis screen and second analysis screen of the second area 205, it is possible to easily view and distinguish between the display for sleep and the display for activity.

The third area 207 illustrates, as described above, a transition of time in the target period of the graph display.

As described above, a graph related to the environment in the target period of the graph display is also displayed over the first area 203. A line 213 represents a height of the moon. A mark 301 represents a time of the moonrise. In the following, this mark 301 is called the moonrise mark. Moreover, a moon mark 303 represents that an overlapping line 213 corresponds to a height of the moon. The shape of the moon mark 303 represents an appearance of the moon at each age of the moon. Therefore, a user is able to identify the age of the moon according to the displayed shape of the moon mark 303. This is helpful for a user to take into consideration an influence of the age of the moon on the vital activity, for example.

Furthermore, in this embodiment, a graph inside the first area 203 is switched between a graph for the previous day or a graph for the next day, as the user swipes the inside of the first area 203 in the vertical direction. Moreover, contents of the analysis screen that is displayed in the second area 205 is changed based on the target period of the graph display that corresponds to the same time zone of the previous day, or based on the target period of the graph display that corresponds to the same time zone of the next day.

Figure 4:
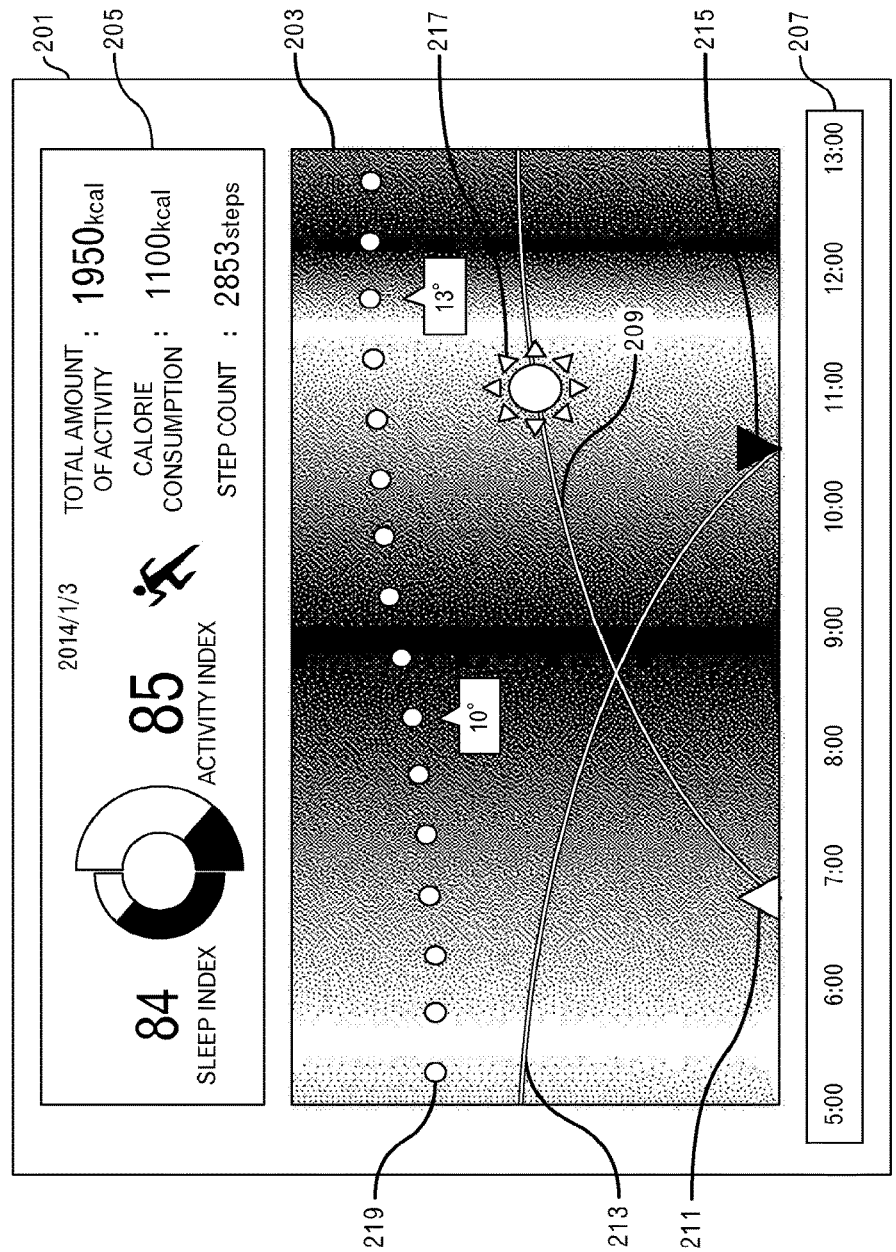
FIG. 4 is a diagram depicting an example of a main screen.

Next, an example of the display when the graph is switched by swiping in the vertical direction will be explained. FIG. 4 illustrates an example of the main screen 201 after swiping. The example in FIG. 4 illustrates a state in which contents of the display is switched to a graph of the previous day is represented as a result of user's swiping downward inside the first area 203 in the state in FIG. 2. The target period of the graph display in the example in FIG. 4 is the period from Jan. 3, 2014 5:00 to 13:00. The center time in the example in FIG. 4 is Jan. 3, 2014 9:00. That is, the target period of the graph display in FIG. 4 is set about 24 hours before the target period of the graph display in FIG. 2.

In the example in FIG. 4, the period on Jan. 3, 2014 from 5:00 to about 5:30 represents a degree of the depth of sleep. As described above, the area of this period is occupied by a color having a "blue" hue. Similarly, the depth of sleep is represented by the shading of the color. Moreover, the period from about 5:30 to about 13:00 represents the degree of an amount of activity. As described above, the area of this period is occupied by a color having an "orange" hue. Similarly, the degree of the amount of activity is represented by the shading of the color.

In the target period of the changed graph display, since the non-sleep period is dominant, the second analysis screen is displayed. Each value for a sleep index, an activity index, a total amount of activity, calorie consumption and a step count are analysis results based on the target period of the changed graph display.

Figure 5:
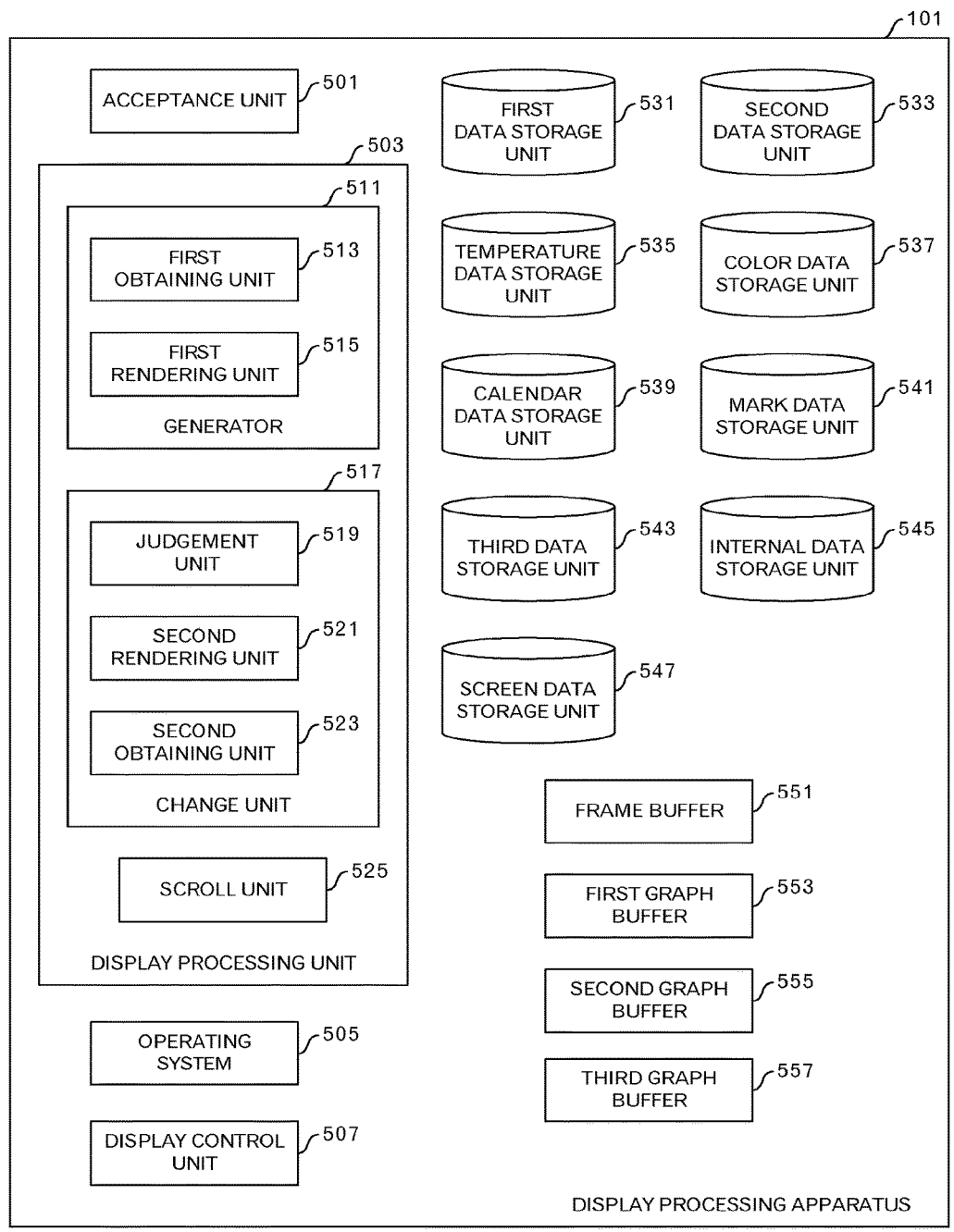
FIG. 5 is a diagram depicting an example of module configuration of a display processing apparatus.

Next, modular configuration of the display processing apparatus 101 will be explained. FIG. 5 illustrates an example of the modular configuration of the display processing apparatus 101. The display processing apparatus 101 has an acceptance unit 501, a display processing unit 503, an operating system 505 and a display control unit 507. The acceptance unit 501 receives instructions according to a user operation.

The display processing unit 503 mainly performs processing for displaying the main screen. The display processing unit 503 has a generator 511. The generator 511 generates a graph image that is displayed in the first area 203. The generator 511 has a first obtaining unit 513 and a first rendering unit 515. The first obtaining unit 513 obtains data that is used for generating the graph image. The first rendering unit 515 renders the graph image.

The display processing unit 503 has a change unit 517. The change unit 517 changes the configuration of the screen that is displayed in the second area 205 according to change in the state of the vital activity of a subject in the target period of the graph display. In other words, the change unit 517 selects the first analysis screen or the second analysis screen based on the state of the vital activity of the subject in the target period of the graph display, and generates an analysis screen for the selected screen. The change unit 517 has a judgement unit 519, a second rendering unit 521 and a second obtaining unit 523. The judgement unit 519 determines which of the sleep period and the non-sleep period in the target period of the graph display is dominant. The second rendering unit 521 renders the first analysis screen and the second analysis screen. The second obtaining unit 523 obtains data that is used for generating the first analysis screen and the second analysis screen.

The operating system 505 detects, for example, an event by a user operation. The display control unit 507 displays an image on the display device according to image data.

The display processing apparatus 101 has a first data storage unit 531, a second data storage unit 533, a temperature data storage unit 535, a color data storage unit 537, a calendar data storage unit 539, a mark data storage unit 541, a third data storage unit 543, an internal data storage unit 545 and a screen data storage unit 547.

The first data storage unit 531 stores first data related to the level of the depth of sleep. The second data storage unit 533 stores second data related to the level of the amount of activity. The temperature data storage unit 535 stores temperature data that associates each time point with a temperature. The temperature data may also be data that is measured in the display processing apparatus 101. The temperature data may also be data that is obtained from outside The color data storage unit 537 stores color data that associates a color code with each level of the depth of sleep and each level of the amount of activity.

The calendar data storage unit 539 stores, in addition to calendar data, data such as a time of the sunrise, a time of the sunset, a time of the moonrise, a time of the moonset and an age of the moon for each day. Furthermore, the calendar data storage unit 539 stores data for a height of the sun and a height of the moon at each time.

The mark data storage unit 541 stores various kinds of marks such as a sun mark 217, moon mark 303, sunrise mark 211, sunset mark 1109 (described later in FIG. 11), moonrise mark 301, moonset mark 215, temperature mark 219 and the like. The moon mark 303 is associated with the age of the moon.

The third data storage unit 543 stores auxiliary data. When a step count is measured by the display processing apparatus 101, the measured step count is stored in the third data storage unit 543. The internal data storage unit 545 stores parameters that are used internally.

The screen data storage unit 547 stores image data in which the background, predetermined marks, item names and the like are rendered in the first analysis screen. Furthermore, the screen data storage unit 547 stores image data in which the background, predetermined marks, item names and the like are rendered in the second analysis screen. After finishing the processing for displaying the main screen, the screen data storage unit 547 may also store data for that main screen. The data for that main screen is used when displaying the previous main screen again at startup. When the main screen is not displayed again, the screen data storage unit 547 may be omitted.

The display processing apparatus 101 has a frame buffer 551, a first graph buffer 553, a second graph buffer 555 and a third graph buffer 557. The frame buffer 551 stores image data to be displayed on the display device. The first graph buffer 553 stores a first graph image. The second graph buffer 555 stores a second graph image. The third graph buffer 557 stores a third graph image. The first graph image is a graph image that corresponds to the previous day of the day that is the display target (hereafter, referred to as that day). The second graph image is an image of a graph that corresponds to that day. The third graph image is an image of a graph that corresponds to the next day of that day. The first graph image to the third graph image will be described later using FIG. 11 and the like.

FIG. 6 illustrates an example of first data. The first data in this example is in a table format. The first data has records for each measurement time zone. The length of a measurement time zone in this example is 2 minutes. The records have a field for storing the measurement date, a field for storing the measurement time zone, and a field for storing the level of the depth of sleep. In this example, the level of the depth of sleep is a value from 0 to 30. When the level of the depth of sleep is 0, the subject is in a non-sleep state. When the level of the depth of sleep is 1 or more, the subject is in a sleep state. The maximum level may also be a value other than 30.

FIG. 7 illustrates an example of second data. The second data in this example is in a table format. The second data has records for each measurement time zone. The length of the measurement time zone in this example is two minutes. The records have a field for storing the measurement date, a field for storing the measurement time zone, and a field for storing the level of the amount of activity. In this example, the level of the amount of activity is a value from 0 to 30. When the level of the amount of activity is 1 or more, the subject is in an awake state, or in other words, is in a non-sleep state. The level of the amount of activity represents the intensity of activity. In other words, a large value for the level of the amount of activity means that the activity is intense. The maximum level may be a value other than 30. When the level of the amount of activity is 0, the subject is not in an active state.

Figure 8:
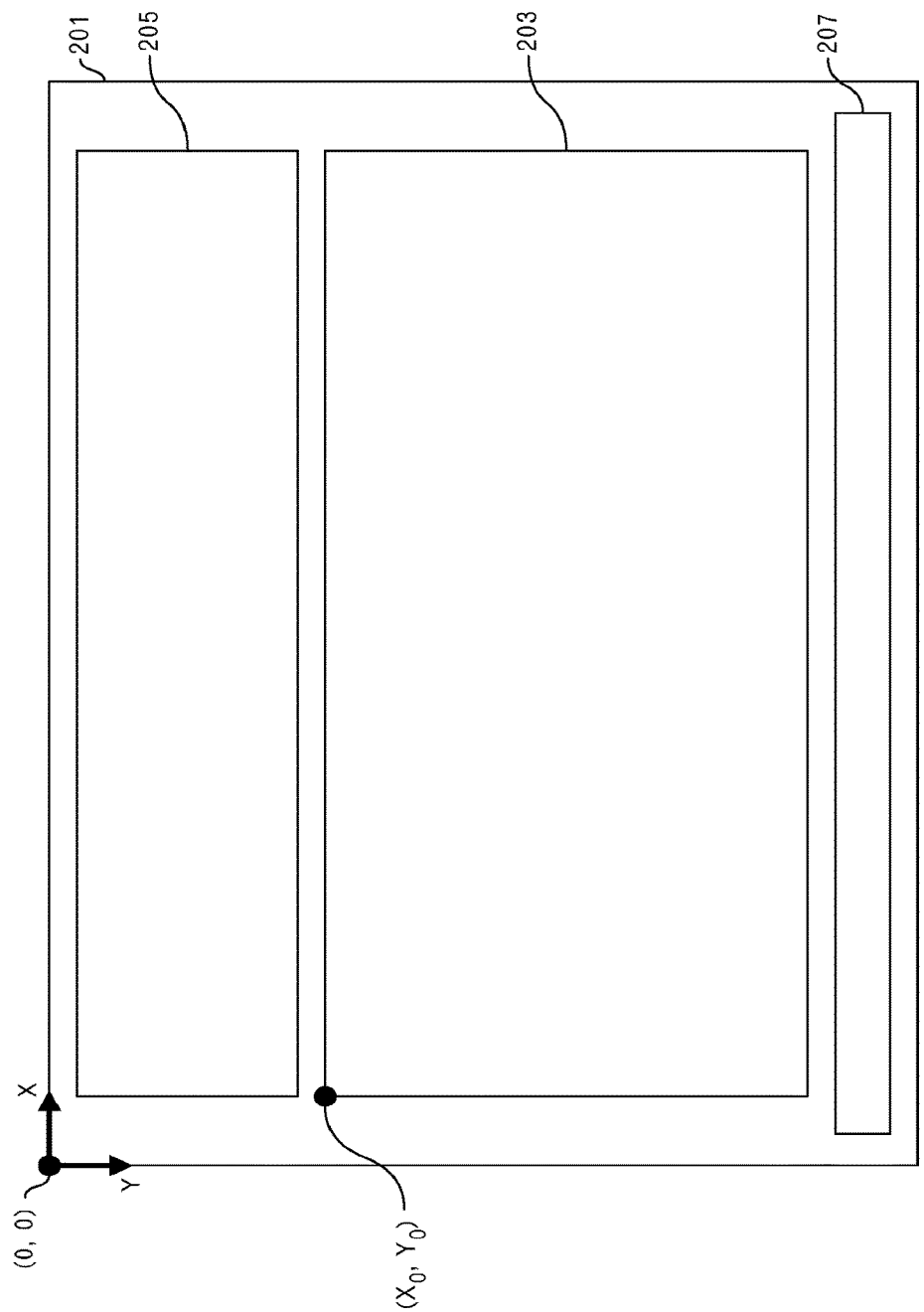
FIG. 8 is a diagram depicting a layout example of the main screen.

Next, the layout of the main screen 201 will be explained. FIG. 8 illustrates an example of the layout of a main screen 201. As illustrated in FIG. 8, a first area 203, a second area 205 and a third area 207 are arranged on the main screen 201. The coordinates (X, Y) in the main screen 201 are represented in a coordinate system whose origin is located on the upper left. The X-axis is positive in the right direction. The Y-axis is positive in the downward direction. The origin of the first area 203 is set as coordinates $(X_0, Y_0)$. The advancement of time is expressed in the right direction. The data for the main screen 201 is stored in the frame buffer 551.

Figure 9:
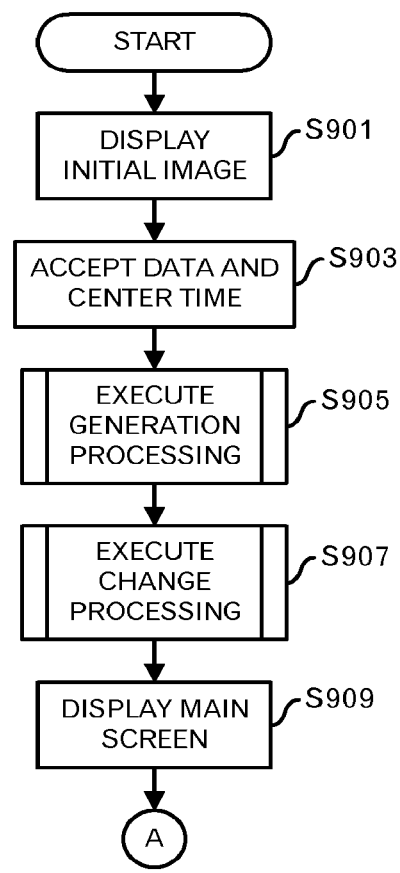
FIG. 9 is a diagram depicting an example of a main processing flow.

FIG. 9 illustrates an example of the flow of main processing. The display processing unit 503 displays a predetermined initial image (S901). Alternatively, the display processing unit 503 may display the main screen again that was displayed when the previous processing ended. In that case, the image data for the main screen that was displayed when the previous processing ended is stored in the screen data storage unit 547, and the display processing unit 503 obtains the image data for that main screen from the screen data storage unit 547.

The acceptance unit 501 receives the date and the center time through user operation for example (S903). The date is a date of a day that includes the center time. Then, the acceptance unit 501 specifies a target period for the graph display so that the length is a predetermined length (8 hours, in this example). In this example, 4 hours before the central time is set as the start time, and 4 hours after the central time is set as the end time. In this way, when the target period for the graph display is a predetermined length, the target period of the graph display is designated by the user performing an operation giving an instruction for the date and center time.

Alternatively, the acceptance unit 501 may directly receive the target period for the graph display through user operation. Then the acceptance unit 501 may specify the date and center time based on the target period of the graph display.

The generator 511 executes the generation processing (S905). In the generation processing, the graph image described above is generated.

Figure 10:
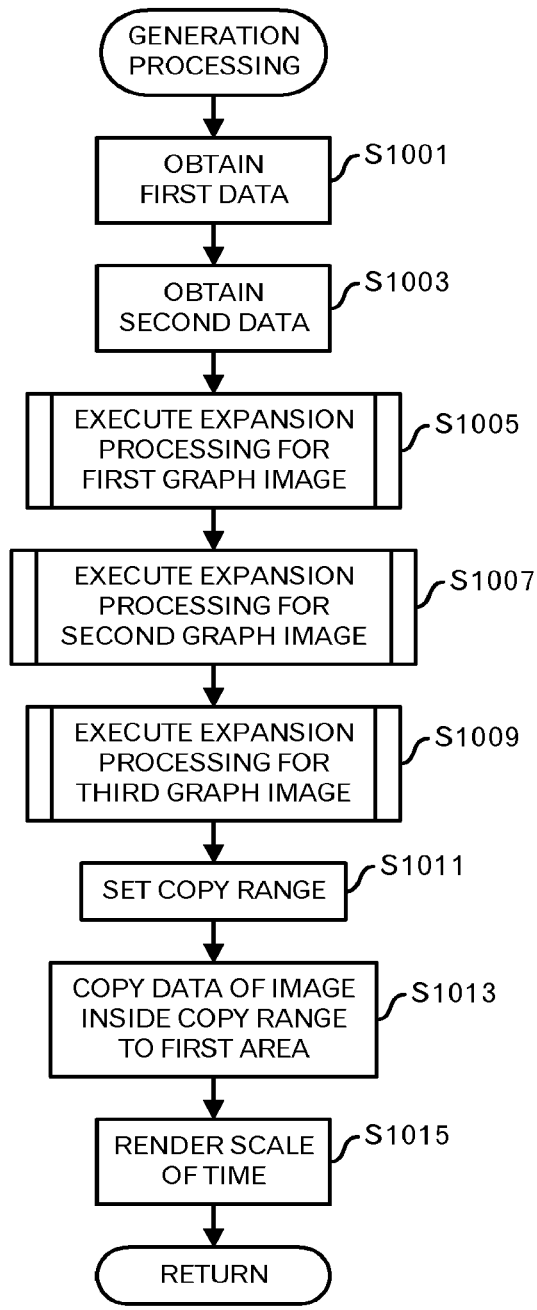
FIG. 10 is a diagram depicting an example of a generation processing flow.

FIG. 10 illustrates an example of a generation processing flow. The first obtaining unit 513 obtains the first data from the management apparatus 103, and stores the first data in first data storage unit 531 (S1001). The first obtaining unit 513 may also obtain the first data from the measurement apparatus 105*a* or the measurement apparatus 105*b*. When the display processing apparatus 101 itself generates the first data, the processing of S1001 may be omitted. Moreover, the first obtaining unit 513 may not obtain first data again, which has already been stored.

The first obtaining unit 513 obtains the second data from the management apparatus 103, and stores the second data in the second data storage unit 533 (S1003). The first obtaining unit 513 may also obtain the second data from the measurement apparatus 105*a* or the measurement apparatus 105*b*. When the display processing apparatus 101 itself generates the second data, the processing of S1003 may be omitted. The first obtaining unit 513 may not obtain second data again, which has already been stored.

The first rendering unit 515 executes expansion processing for the first graph image (S1005). In the expansion processing for the first graph image, the first graph image is expanded in the first graph buffer 553. The first graph is a graph for the day before that day (hereafter, referred to as the previous day). The first graph in this example is in a heat map format as described above.

Next, the first rendering unit 515 executes the expansion processing for the second graph image (S1007). In the expansion processing for the second graph image, the second graph image is expanded in the second graph buffer 555. The second graph is a graph for that day. The second graph in this example is also in a heat map format.

Next, the first rendering unit 515 further executes the expansion processing for expanding the third graph image (S1009). In the expansion processing for the third graph image, the third graph image is expanded in the third graph buffer 557. The third graph is a graph for the day after that day (hereafter, referred to as the next day). The third graph in this example is also in a heat map format.

When only work days are the target of the graph, for example, days off may be excluded. Therefore, when the previous day on the calendar is a day off, the previous day becomes the first work day by going back in time. Similarly, when the next day on the calendar is a day off, the next day becomes the first work day by going forward in time.

In the expansion processing for the first graph image to the third graph image, the storage destinations for the graph images are different, however, the processing order is the same.

Figure 11:
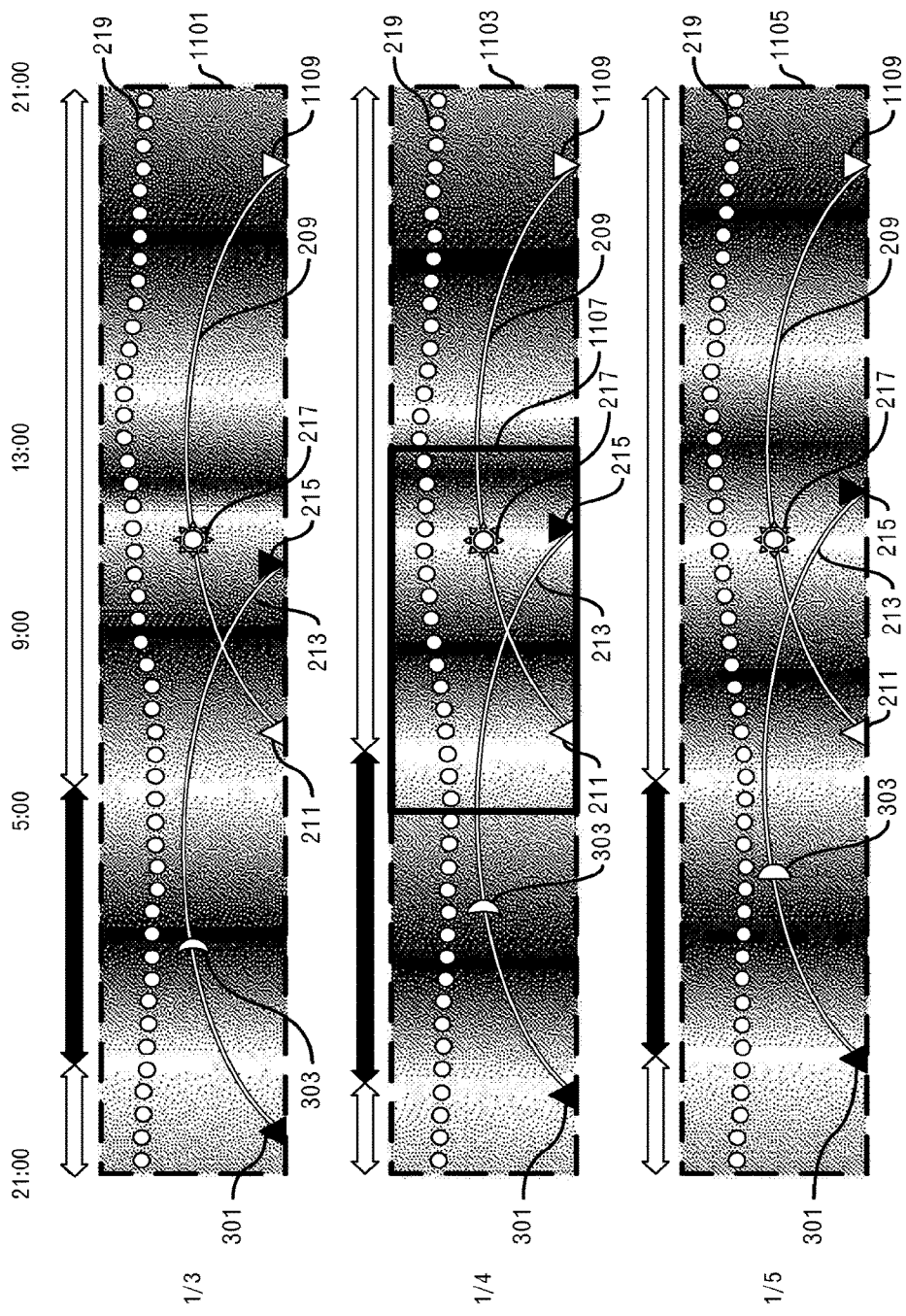
FIG. 11 is a diagram depicting an example of image data stored in a graph buffer.

Next, the expansion processing will be explained using FIGS. 11 to 22. FIG. 11 illustrates an example of data for graph images stored in the graph buffer. FIG. 11 illustrates a first graph image 1101, second graph image 1103 and third graph image 1105 that are expanded by the expansion processing.

The period for which the second graph image 1103 is expanded includes the target period of the graph display, and also includes the period before and after the target period, which are continuous with the target period. A length of the period before the target period and a length of the period after the target period are, in this example, the same as the length of the target period of the graph display. In this example, the length of the target period is 8 hours, and the period for which the graph is expanded is 24 hours that is three times longer. The time in the center of the period in which the graph is expanded coincides with the center time in the target period of the graph display.

The period for which the first graph image 1101 is expanded is the period 24 hours before the period in which the second graph image 1103 is expanded. The period for which the third graph image 1105 is expanded is the period 24 hours after the period for which the second graph image 1103 is expanded. However, the period for which the first graph image 1101 is expanded may be the period 24 hours before the target period of the graph display. In that case, the length of the period for which the first graph image 1101 is expanded is 8 hours. Moreover, the period for which the third graph image 1105 is expanded may also be the period 24 hours after the target period of the graph display. In that case, the length of the period for which the third graph image 1105 is expanded is 8 hours. In the following, the period for which a graph image is expanded is called the graph period.

In FIG. 11, an arrow that is conveniently filled in is attached to the range filled with color having a "blue" hue. An arrow that is conveniently fringed is attached to the range filled with color having an "orange" hue. The same is true in the following drawings as well. In this example, "blue" is an example of a first hue that represents the sleep state. Moreover, in this example, "orange" is an example of a second hue that represents the active state.

A copy range 1107 represents a range in the frame buffer 551 of the image that will be copied to the first area 203. The shape of the copy range 1107 is the same as the shape of the first area 203, and the size of the copy range 1107 is the same as the size of the first area 203. The horizontal range in the copy range 1107 corresponds to the target period of the graph display.

The mark 1109 represents the time of the sunset. In the following, this mark 1109 is called the sunset mark.

Figure 12:
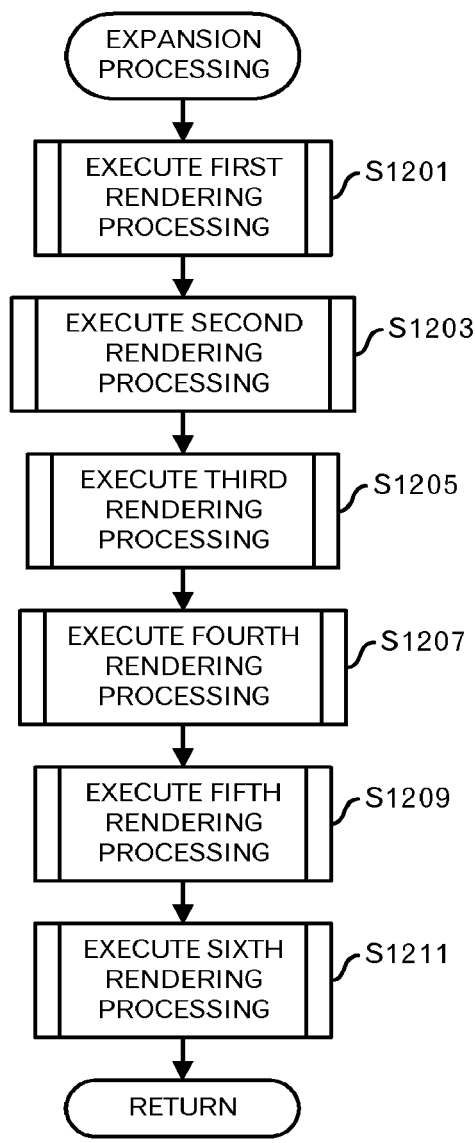
FIG. 12 is a diagram depicting an example of an expansion processing flow.

FIG. 12 illustrates an example of the expansion processing flow. The first rendering unit 515 executes first rendering processing (S1201). In the first rendering processing, a graph in a heat map format is rendered as a part of the graph image.

Next, the first rendering unit 515 executes second rendering processing (S1203). In the second rendering processing, a line 209 that represents the height of the sun, a sunrise mark 211 and a sunset mark 1109 are rendered as a part of the graph image.

Next, the first rendering unit 515 executes third rendering processing (S1205). In the third rendering processing, a line 213 that represents the height of the moon, a moonrise mark 301 and a moonset mark 215 are rendered as a part of the graph image.

Next, the first rendering unit 515 executes fourth rendering processing (S1207). In the fourth rendering processing, a sun mark 217 is rendered as a part of the graph image.

Next, the first rendering unit 515 executes fifth rendering processing (S1209). In the fifth rendering processing, a moon mark 303 is rendered as part of the graph image.

Finally, the first rendering unit 515 executes sixth rendering processing (S1211). In the sixth rendering processing, a mark 219 representing the temperature is rendered as a part of the graph image. In the following, processing will be explained in order from the first rendering processing to the sixth rendering processing.

Figure 13:
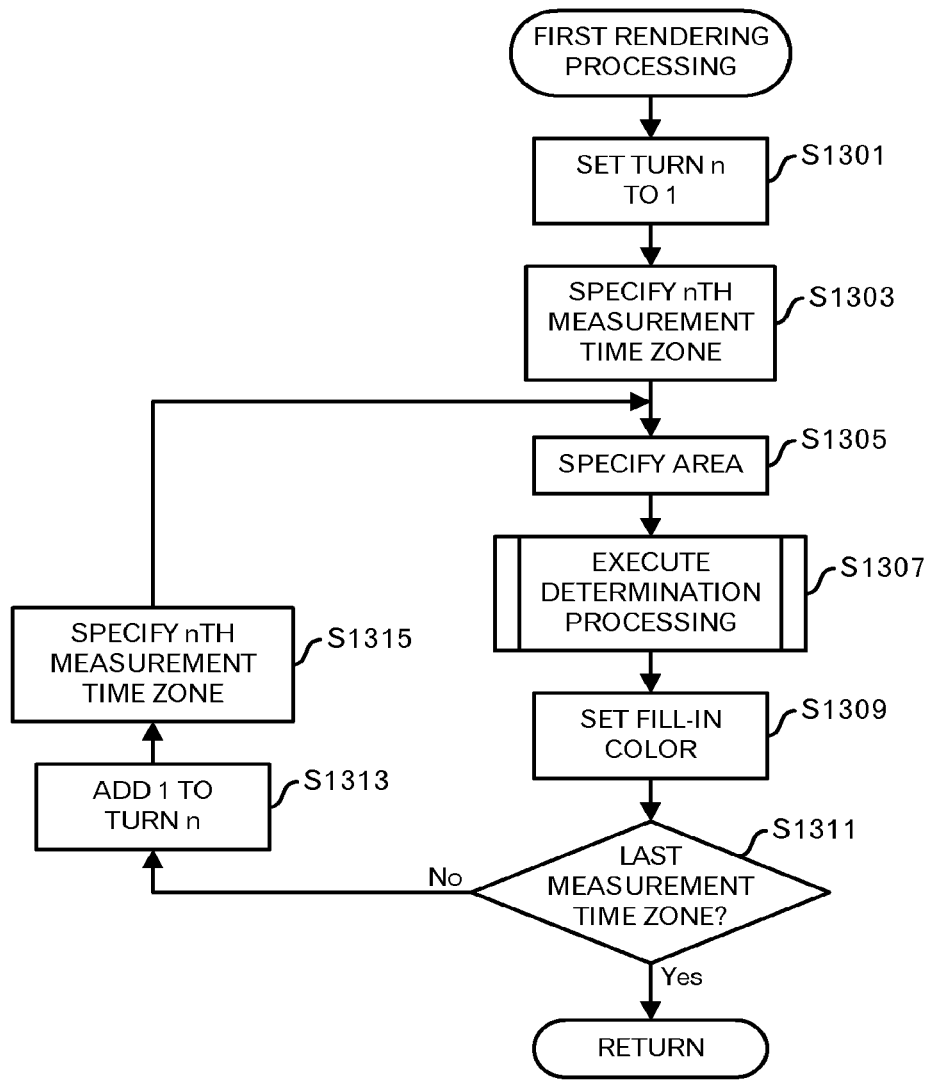
FIG. 13 is a diagram depicting an example of a first rendering processing flow.

FIG. 13 illustrates an example of a first rendering processing flow. The first rendering unit 515 sequentially processes each measurement time zone that is included in the graph period in chronological order. First, the first rendering unit 515 sets a parameter n to 1, which represents a turn of the measurement time zone to be processed (S1301).

Hereafter, the first rendering unit 515 specifies, by using the parameter n that represents the turn, the measurement time zone that is to be processed. The parameter n that represents the turn is stored in the internal data storage unit 545. The generator 511 specifies the nth measurement time zone in the graph period (S1303).

The first rendering unit 515 specifies the area that will be filled with a specific color (S1305). The area that is filled with the specific color will be explained using FIG. 14. Here, the second graph image 1103 will be explained as an example, however, the same explanation is true for the first graph image 1101 and the third graph image 1105.

Figure 14:
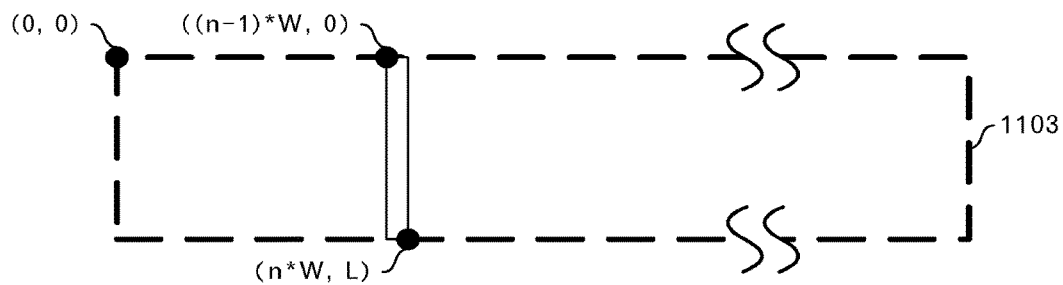
FIG. 14 is a diagram depicting coordinates of a filled area.

The origin of the second graph image 1103 is located on the upper left end. The width of the area that is filled with the specific color is set as W, and similarly the height is set as L. L is the same as the height of the first area 203, and W is the value of the first area 203 divided by the number of measurement time zones. The area that corresponds to the nth measurement time zone and that is filled with the specific color is illustrated as being a rectangular shape. The upper left coordinates of the area that is filled with the specific color is $((n-1)*W, 0)$ as illustrated in FIG. 14. The lower right coordinates of the area that is filled with the specific color is $(n*W, L)$ as illustrated in FIG. 14.

The first rendering unit 515 calculates, in S1305, the upper left coordinates $((n-1)*W, 0)$ and the lower right coordinates $(n*W, L)$ of the area that is filled with the specific color.

The first rendering unit 515 executes determination processing (S1307). In the determination processing, the fill-in color is set. In this first embodiment, determination processing (A) is executed.

Figure 15:
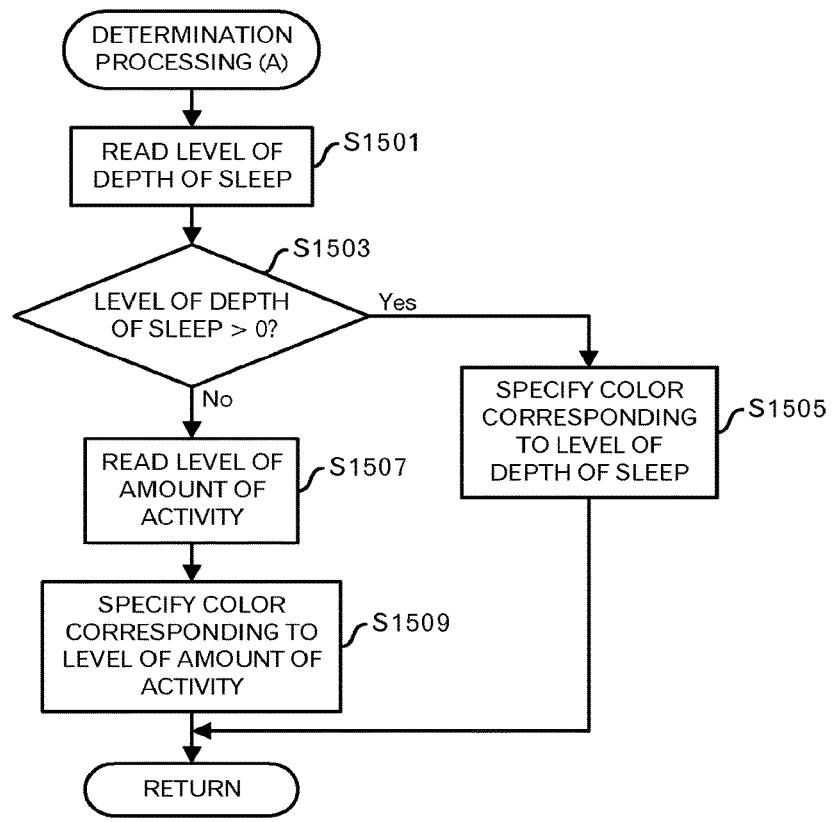
FIG. 15 is a diagram depicting an example of a determination processing (A) flow.

FIG. 15 illustrates an example of a flow of the determination processing (A). The first rendering unit 515 reads the level of the depth of sleep, which corresponds to the specified measurement time zone, from the first data that is stored in the first data storage unit 531 (S1501).

The first rendering unit 515 determines whether or not the level of the depth of sleep is greater than 0 (S1503). When it is determined that the level of the depth of sleep is greater than 0, the first rendering unit 515 specifies a color code that corresponds to the level of the depth of sleep, which was read in S1501 based on color data that is stored in the color data storage unit 537 (S1505).

The hues of the colors specified by color codes that are associated with each level of the depth of sleep are all a first hue ("blue" in this example). These colors are set so as to gradually become darker as the value of the level of the depth of sleep goes from small to large. Therefore, the value of the chroma of the color of the color code that is associated with level "1" of the depth of sleep is the smallest, the values of the chroma become gradually larger from level "2" on, and the value of the chroma of the color of the color code that is associated with the largest level value is the largest. An achromatic color (white in this example) is associated with level "0" of the depth of sleep.

However, when it is determined that the level of the depth of sleep is not greater than 0, or in other words, when the level of the depth of sleep is 0, the first rendering unit 515 reads the level of the amount of activity that corresponds to the specified measurement time zone from the second data that is stored in the second data storage unit 533 (S1507). The first rendering unit 515 specifies a color code that corresponds to that level of the amount of activity based on color data that is stored in the color data storage unit 537 (S1509).

The hues of the colors of the color code that are associated with each of the levels of the amounts of activity are all a second hue ("orange" in this example). These colors are set so as to gradually become darker as the value of the level of the amount of activity goes from small to large. Therefore, the value of the chroma of the color of the color code that is associated with level "1" of the amount of activity is the smallest, the values of the saturation become gradually larger from level "2" on, and the value of the chroma of the color of the color code that is associated with the largest level value is the largest. An achromatic color (white in this example) is associated with level "0" of the amount of activity.

After the determination processing (A) ends, the processing shifts to the processing of S1309 illustrated in FIG. 13.

The explanation will return to the explanation of FIG. 13. The first rendering unit 515 sets the color code specified in S1307 as a color that will be filled in the area specified in S1305 (S1309). The color code that is set here is stored as pixel data for inside the area in one of the first graph buffer 553 to third graph buffer 557 that are the targets of writing.

The first rendering unit 515 determines whether or not the processed measurement time zone corresponds to the end of the graph period (S1311). When it is determined that the processed measurement time zone does not correspond to the end of the graph period, the first rendering unit 515 adds 1 to the parameter n that represents the turn (S1313). The generator 511 specifies the nth measurement time zone (S1315). Then, the processing returns to S1305, and the processing described above is repeated.

When it is determined that the processed measurement time zone corresponds to the end of the graph period, the first rendering processing ends, and the processing returns to the calling source.

Figure 16:
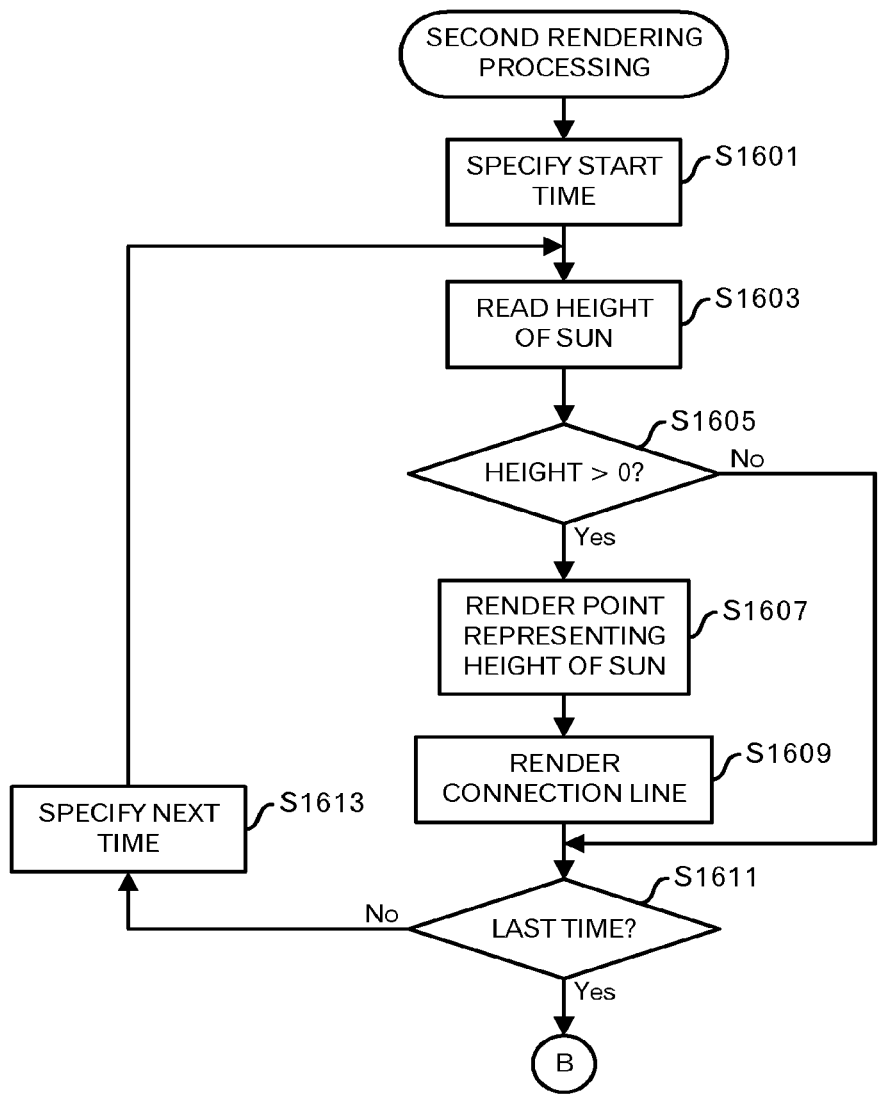
FIG. 16 is a diagram depicting an example of a second rendering processing flow.

Next, the second rendering processing will be explained. FIG. 16 illustrates an example of a second rendering processing flow. In the second rendering processing, processing is performed for each timing specified at a predetermined interval of the graph period. The first rendering unit 515 specifies the start time that is included in the graph period (S1601). The first rendering unit 515 reads, from data that is stored in the calendar data storage unit 539, the height of the sun at that time (S1603). The first rendering unit 515 determines whether or not the obtained height of the sun is greater than 0 (S1605).

When it is determined that the obtained height of the sun is greater than 0, the first rendering unit 515 renders a point that represents the height of the sun (S1607). In order to render the point that represents the height of the sun, the first rendering unit 515 calculates the X coordinate that corresponds to that time and the Y coordinate that corresponds to the height of the sun. The Y coordinate is found, for example, by calculating the height L of the first area 203−(height of the sun*a predetermined magnification rate). The first rendering unit 515 renders a connection line connecting the point that represents the height of the sun at the previous time, and the point that represents the height of the sun at the current time (S1609).

Then, the first rendering unit 515 determines whether or not the time for which the processing was performed is the last time that is included in the graph period (S1611). When it is determined that the time for which the processing was performed is not the last time that is included in the graph period, the first rendering unit 515 specifies the next time (S1613). For example, the next time is found by adding a predetermined amount of time to the current time. Processing then returns to the processing of S1603, and the processing described above is repeated.

Figure 17:
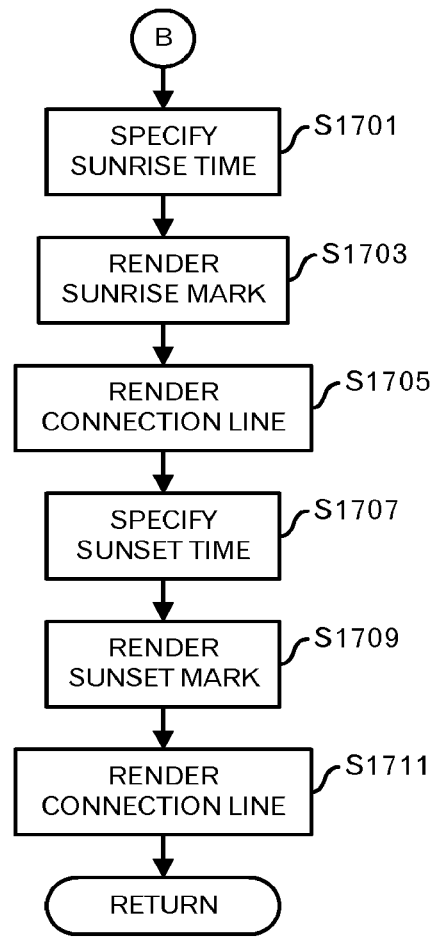
FIG. 17 is a diagram depicting an example of the second rendering processing flow.

However, when it is determined in S1611 that the time for which the processing was performed is the last time that is included in the graph period, the processing shifts to the processing of S1701 illustrated in FIG. 17 by way of terminal B.

In S1605, when it is determined that the height of the sun obtained in S1603 is not greater than 0, the processing shifts to the determination processing in S1611 without rendering a point and the connection line representing the height of the sun.

The explanation will move on to an explanation of FIG. 17. The first rendering unit 515 specifies a sunrise time, which is included in the graph period, from data that is stored in the calendar data storage unit 539 (S1701). The first rendering unit 515 renders a sunrise mark 211 at a positon that corresponds to the sunrise time and is near the third area 207 (S1703). At this time, the first rendering unit 515 obtains data for the sunrise mark 211 from the mark data storage unit 541, and places the sunrise mark 211 at that position.

Then, the first rendering unit 515 renders a connection line connecting the sunrise mark 211 and a point that represents the next height of the sun (S1705). However, when the sunrise time is not included in the graph period, the first rendering unit 515 does not render the sunrise mark 211 and the connection line.

The first rendering unit 515 specifies a sunset time, which is included in the graph period, from data that is stored in the calendar data storage unit 539 (S1707). The first rendering unit 515 renders a sunset mark 1109 at a position that corresponds to the sunset time and is near the third area 207 (S1709). At this time, the first rendering unit 515 obtains data for the sunset mark 1109 from the mark data storage unit 541, and places the sunset mark 1109 at that position.

Then, the first rendering unit 515 renders a connection line that connects the sunset mark 1109 and the point that represents the previous height of the sun (S1711). However, when the sunset time is not included in the graph period, the first rendering unit 515 does not render the sunset mark 1109 and the connection line. Then, the second rendering processing ends and the processing returns to the calling source.

Figure 18:
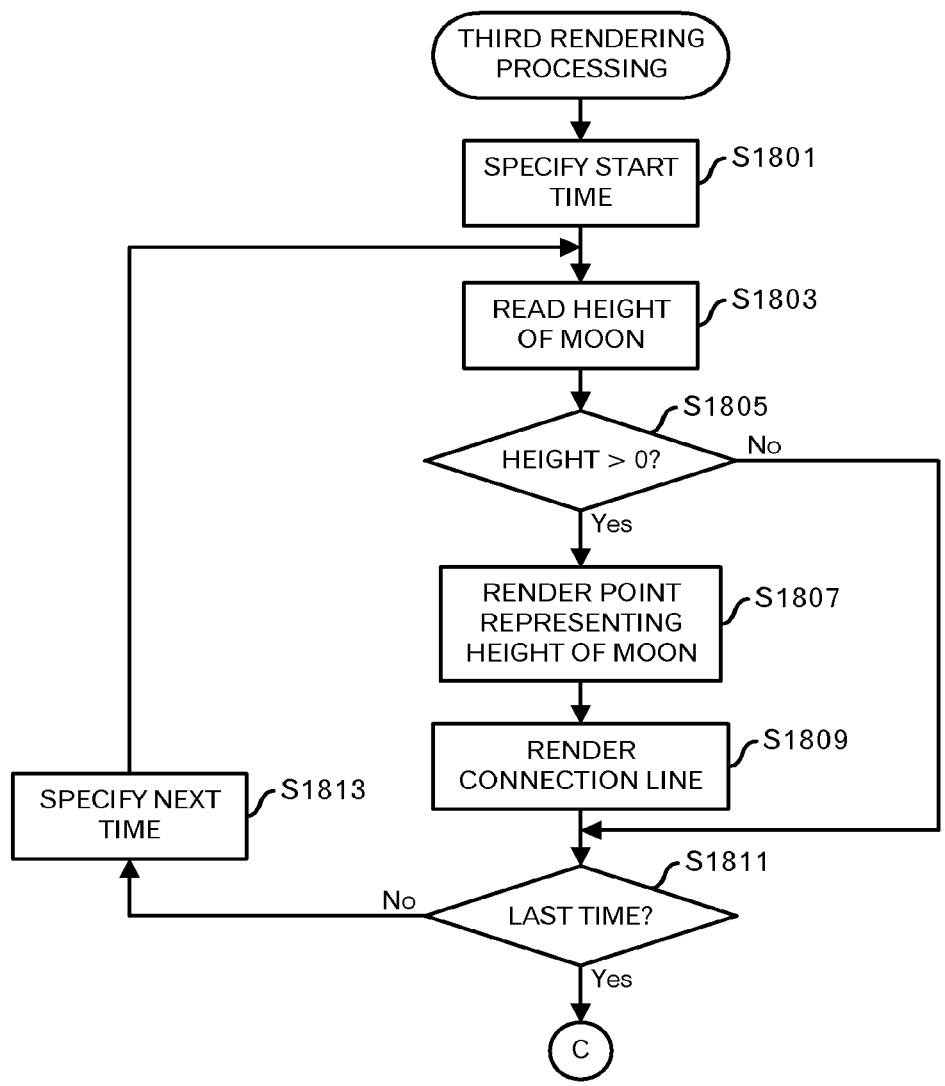
FIG. 18 is a diagram depicting an example of a third rendering processing flow.

Next, the third rendering processing will be explained. FIG. 18 illustrates an example of a third rendering processing flow. In the third rendering processing, processing is performed for each timing specified at a predetermined interval of the graph period. The first rendering unit 515 specifies the start time that is included in the graph period (S1801). The first rendering unit 515 reads, from data that is stored in the calendar data storage unit 539, the height of the moon at that time (S1803). The first rendering unit 515 determines whether or not the obtained height of the moon is greater than 0 (S1805).

When it is determined that the obtained height of the moon is greater than 0, the first rendering unit 515 renders a point that represents the height of the moon (S1807). The first rendering unit 515 calculates the X coordinate that corresponds to that time, and the Y coordinate that corresponds to the height of the moon for that point that represents the height of the moon. The Y coordinate is found, for example, by calculating the height L of the first area 203−(height of the moon*a predetermined magnification rate). The first rendering unit 515 renders a connection line that connects the point that represents the height of the moon at the previous time and the point that represents the height of the moon at the current time (S1809).

Then, the first rendering unit 515 determines whether or not the time for which the processing was performed is the last time that is included in the graph period (S1811). When it is determined that the time for which the processing was performed is not the last time that is included in the graph period, the first rendering unit 515 specifies the next time (S1813). For example, the next time is found, for example, by adding a predetermined amount of time to the current time. Then, processing returns to the processing of S1803, and the processing described above is repeated.

Figure 19:
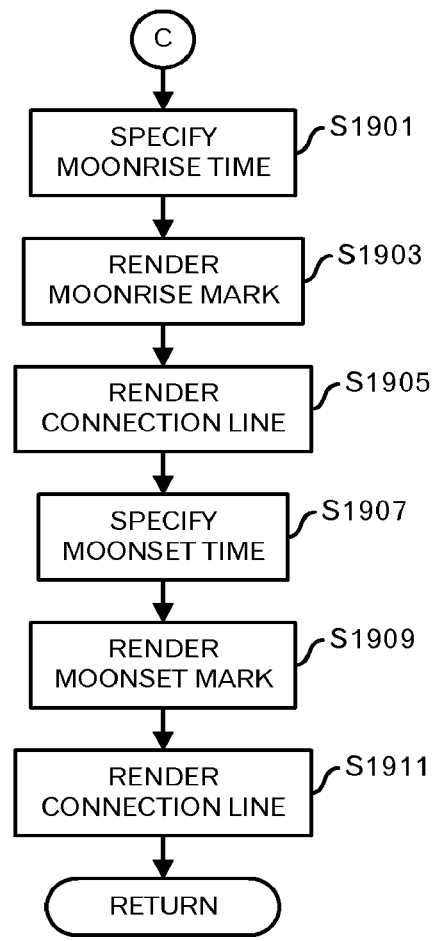
FIG. 19 is a diagram depicting an example of the third rendering processing flow.

However, in S1811, when it is determined that the time for which the processing was performed is the last time that is included in the graph period, the processing shifts to the processing of S1901 illustrated in FIG. 19 by way of terminal C.

In S1805, when it is determined that the height of the moon obtained in S1803 is not greater than 0, the processing shifts to the determination processing in S1811 without rendering the point and the connection line representing the height of the moon.

The explanation will shift to an explanation of FIG. 19. The first rendering unit 515 specifies, from data stored in the calendar data storage unit 539, a moonrise time that is included in the graph period (S1901). The first rendering unit 515 renders a moonrise mark 301 at a position that corresponds to the moonrise time and is near the third area 207 (S1903). At this time, the first rendering unit 515 obtains data for the moonrise mark 301 from the mark data storage unit 541, and places that moonrise mark 301 at that position.

Then, the first rendering unit 515 renders a connection line that connects the moonrise mark 301 and a point that represents the next height of the moon (S1905). However, when the moonrise time is not included in the graph period, the first rendering unit 515 does not render the moonrise mark 301 or the connection line.

The first rendering unit 515 specifies, from data stored in the calendar data storage unit 539, a moonset time that is included in the graph period (S1907). The first rendering unit 515 renders the moonset mark 215 at a position that corresponds to the moonset time and is near the third area 207 (S1909). At this time, the first rendering unit 515 obtains data for the moonset mark 215 from the mark data storage unit 541, and places the moonset mark 215 at that position.

Then, the first rendering unit 515 renders a connection line that connects the moonset mark 215 and the point that represents the previous height of the moon (S1911). However, when the moonset time is not included in the graph period, the first rendering unit 515 does not render the moonset mark 215 and the connection line. Then, the third rendering processing ends and returns to the calling source.

Figure 20:
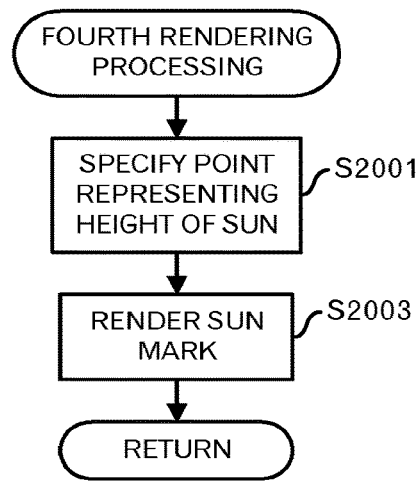
FIG. 20 is a diagram depicting an example of a fourth rendering processing flow.

Next, the fourth rendering processing will be explained. FIG. 20 illustrates an example of a fourth rendering processing flow. The first rendering unit 515 specifies a point from among the points that represent the heights of the sun, which were rendered in S1607 in FIG. 16 (S2001). The first rendering unit 515 may a specify point whose height is near a predetermined height. Alternatively, the first rendering unit 515 may specify a point that is related to the maximum value of the height. Alternatively, the first rendering unit 515 may specify a point at a predetermined time.

Then, the first rendering unit 515 renders a sun mark 217 at the position of the specified point (S2003). At this time, the first rendering unit 515 obtains data for the sun mark 217 from the mark data storage unit 541, and renders that sun mark 217 over that position. The first rendering unit 515 then ends the fourth rendering processing and returns to the calling source.

Figure 21:
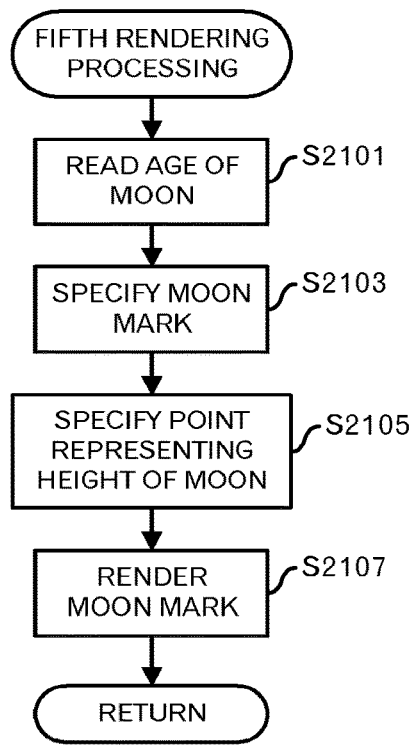
FIG. 21 is a diagram depicting an example of a fifth rendering processing flow.

Next, the fifth rendering processing will be explained. FIG. 21 illustrates an example of a fifth rendering processing flow. The first rendering unit 515 reads the age of the moon for that day from data that is stored in the calendar data storage unit 539 (S2101). The first rendering unit 515 specifies a moon mark 303 from among the moon marks 303 that are stored in the mark data storage unit 541 that corresponds to the age of the moon read in S2101 (S2103).

The first rendering unit 515 specifies a point that represents a height of the moon from among the points rendered in S1807 in FIG. 18 that indicate the height of the moon (S2105). The first rendering unit 515 may specify a point that is near a predetermined height. Alternatively, the first rendering unit 515 may specify a point related to the height having the maximum value. Alternatively, the first rendering unit 515 may specify a point at a predetermined time.

Then, the first rendering unit 515 renders the moon mark 303 specified in S2103 at the position of the specified point (S2107). At this time, the first rendering unit 515 obtains data for the moon mark 303 from the mark data storage unit 541, and renders the moon mark 303 over that position. Then, the fifth rendering processing ends, and processing returns to the calling source.

Figure 22:
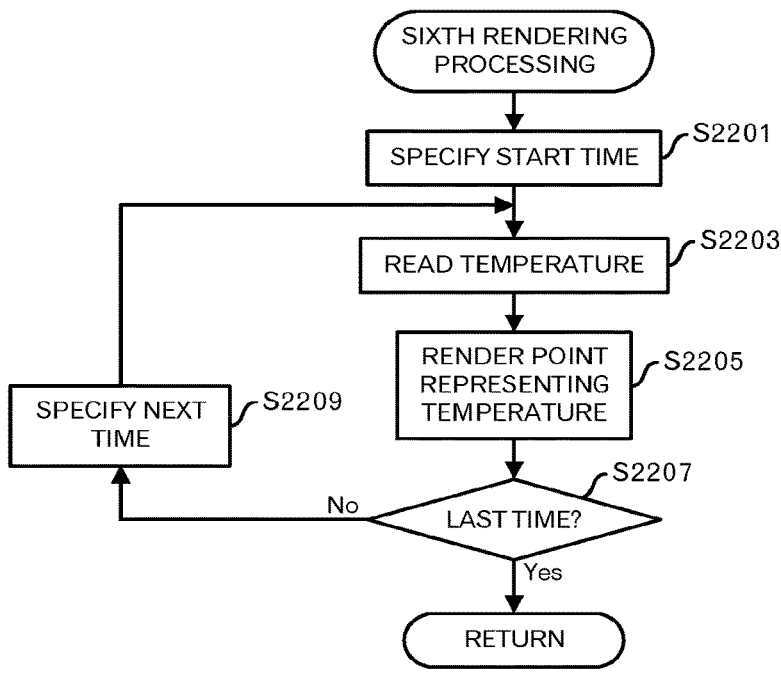
FIG. 22 is a diagram depicting an example of a sixth rendering processing flow.

Next, the sixth rendering processing will be explained. FIG. 22 illustrates an example of a sixth rendering processing flow. In the sixth rendering processing, processing is performed for each timing specified at a predetermined interval of the graph period. The first rendering unit 515 specifies the start time that is included in the graph period (S2201). The first rendering unit 515 reads the temperature at that time from temperature data that is stored in the temperature data storage unit 535 (S2203). The first rendering unit 515 renders a mark 219 representing the temperature (S2205). The temperature is represented such that the negative direction on the Y-axis is the positive direction. The first rendering unit 515 calculates the X coordinate that corresponds to that time and the Y coordinate that corresponds to the temperature. The Y coordinate is found, for example, by calculating the height L of the first area 203−(temperature*predetermined magnification rate+predetermined value). The predetermined value is a value for adjustment so that the temperature graph shifts upward or downward.

The first rendering unit 515, as illustrated in the example in FIGS. 2 to 4, may display values at several points in time representing the temperatures at those points in time.

The first rendering unit 515 determines whether or not the time for which the processing was performed is the last time that is included in the graph period (S2207). When it is determined that the time for which the processing was performed is not the last time that is included in the graph period, the first rendering unit 515 specifies the next time (S2209). For example, the next time is found by adding a predetermined amount of time to the current time. The processing then returns to the processing of S2203, and repeats the processing described above.

However, in S2207, when it is determined that the time for which the processing was performed is the last time that is included in the graph period, the sixth rendering processing ends. This completes the explanation of the expansion processing.

The explanation returns to the explanation of FIG. 10. The generator 511 sets the copy range 1107 that was explained using FIG. 11 (S1011).

The generator 511 copies data of the image inside the copy range 1107 to the first area 203 in the frame buffer 551 (S1013). The first rendering unit 515 renders, in the third area 207 of the main screen 201, a scale representing the start time and the end time of the target period of the graph display and some timings in that time period (S1015). Therefore, the third area 207 represents the transition of time in the target period of the graph display. This completes the explanation of the generation processing.

The explanation will return to the explanation of FIG. 9. The change unit 517 executes change processing (S907). In the change processing, configuration of a screen that is displayed in the second area 205 is changed according to a change in the state of the vital activity of a subject in the target period of the graph display.

Figure 23:
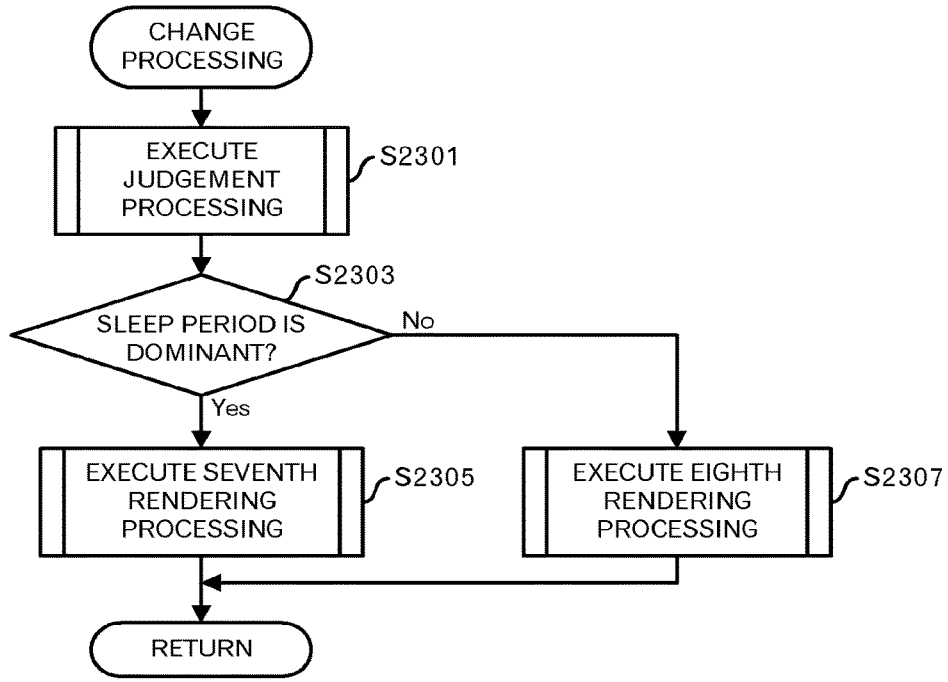
FIG. 23 is a diagram depicting an example of a change processing flow.

The change processing will be explained using FIGS. 23 to 29. FIG. 23 illustrates an example of a change processing flow. The judgement unit 519 executes judgement processing (S2301). In the judgement processing, the judgement unit 519 determines which of the sleep period and non-sleep period in the target period of the graph display is dominant. In this first embodiment, judgement processing (A) is executed.

Figure 24:
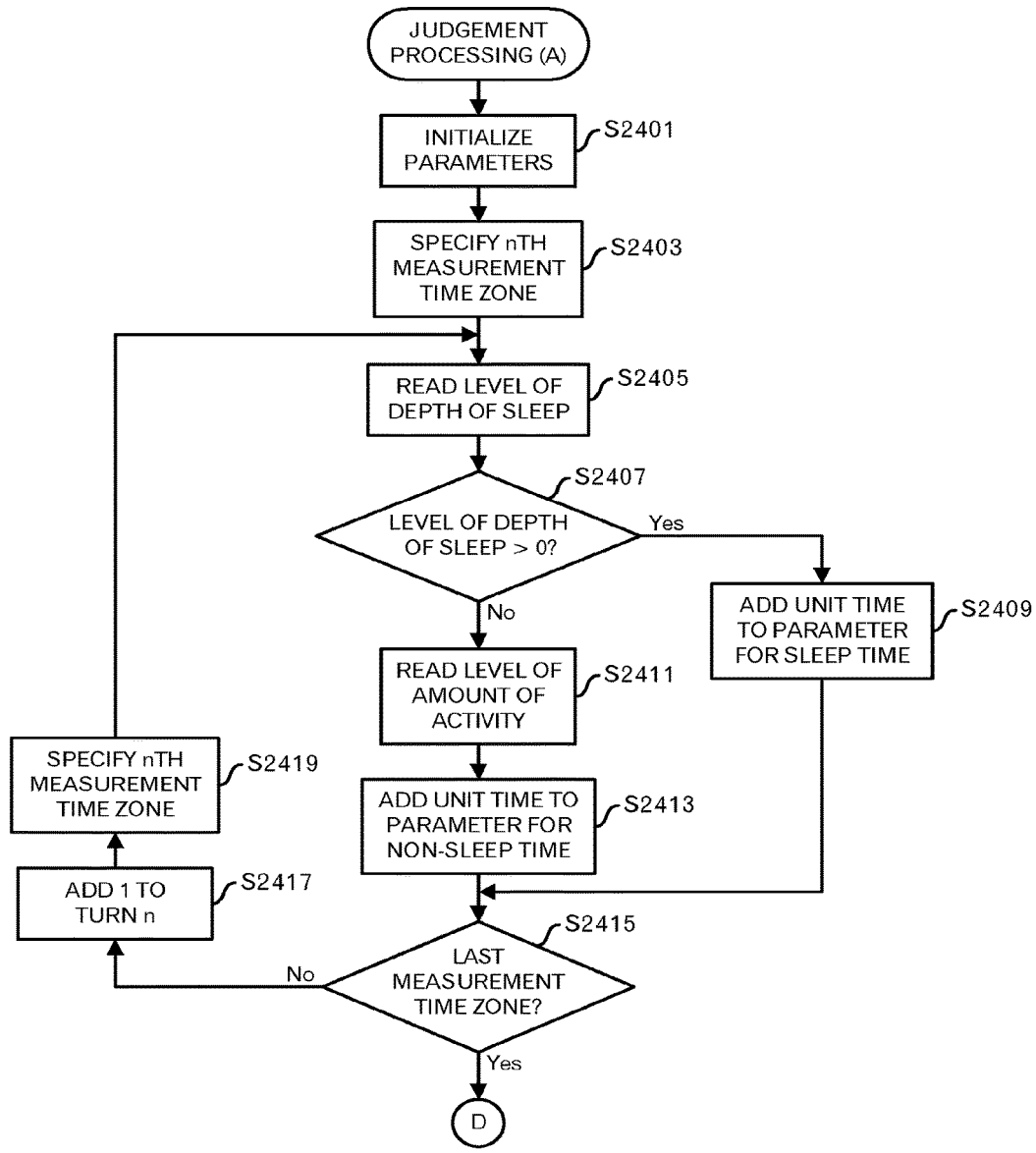
FIG. 24 is a diagram depicting an example of the judgement processing (A) flow.

FIG. 24 illustrates an example of a judgement processing (A) flow. In the judgement processing (A), the judgement unit 519 processes, in chronological order, each measurement time zone, which is included in the target period of the graph display, and calculates a total sleep time and a total non-sleep time.

The judgement unit 519 initializes parameters that are stored in the internal data storage unit 545 (S2401). More specifically, the judgement unit 519 sets the parameters for the sleep time to 0, and further sets the parameters for the non-sleep time to 0. Furthermore, the judgement unit 519 sets the parameter n that represents a turn of the measurement time zone to be processed to 1.

In the following, the judgement unit 519 uses the parameter n that represents the turn and specifies the measurement time zone to be processed. Therefore, the judgement unit 519 specifies the nth measurement time zone in the target period of the graph display (S2403).

The judgement unit 519 reads, from the first data that is stored in the first data storage unit 531, the level of the depth of sleep that corresponds to the specified measurement time zone (S2405).

The judgement unit 519 determines whether or not the level of the depth of sleep is greater than 0 (S2407). When it is determined that the level of the depth of sleep is greater than 0, the judgement unit 519 adds a unit time to the parameter for the sleep time (S2409). The unit time corresponds to the length of a measurement time zone.

When it is determined that the level of the depth of sleep is not greater than 0, or in other words, when the level of the depth of sleep is 0, the judgement unit 519 reads the level of the amount of activity that corresponds to the specified measurement time zone from the second data that is stored in the second data storage unit 533 (S2411). The judgement unit 519 adds a unit time to the parameter for the non-sleep time (S2413). The unit time corresponds to the length of the measurement time zone.

The judgement unit 519 determines whether or not the processed measurement time zone corresponds to the end of the target period of the graph display (S2415). When it is determined that the processed measurement time zone does not correspond to the end of the target period of the graph display, the judgement unit 519 adds 1 to the parameter n that represents the turn (S2417). The judgement unit 519 specifies the nth measurement time zone (S2419). The processing then returns to S2405, and the processing described above is repeated.

Figure 25:
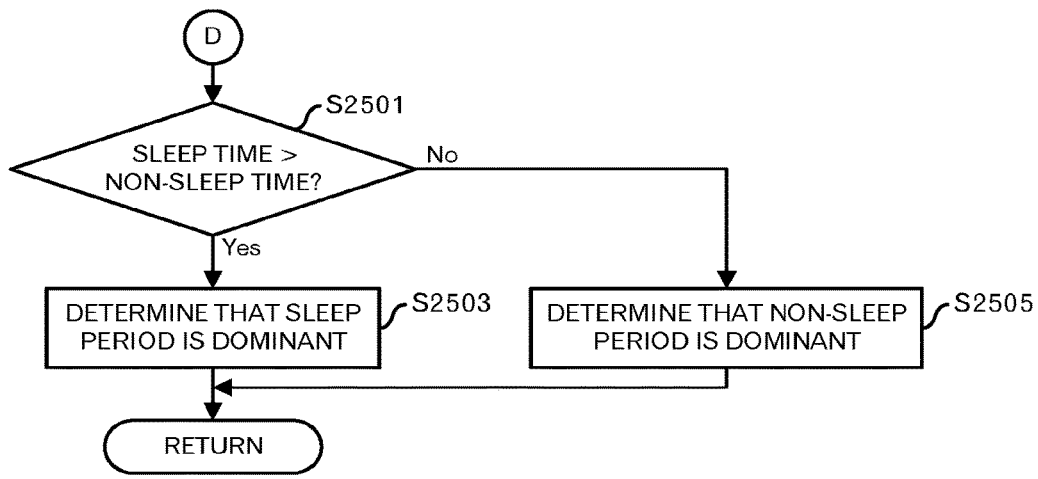
FIG. 25 is a diagram depicting an example of the judgement processing (A) flow.

When it is determined that the processed measurement time zone corresponds to the end of the target period of the graph display, the processing shifts to the processing of S2501 illustrated in FIG. 25 by way of terminal D.

The explanation shifts to an explanation of FIG. 25. The judgement unit 519 determines whether or not the value of the total sleep time (the value of the parameter for the sleep time) is greater than the value of the total non-sleep time (the value of the parameter for the non-sleep time) (S2501). When it is determined that the value of the total sleep time is greater than the value of the total non-sleep time, the judgement unit 519 determines that the sleep period is dominant (S2503). However, when it is determined that the value of the total sleep time is not greater than the value of the total non-sleep time, the judgement unit 519 determines that the non-sleep period is dominant (S2505). After the judgement processing (A) ends, the processing shifts to the processing of S2303 illustrated in FIG. 23.

The explanation returns to the explanation of FIG. 23. The second rendering unit 521 branches the processing depending on whether or not the sleep period is determined as being dominant (S2303). When it is determined that the sleep period is dominant, the change unit 517 executes seventh rendering processing (S2305). In the seventh rendering processing, a first analysis screen is rendered. The seventh rendering processing will be described later using FIG. 26 and FIG. 27.

However, when it is determined that the sleep period is not dominant, or in other words, when it is determined that the non-sleep period is dominant, the change unit 517 executes an eighth rendering processing (S2307). In the eighth rendering processing, a second analysis screen is rendered. The eighth rendering processing will be described later using FIG. 28 and FIG. 29.

Figure 26:
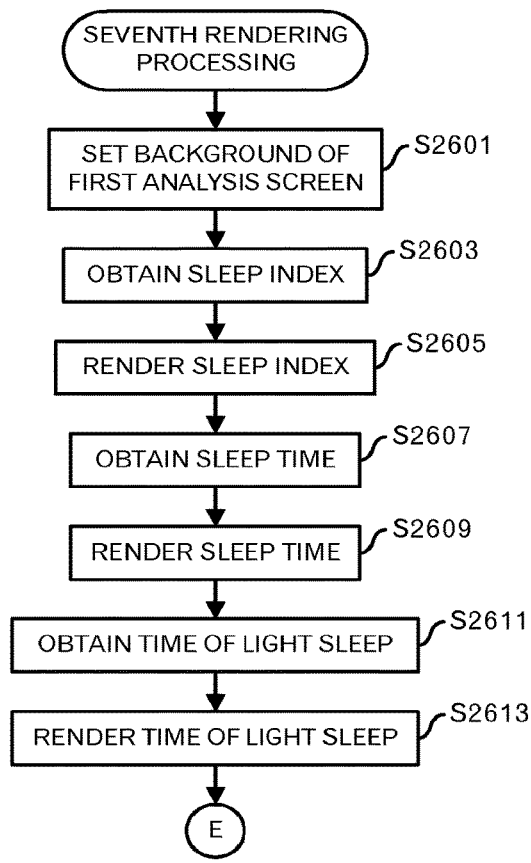
FIG. 26 is a diagram depicting an example of a seventh rendering processing flow.

The seventh rendering processing described above will be explained. FIG. 26 illustrates an example of a seventh rendering processing flow. The second rendering unit 521 obtains image data in which the background, predetermined marks, item names and like for the first analysis screen are rendered from the screen data storage unit 547, and sets an image in the second area 205 of the main screen 201 using that image data (S2601). In this image, the color of the first hue fills more area than the color of other hues. For example, the color of the first hue occupies the area for the background and the predetermined marks. The background may also have an achromatic color.

The second obtaining unit 523 sends the date and the center time of that day to the management apparatus 103, and obtains a sleep index that corresponds to the date and that center time from the management apparatus 103 (S2603). Here, the sleep index is the percentage of the time of deep sleep in the total time of sleep in a predetermined period that includes the center time in the date (for example the period from 12 hours before the center time to 12 hours after the center time). However, the sleep index may also be calculated based on other criteria. The second obtaining unit 523 may also obtain the sleep index from the measurement apparatus 105*a* or the measurement apparatus 105*b*. The second rendering unit 521 itself may also calculate the sleep time.

The second rendering unit 521 renders the obtained or calculated sleep index (S2605). In this example, the second rendering unit 521 renders a number representing the sleep index at a predetermined position as illustrated in FIG. 3, and also renders a graph having a semicircular shape. This graph is rendered in the color of the first hue. The number that represents the sleep index is rendered larger than a number that represents an activity index. Moreover, the rendered graph that represents the sleep index is larger than a graph that represents an activity index. In this way, the sleep index may be easily understood when the sleep period is dominant.

The second obtaining unit 523 sends the date and the center time of that day to the management apparatus 103 and obtains, from the management apparatus 103, the sleep time that corresponds to the date and the center time (S2607). Here, the sleep time means the total sleep time in a predetermined period that includes the center time in the date (for example, the period from 12 hours before the center time to 12 hours after the center time). The second obtaining unit 523 may also obtain the sleep time from the measurement apparatus 105*a* or the measurement apparatus 105*b*. The second rendering unit 521 itself may also calculate the sleep time.

The second rendering unit 521 renders the obtained or calculated sleep time (S2609). In this example, the second rendering unit 521 renders a number that represents the sleep time at a predetermined position such as illustrated in FIG. 3.

The second obtaining unit 523 sends the date and the center time of that day to the management apparatus 103, and obtains, from the management apparatus 103, the time of light sleep that corresponds to the date and the center time (S2611). Here, the time of light sleep means the length of the period of light sleep in the sleep time in a predetermined period that includes the center time in the date (for example, a period from 12 hours before the center time to 12 hours after the center time). The second obtaining unit 523 may also obtain the time of light sleep from the measurement apparatus 105*a* or the measurement apparatus 105*b*. The second rendering unit 521 itself may also calculate the time of light sleep.

The second rendering unit 521 renders the obtained or calculated time of light sleep (S2613). In this example, the second rendering unit 521 renders a number that represents the time of light sleep at a predetermined position as illustrated in FIG. 3. Then, the processing shifts to the processing of S2701 illustrated in FIG. 27 by way of terminal E.

Figure 27:
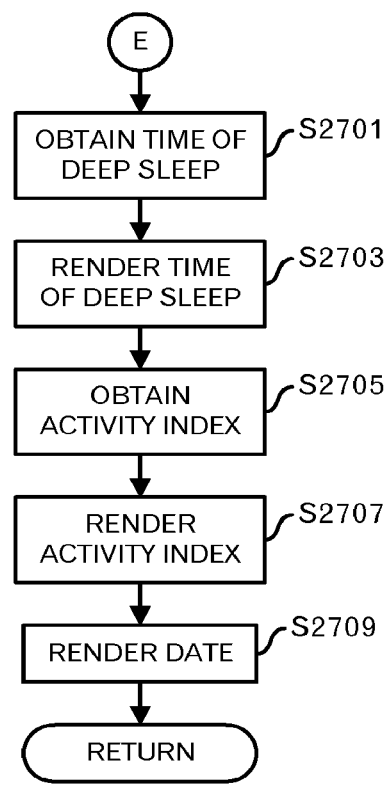
FIG. 27 is a diagram depicting an example of the seventh rendering processing flow.

The explanation shifts to an explanation of FIG. 27. The second obtaining unit 523 sends the date and the center time of that day to the management apparatus 103, and obtains the time of deep sleep that corresponds to the date and the center time from the management apparatus 103 (S2701). Here, the time of deep sleep means the length of a period of deep sleep in the sleep time in a predetermined period that includes the center time in the date (for example, a period from 12 hours before the center time to 12 hours after the center time). The second obtaining unit 523 may also obtain the time of deep sleep from the measurement apparatus 105*a* or the measurement apparatus 105*b*. The second rendering unit 521 itself may also calculate the time of deep sleep.

The second rendering unit 521 renders the obtained or calculated time of deep sleep (S2703). In this example, the second rendering unit 521 renders a number that represents the time of deep sleep at a predetermined position as illustrated in FIG. 3.

The second obtaining unit 523 sends the date and the center time of that day to the management apparatus 103, and obtains an activity index that corresponds to the date and the center time from the management apparatus 103 (S2705). Here, the activity index is a percentage of the amount of activity with respect to the total amount of energy consumption in a predetermined period that includes the center time in the date (for example, a period from 12 hours before the center time to 12 hours after the center time). However, the activity index may also be calculated based on other criteria. The second obtaining unit 523 may also obtain the activity index from the measurement apparatus 105*a* or the measurement apparatus 105*b*. The second rendering unit 521 itself may also calculate the activity index.

The second rendering unit 521 renders the obtained or calculated activity index (S2707). In this example, the second rendering unit 521 renders a number that represents the activity index at a predetermined position as illustrated in FIG. 3, and also renders a graph having a semicircular shape. This graph is rendered in the color of the second hue. The number that represents the activity index is rendered smaller than the number that represents the sleep index. The graph that represents the activity index is also rendered smaller than the graph that represents the sleep index.

Then, the second rendering unit 521 renders the date of that day (S2709). In this example, the second rendering unit 521 renders a number that represents the data as illustrated in FIG. 3.

Figure 28:
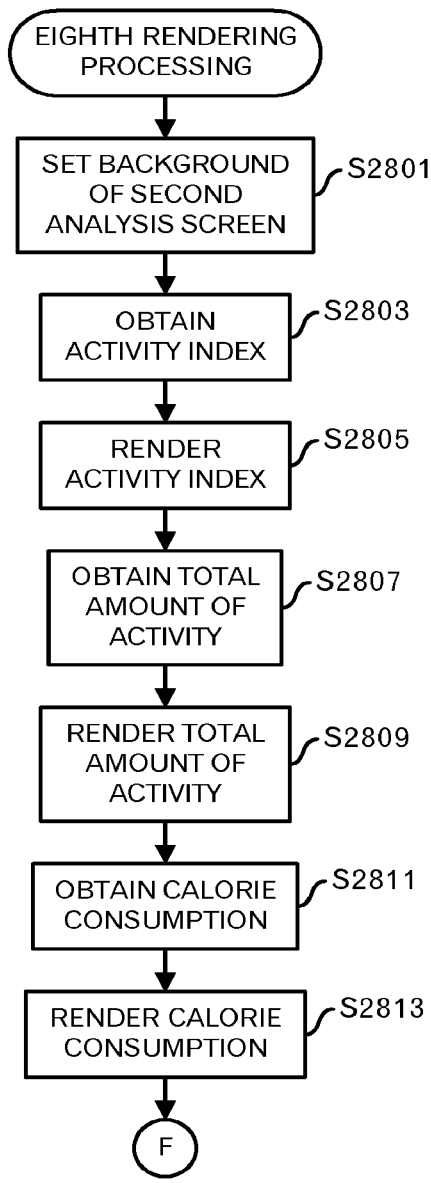
FIG. 28 is a diagram depicting an example of an eighth rendering processing flow.

Next, eighth rendering processing will be explained. FIG. 28 illustrates an example of an eighth rendering processing flow. The second rendering unit 521 obtains image data in which the background, predetermined marks, item names and the like of a second analysis screen are rendered from the screen data storage unit 547, and sets an image according to that image data in the second area 205 of the main screen 201 (S2801). In this image, the color of the second hue fills more area than colors of other hues. For example, the color of the second hue fills the area of the background and predetermined mark. The background may also have an achromatic color.

The second obtaining unit 523, as in S2705 in FIG. 27, obtains or calculates the activity index (S2803).

The second rendering unit 521 renders the activity index (S2805). In this example, the second rendering unit 521 renders a number that represents the activity index at a predetermined position as illustrated in FIG. 2, and also renders a graph having a semicircular shape. This graph is rendered in the color of the second hue. The number that represents the activity index is rendered bigger than the number that represents the sleep index. The graph that represents the activity index is also rendered bigger than the graph that represents the sleep index. In doing so, when the non-sleep period is dominant, it is easy to understand the activity index.

The second obtaining unit 523 sends the date and the center time of that day to the management apparatus 103, and obtains the total amount of activity that corresponds to the date and the center time from the management apparatus 103 (S2807). Here, the total amount of activity means the total amount of activity in a predetermined period that includes the center time in the date (for example a period from 12 hours before the center time to 12 hours after the center time). The second obtaining unit 523 may also obtain the total amount of activity from the measurement apparatus 105a or the measurement apparatus 105b. The second rendering unit 521 may also calculate the total amount of activity by itself.

The second rendering unit 521 renders the obtained or calculated total amount of activity (S2809). In this example, the second rendering unit 521 renders a number that represents the total amount of activity at a predetermined position as illustrated in FIG. 2.

The second obtaining unit 523 sends the date and the center time for that day to the management apparatus 103, and obtains the calorie consumption that corresponds to the date and the center time from the management apparatus 103 (S2811). Here, the calorie consumption means the total calorie consumption in a predetermined period that includes the center time in the date (for example, a period from 12 hours before the center time to 12 hours after the center time). The second obtaining unit 523 may also obtain the calorie consumption from the measurement apparatus 105a or measurement apparatus 105b. The second rendering unit 521 itself may also calculate the calorie consumption.

The second rendering unit 521 renders the obtained or calculated calorie consumption (S2813). In this example, the second rendering unit 521 renders a number that represents the calorie consumption at a predetermined position as illustrated in FIG. 2. The processing then shifts to the processing in S2901 illustrated in FIG. 29 by way of terminal F.

Figure 29:
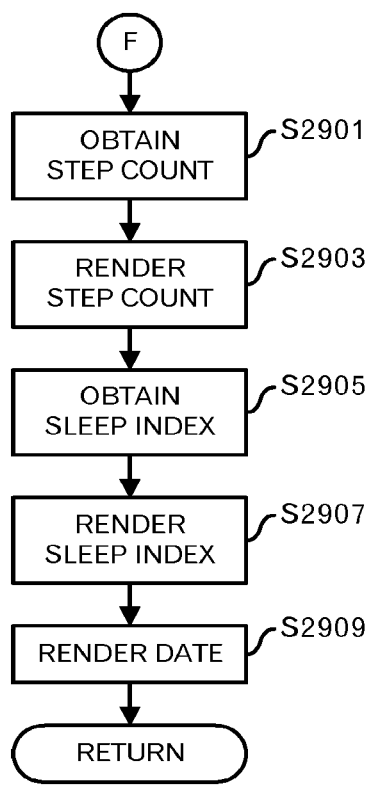
FIG. 29 is a diagram depicting an example of the eighth rendering processing flow.

The explanation shifts to an explanation of FIG. 29. The second obtaining unit 523 sends the date and the center time of that day to the management apparatus 103, and obtains the step count that corresponds to the date and the center time from the management apparatus 103 (S2901). Here, the step count means the step count that is measured in a predetermined period that includes the center time in the date (for example, a period from 12 hours before the center time to 12 hours after the center time). When the step count is measured by the measurement apparatus 105a or the measurement apparatus 105b, the second obtaining unit 523 may also obtain the step count from the measurement apparatus 105a or the measurement apparatus 105b. The display processing apparatus 101 itself may also measure the step count. In that case, the measured step count is stored in the third data storage unit 543. Then, the second obtaining unit 523 obtains the step count from the third data storage unit 543.

The second rendering unit 521 renders the obtained or measured step count (S2903). In this example, the second rendering unit 521 renders a number that represents the step count in a predetermined position as illustrated in FIG. 2.

The second obtaining unit 523, as in S2603 in FIG. 26, obtains a sleep index (S2905). Alternatively, the second rendering unit 521 calculates a sleep index.

The second rendering unit 521 renders the sleep index (S2907). In this example, the second rendering unit 521 renders a number that represents the sleep index at a predetermined position as illustrated in FIG. 2, and also renders a graph having a semicircular shape. This graph is rendered in a color of the first hue. The number that represents the sleep index is rendered smaller than the number that represents the activity index, and the graph that represents the sleep index is also rendered smaller than the graph that represents the activity index.

The second rendering unit 521 renders the date of that day (S2909). In this example, the second rendering unit 521 renders a number that represents the date as illustrated in FIG. 2. This completes an explanation of the change processing.

The explanation will return to the explanation of FIG. 9. After the change processing ends in S907, the display processing unit 503 performs processing for displaying the main screen (S909). More specifically, the display processing unit 503 causes the display control unit 507 that controls the display device to read image data that is stored in the frame buffer 551. The display control unit 507 causes each pixel of the display device to light up according to the color code. The processing then shifts to the processing in S3001 illustrated in FIG. 30 by way of terminal A.

Figure 30:
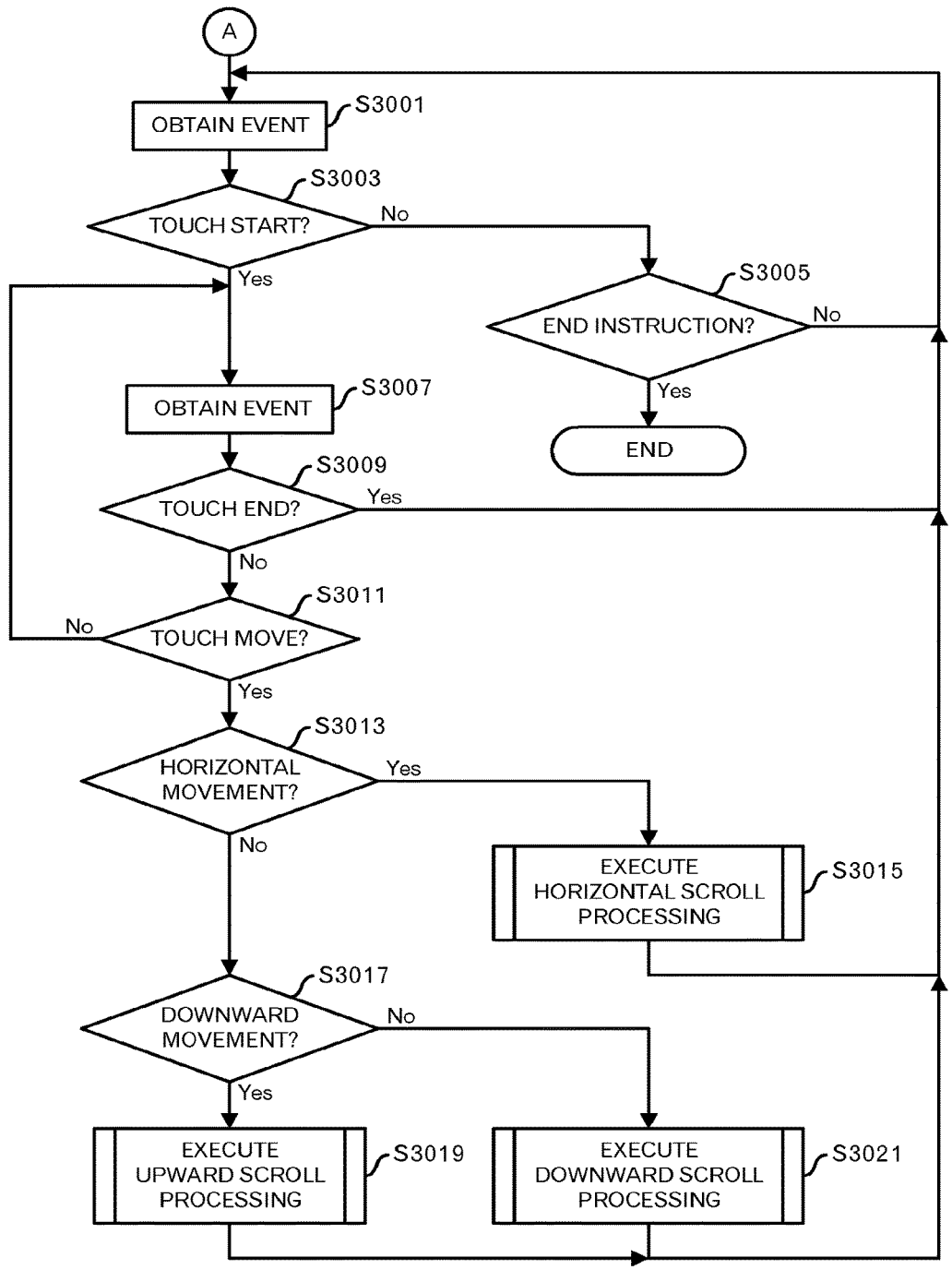
FIG. 30 is a diagram depicting an example of the main processing flow.

The explanation shifts to an explanation of FIG. 30. In the following processing, an instruction to change the target period of the graph display that is given by swiping inside the first area 203 is received. The scroll unit 525 obtains an event that occurred by user operation from the operating system 505 (S3001). In this example, an event relating mainly to the swipe operation on the touch panel is assumed. Events related to the swipe operations include a touch start, a touch move, and a touch end.

The scroll unit 525 determines whether or not the obtained event is a touch start (S3003). When it is determined that the obtained event is not a touch start, the scroll unit 525 determines whether or not the obtained event is an end instruction (S3005). When it is determined that the obtained event is an end instruction, the main processing ends. However, when it is determined that the obtained even is not an end instruction, the processing returns to S3001, and the processing described above is repeated.

In S3003, when it is determined that the event obtained in S3001 is a touch start, the scroll unit 525 obtains the event that occurred by user operation from the operating system 505 (S3007). The scroll unit 525 determines whether or not the event obtained in S3007 is a touch end (S3009). When it is determined that the event obtained in S3007 is a touch end, a swipe operation has not been performed, and the processing returns to the processing of S3001, and the processing described above is repeated.

In S3009, when it is determined that the event obtained in S3007 is not a touch end, the scroll unit 525 determines whether or not the event obtained in S3007 is a touch move (S3011). When it is determined that the event obtained in S3007 is not a touch move, the processing returns to S3007 and the scroll unit 525 obtains an event again.

However, when it is determined that the event obtained in S3007 is a touch move, the scroll unit 525 determines whether or not horizontal movement occurred at the touch position (S3013). For example, the scroll unit 525 calculates a movement vector from the position where the touch start is detected to the position where the touch move is detected. The scroll unit 525 compares the vertical component (Y-coordinate component) in that movement vector and the horizontal component (X-coordinate component). Then, when the horizontal component is greater than the vertical component, the scroll unit 525 determines that a horizontal movement occurred.

When it is determined that a horizontal movement occurred at the touch position, the scroll unit 525 executes horizontal scroll processing (S3015). The horizontal scroll processing will be described later using FIGS. 31 to 35. When the horizontal scroll processing ends, the processing returns to S3001, and the processing described above is repeated.

In S3013, where it is determined that a horizontal movement did not occur at the touch position, the scroll unit 525 determines whether or not a downward movement occurred at the touch position (S3017). When the vertical component of the movement vector is downward, or in other words, when the Y-coordinate component of the movement vector is a positive value, the scroll unit 525 determines that a downward movement occurred at the touch position. However, when the vertical component of the movement vector is upward, or in other words, when the Y-coordinate component of the movement vector is a negative value, the scroll unit 525 determines that an upward movement occurred at the touch position.

When it is determined that downward movement occurred at the touch position, the scroll unit 525 executes upward scroll processing (S3019). The upward scroll processing will be described later using FIGS. 36 to 45. When the upward scroll processing ends, the processing returns to S3001, and the processing described above is repeated.

When it is determined that a downward movement did not occur at the touch position, or in other words, when an upward movement occurred at the touch position, the scroll unit 525 executes a downward scroll processing (S3021). The downward scroll processing will be described later using FIGS. 46 to 50. When the downward scroll processing ends, the processing returns to S3001, and the processing described above is repeated.

Figure 31:
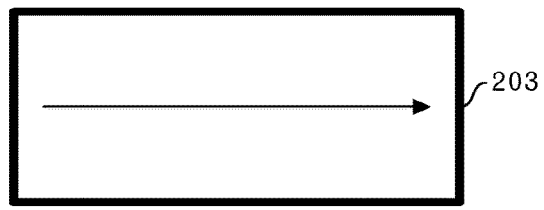
FIG. 31 is a diagram depicting an example of swiping.

Here, the horizontal scroll processing described above will be explained. FIG. 31 illustrates a state in which the user performs a swipe inside the first area 203. More specifically, FIG. 31 illustrates that the user touched a position that is indicated by the starting point of an arrow with a finger, slid the finger to the position indicated by the endpoint of the arrow while touching, and released the finger at that point. In this example, the length the finger is slid is about ⅞ of the width of the first area 203. In this example, the direction of sliding is the right direction. Therefore, this swipe corresponds to an instruction to move the target period of the display graph about 7 hours back in time.

Figure 32:
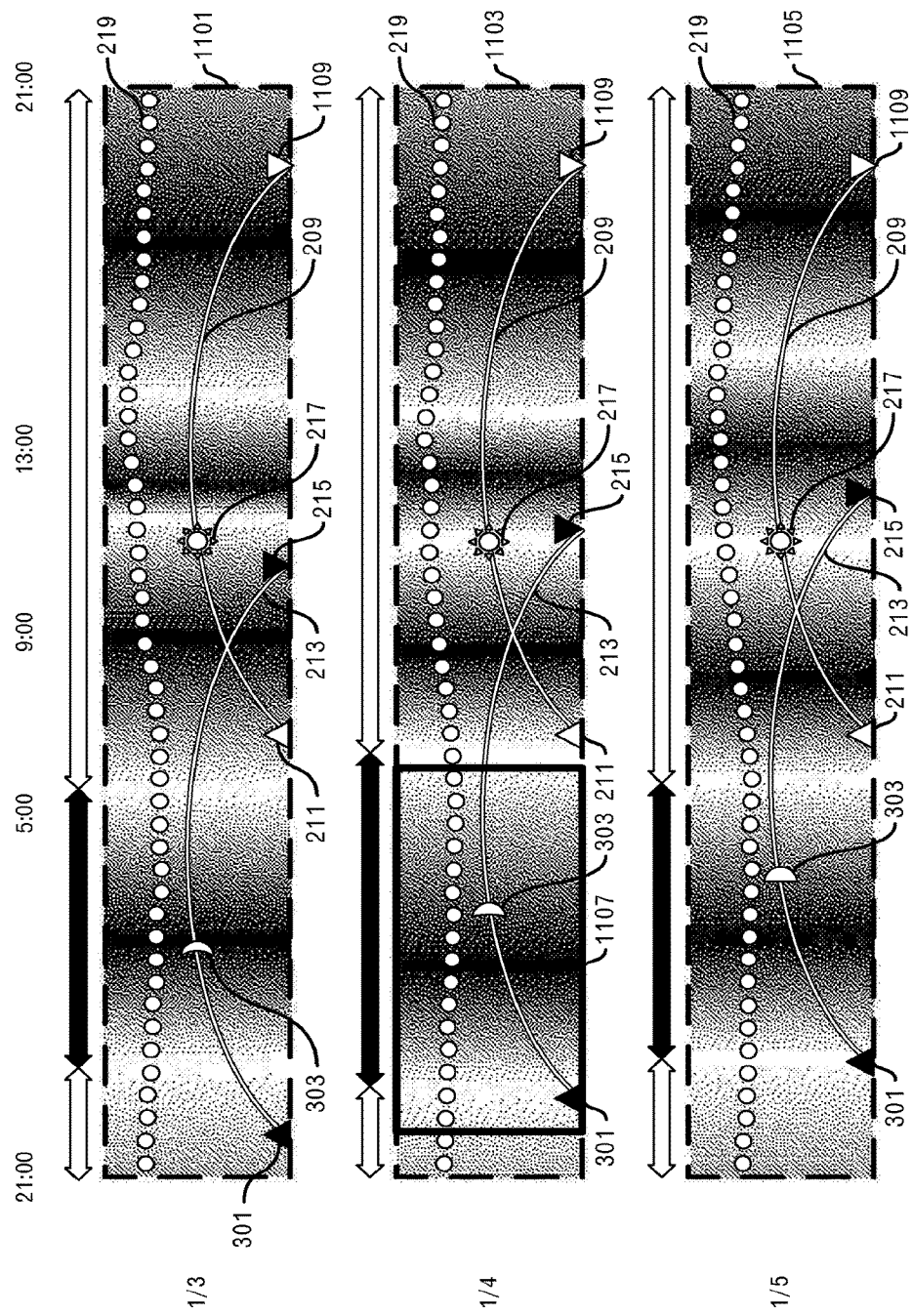
FIG. 32 is a diagram depicting an example of a copy range that is slid horizontally.

FIG. 32 illustrates an example of a copy range that is slid horizontally. FIG. 32 illustrates a state in which the copy range slides to the left when the expanded state illustrated in FIG. 11 is swiped as illustrated in FIG. 31. The copy range 1107 shifts in the left direction, in other words in a direction back in time, by a length that corresponds to about ⅞ of the copy range 1107. By the horizontal scroll processing, the graph image inside this copy range 1107 is displayed.

Figure 33:
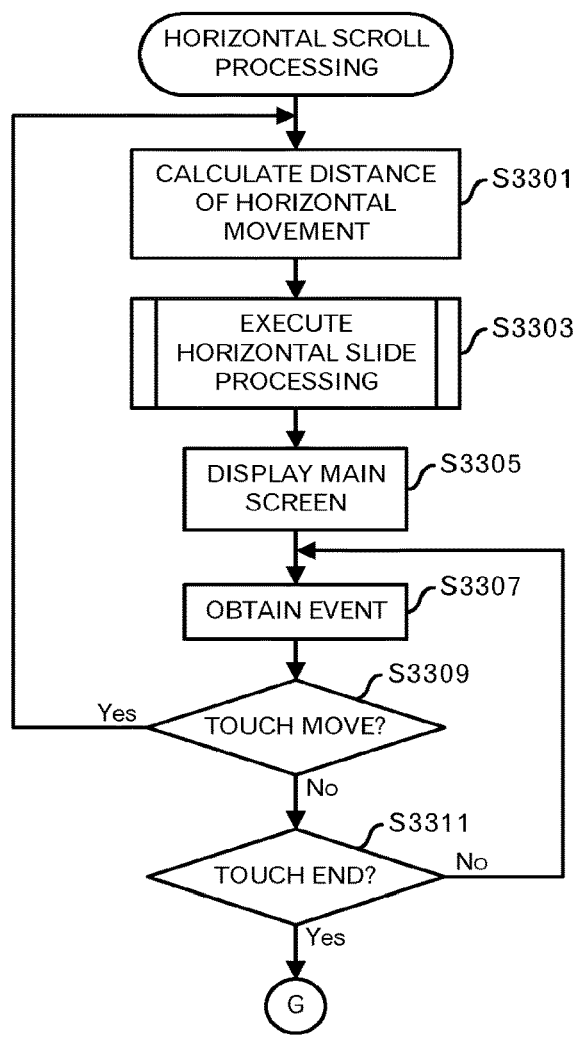
FIG. 33 is a diagram depicting an example of a horizontal scroll processing flow.

FIG. 33 illustrates an example of a horizontal scroll processing flow. The scroll unit 525 calculates the distance of horizontal movement from the touch position at the touch start to a touch position in the most recent touch move (S3301). The scroll unit 525 detects, for example, a movement vector from the previous touch position in each touch move, and finds the distance of horizontal movement by totaling the horizontal components (X-coordinate components) of those movement vectors. When the swipe is in the right direction, the distance of horizontal movement is a positive value, and when the swipe is in the left direction, the distance of horizontal movement is a negative value.

Figure 34:
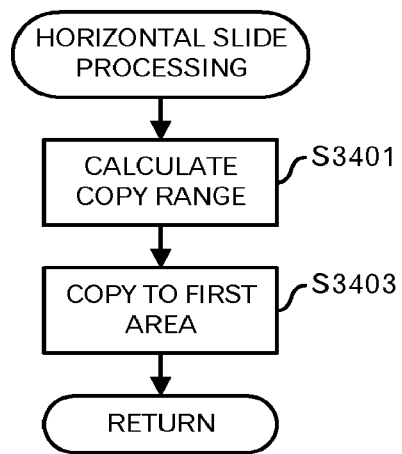
FIG. 34 is a diagram depicting an example of the horizontal slide processing flow.

The scroll unit 525 executes horizontal slide processing (S3303). FIG. 34 illustrates an example of a horizontal slide processing flow. In the horizontal slide processing, the copy range 1107 slides horizontally. The scroll unit 525 calculates a new copy range 1107 in the second graph buffer 555 (S3401). The X coordinate of the upper left end of a new copy range 1107 is found by subtracting the distance of horizontal movement from the X coordinate of the upper left end of the initial copy range 1107, or in other words, the copy range 1107 that is set in S1011 illustrated in FIG. 10. The Y coordinate of the upper left end of the new copy range 1107 is the same as the Y coordinate of the upper left end of the initial copy range 1107.

The X coordinate of the lower right end of a new copy range 1107 is found by subtracting the distance of horizontal movement from the X coordinate of the lower right end of the initial copy range 1107. The Y coordinate of the lower right end of the new copy range 1107 is the same as the Y coordinate of the lower right end of the initial copy range 1107.

The scroll unit 525 copies the image inside the new copy range 1107 in the second graph image 1103 to the first area 203 in the frame buffer 551 (S3403). When the horizontal slide processing ends, the processing shifts to the processing of S3305 illustrated in FIG. 33.

The explanation returns to the explanation of FIG. 33. The scroll unit 525 performs processing for displaying the main screen (S3305). More specifically, the processing is the same as in the case of S909 illustrated in FIG. 9.

The scroll unit 525 obtains an event that occurs by user operation from the operating system 505 (S3307). The scroll unit 525 determines whether or not the obtained event is a touch move (S3309). When it is determined that the obtained event is a touch move, the processing returns to the processing of S3301, and the processing described above is repeated.

However, when it is determined that the obtained event is not a touch move, the scroll unit 525 determines whether or not the event obtained in S3307 is a touch end (S3311). When it is determined that the event obtained in S3307 is a touch end, the processing returns to S3307 and an event is obtained again.

Figure 35:
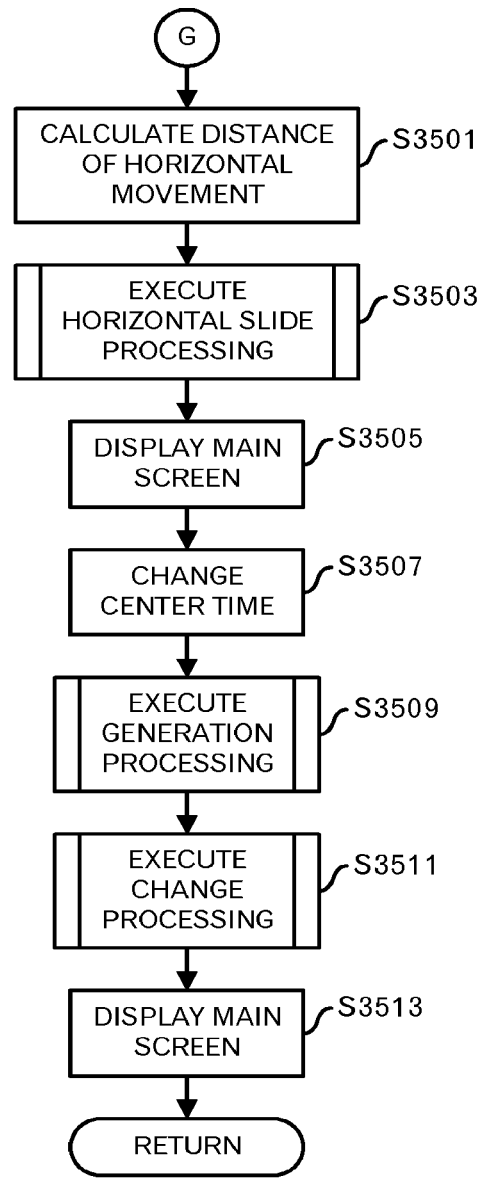
FIG. 35 is a diagram depicting an example of the horizontal scroll processing flow.

However, when it is determined that the event obtained in S3307 is a touch end, processing shifts to the processing of S3501 illustrated in FIG. 35 by way of terminal G.

The explanation will move to an explanation of FIG. 35. The processing from S3501 to S3505 is the same as the processing from S3301 to S3305 illustrated in FIG. 33. At this time, the range that is to be displayed after scrolling has already been set. Therefore, the scroll unit 525 changes the center time (S3507). A new center time is found by subtracting a time that corresponds to the distance of horizontal movement from the current center time. When the new center time exceeds a boundary of the date, the scroll unit 525 also changes the date.

The generator 511 executes the generation processing (S3509). A new first graph image 1101 is generated in the first graph buffer 553. Similarly, a new second graph image 1103 is generated in the second graph buffer 555. Similarly, a new third graph image 1105 is generated in the third graph buffer 557.

For example, the graph period after horizontal sliding as in FIG. 32 is shifted backward by 7 hours at a time. In other words, the center time of the new first graph image 1101 is January 3 2:00, and the period of the new first graph image 1101 is the period from January 2 14:00 to January 3 14:00. The center time of the new second graph image 1103 is January 4 2:00, and the period of the new second graph image 1103 is the period from January 3 14:00 to January 4 14:00. The center time of the new third graph image 1105 is January 5 2:00, and the period of the new third graph image 1105 is the period from January 4 14:00 to January 5, 14:00.

The change unit 517 executes the change processing (S3511). For the image of the second area 205, an image of a new first analysis screen or an image of a new second analysis screen is generated according to the target period of anew graph display. For example, in the case of horizontal sliding as in FIG. 32, the sleep time is dominant, and the screen is changed to the first analysis screen. The scroll unit 525 performs processing for displaying the main screen (S3513). In this way, the main screen 201 illustrated in FIG. 3 is displayed, for example. When the horizontal scroll processing is finished, the processing returns to the processing in FIG. 30, which is the calling source, and the processing shifts to the processing of S3001.

Figure 36:
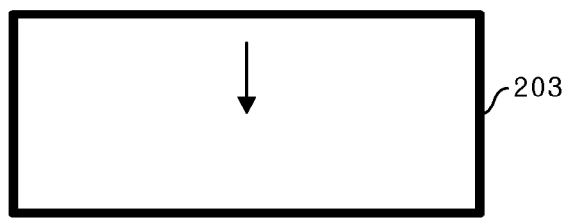
FIG. 36 is a diagram depicting an example of swiping.

Next, the aforementioned upward scroll processing will be explained. FIG. 36 illustrates a state in which the user performs swiping in the first area 203. More specifically, FIG. 36 illustrates that with a finger, the user touches a position that is indicated by the starting point of an arrow, and with the finger still touching slides the finger to the position indicated by the end point of the arrow, and at that point releases the finger. The length the finger is slid in this example is about ⅓ of the height of the first area 203. In this example, this direction of sliding is the downward. Therefore, this swipe corresponds to an instruction that causes a graph that is presumed to have a position that is located above the currently displayed graph to be displayed, or in other words, displays the lower ⅓ portion of the graph of the previous day.

Figure 37:
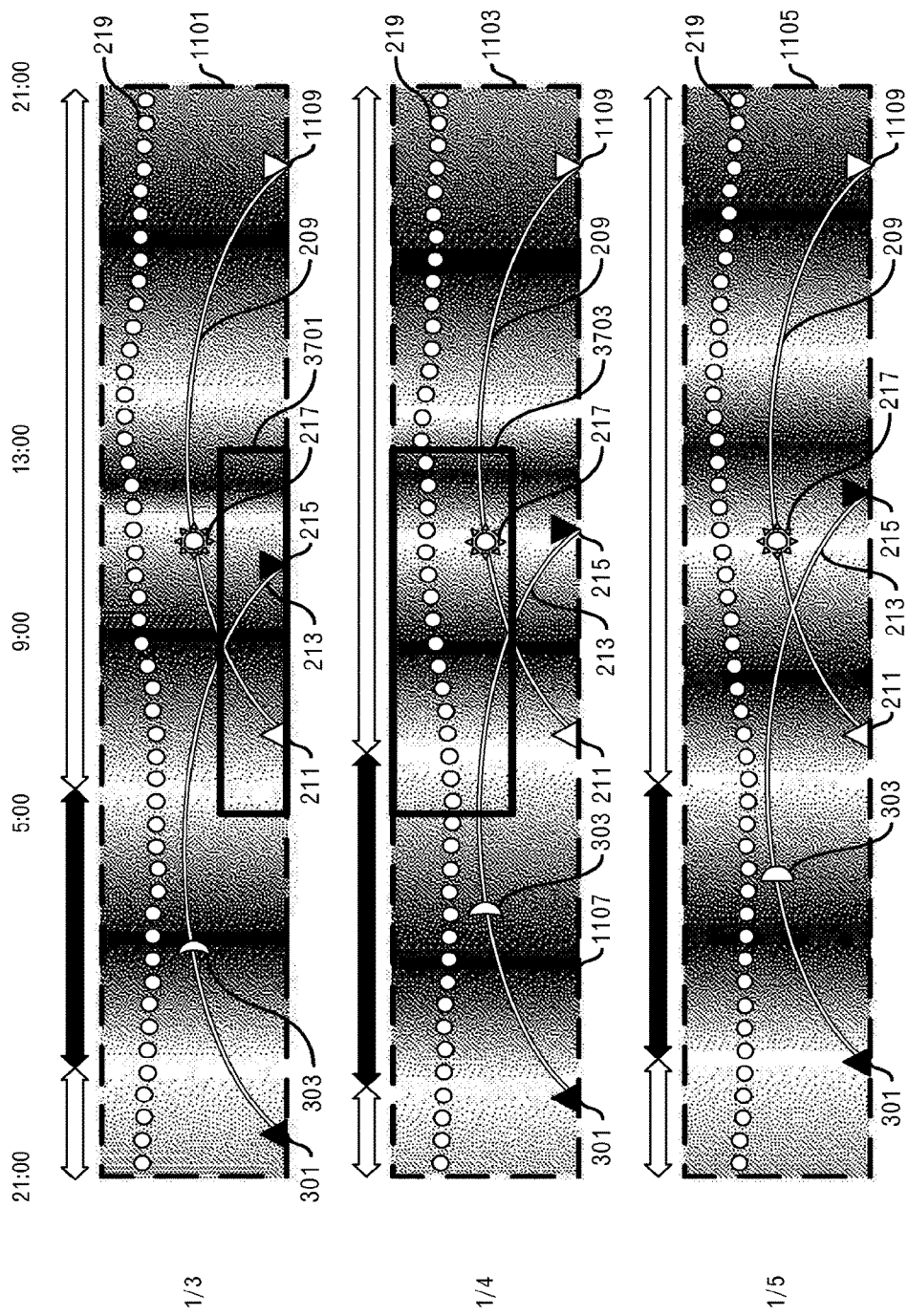
FIG. 37 is a diagram depicting an example of a divided copy range.

FIG. 37 illustrates an example of a divided copy range. FIG. 37 illustrates a state in which the copy range is divided into two parts when the swipe illustrated in FIG. 36 is performed in the expanded state illustrated in FIG. 11. The copy range 3701 represents the copy range of a first graph image 1101. The height of the copy range 3701 corresponds to the distance of the slide by a swipe. The width of the copy range 3701 is the same as the width of the copy range 1107.

The copy range 3703 represents the copy range of a second graph image 1103. The height of the copy range 3703 corresponds to the difference when subtracting the distance of the slide by the swipe from the height of the copy range 1107. The width of the copy range 3703 is the same as the width of the copy range 1107.

The image inside the copy range 3701 is rendered on the upper side of the first area 203, and the image inside the copy range 3703 is rendered on the lower side of the first area 203. However, in the examples in FIG. 36 and FIG. 37, the distance value of the slide is shorter than a threshold value (for example, half of the height of the first area 203), and the copy range 1107 returns to the initial position in the second graph image 1103. In other words, it returns to a state in which the graph of that day is displayed state in the first area 203 without performing an upward scroll.

Figure 38:
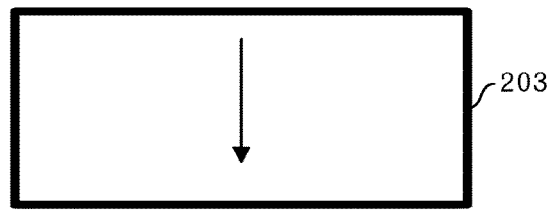
FIG. 38 is a diagram depicting an example of swiping.

FIG. 38 illustrates the state of another swipe. The slide direction in this example is downward as well. However, the slide length in this example is about ⅔ of the height of the first area 203. Therefore, this swipe corresponds to an instruction for displaying a graph that is presumed to have a position above the graph that is currently displayed, or in other words, an instruction for displaying the lower ⅔ portion of the graph of the previous day.

Figure 39:
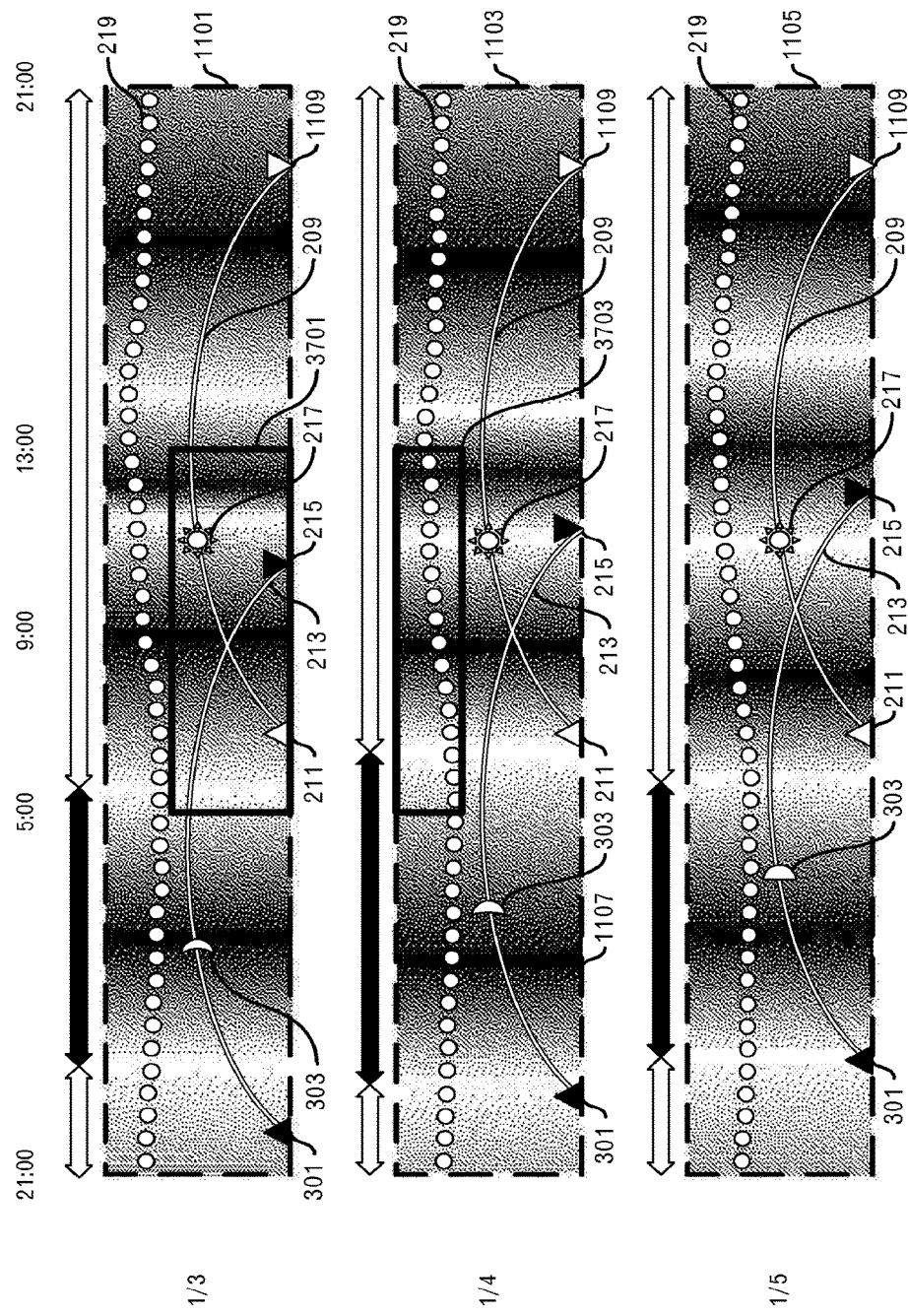
FIG. 39 is a diagram depicting an example of the divided copy range.

FIG. 39 illustrates a state in which the copy range is divided into two parts when the swiping illustrated in FIG. 38 is performed in the expanded state illustrated in FIG. 11. As was described above, the image in the copy range 3701 is rendered on the upper side of the first area 203, and the image inside the copy area 3703 is rendered on the lower side of the of the first area 203. However, in the examples in FIG. 38 and FIG. 39, since the slide distance is longer than the threshold value (half of the height of the first area 203, for example), upward scrolling is performed and the graph is switched to the graph of the previous day.

Figure 40:
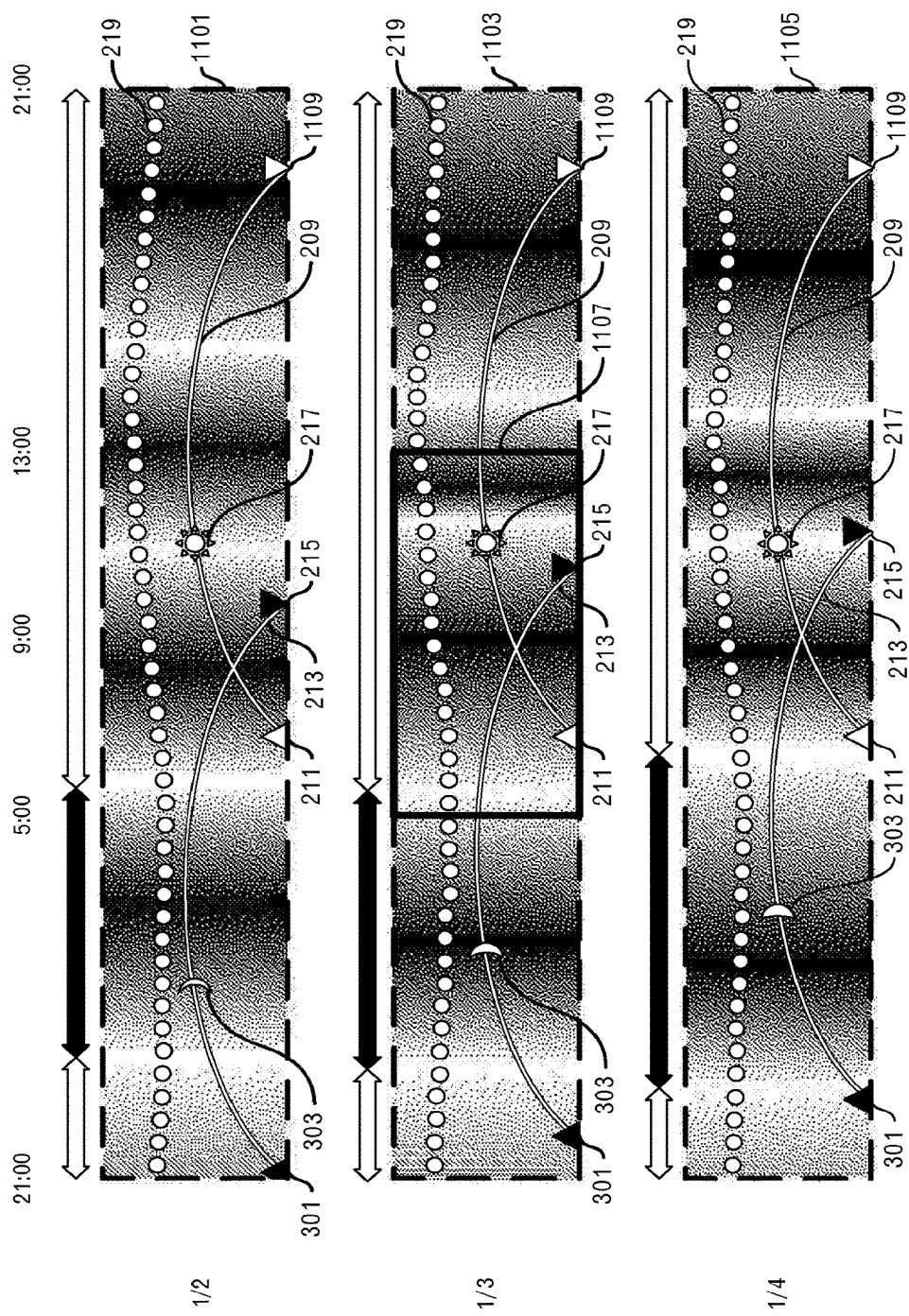
FIG. 40 is a diagram depicting an example of a copy range after an upward scroll.

FIG. 40 illustrates an example of a copy range after the upward scrolling. The assignment of date changes depending on the upward scrolling. Each date is shifted backward. The date of that day changes from January 4 to January 3, and the date of the previous day changes from January 3 to January 2, and the date of the next day changes from January 5 to January 4. Moreover, the first graph image 1101 to third graph image 1105 also change.

Then, the copy range 1107 is set in the initial position of the second graph image 1103. In this way, the graph of the previous day before scrolling is displayed after scrolling as the graph of that day.

Figure 41:
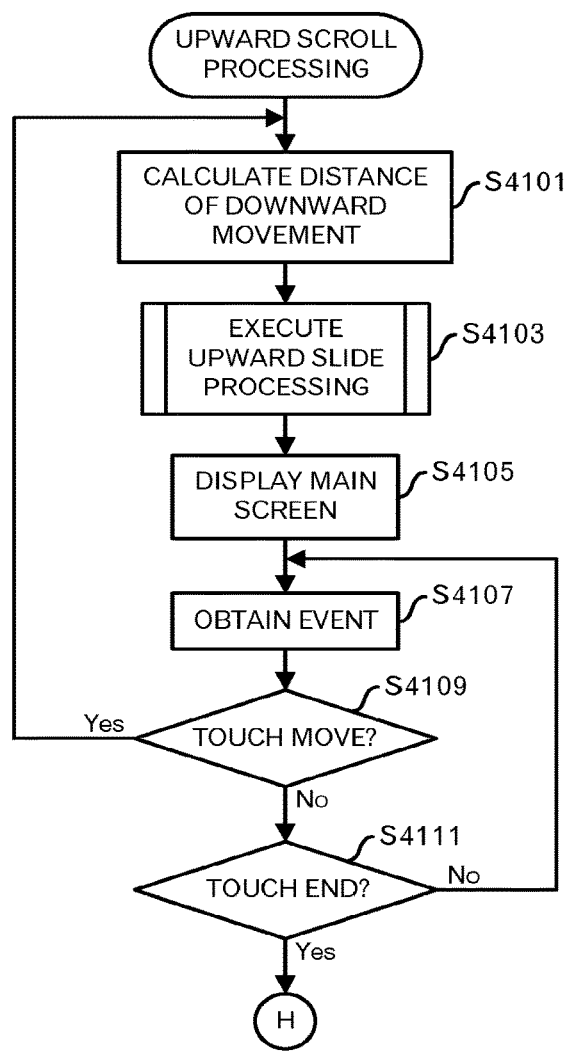
FIG. 41 is a diagram depicting an example of an upward scroll processing flow.

FIG. 41 illustrates an example of an upward scroll processing flow. The scroll unit 525 calculates a distance of downward movement from the touch position of a touch start to the touch position in the most recent touch move (S4101). The scroll unit 525 finds the distance of downward movement, for example, by detecting movement vectors from the previous touch positions in each of the touch moves, and finds a total of the vertical components (Y-coordinate components) of those movement vectors. The distance of downward movement is a positive value.

Figure 42:
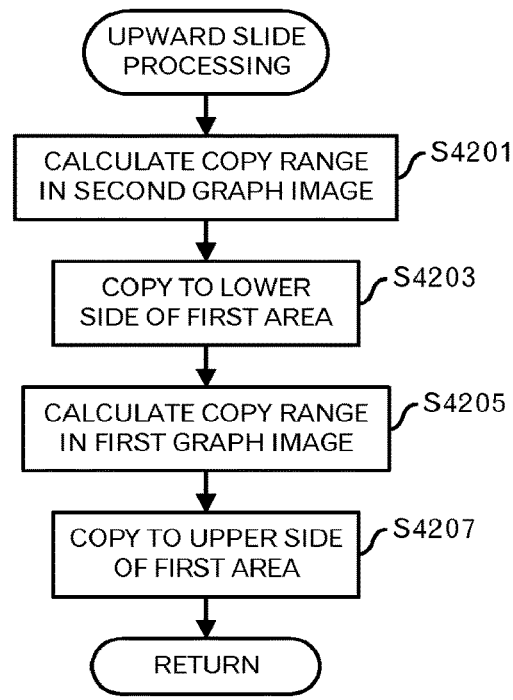
FIG. 42 is a diagram depicting an example of an upward slide processing flow.

The scroll unit 525 executes the upward slide processing (S4103). FIG. 42 illustrates an example of a upward slide processing flow. In the upward slide processing, it is presumed that the graph of the previous day is expanded in the upper part in the first area 203.

The scroll unit 525 calculates a new copy range in the second graph image 1103 (S4201). The X coordinate and Y coordinate of the upper-left end of the new copy range are the same as the X coordinate and Y coordinate of the upper-left end of the initial copy range, or in other words, the same as those of the copy range set in S1011 illustrated in FIG. 10.

The X coordinate of the lower-right end of the new copy range is the same as the X coordinate of the lower-right end of the initial copy range. The Y coordinate of the lower-right end of the new copy range is found by subtracting the distance of downward movement from the Y coordinate of the lower-right end of the initial copy range.

The scroll unit 525 copies the image inside the new copy range 3703 in the second graph image 1103 to the lower side of the first area 203 of the frame buffer 551 (S4203).

Next, the scroll unit 525 calculates a copy range in the first graph image 1101 (S4205). The X coordinate of the upper-left end of the copy range in the first graph image 1101 is the same as the X coordinate of the upper-left end of the initial copy range in the second graph 1103. The Y coordinate of the upper-left end of the copy range in the first graph image 1101 is found by subtracting the distance of downward movement from the Y coordinate of the lower-right end in the initial copy range in the second graph image 1103.

The X coordinate and Y coordinate of the lower right end of the copy range in the first graph image 1101 are the same as the X coordinate and Y coordinate of the lower-right end of the initial copy range, or in other words, the copy range that is set in S1011 illustrated in FIG. 10.

The scroll unit 525 copies the image inside the copy range 3701 in the first graph image 1101 to the upper side of the first area 203 in the frame buffer 551 (S4207). After upward slide processing ends, the processing shifts to the processing of S4105 illustrated in FIG. 41.

The explanation returns to the explanation of FIG. 41. The scroll unit 525 performs processing to display the main screen (S4105). The detailed processing is the same as that in S909 illustrated in FIG. 9.

The scroll unit 525 obtains an event that occurred due to user operation from the operating system 505 (S4107). The scroll unit 525 determines whether or not the obtained event is a touch move (S4109). When it is determined that the obtained event is a touch move, the processing returns to the processing of S4101 and the processing described above is repeated.

However, when it is determined that the obtained event is not a touch move, the scroll unit 525 determines whether or not the event obtained in S4107 is a touch end (S4111). When it is determined that the event obtained in S4107 is not a touch end, the processing returns to S4107, and an event is obtained again.

Figure 43:
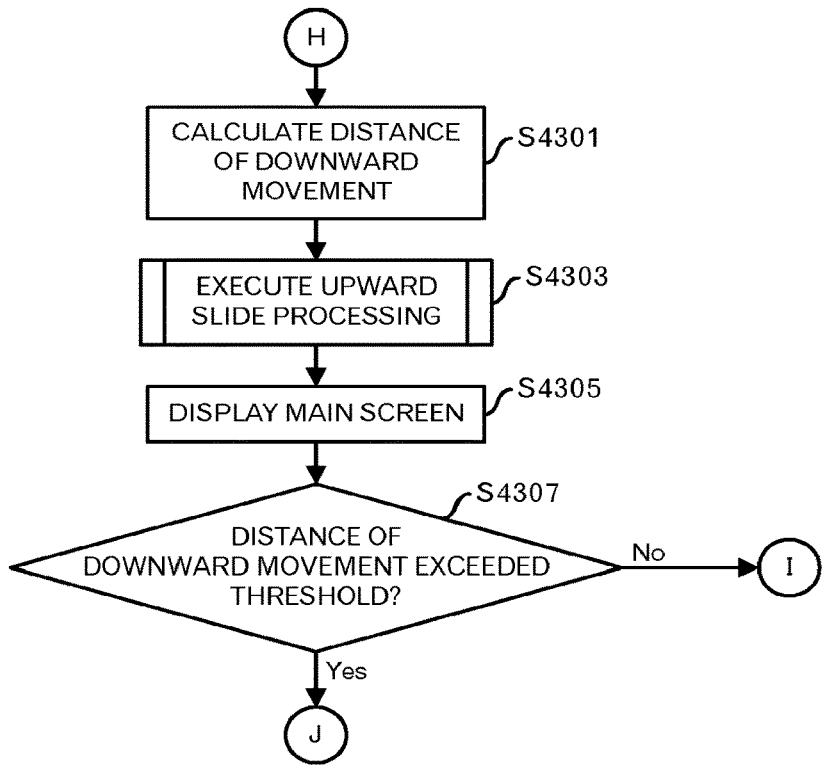
FIG. 43 is a diagram depicting an example of the upward scroll processing flow.

However, when the event obtained in S4111 is a touch end, the processing shifts to the processing of S4301 illustrated in FIG. 43 by way of terminal H.

The explanation shifts to an explanation of FIG. 43. The processing from S4301 to S4305 is the same as the processing from S4101 to S4105 illustrated in FIG. 41.

The scroll unit 525 determines whether or not the distance of downward movement exceeds a threshold value (S4307). The threshold value is a value obtained by multiplying the height of the first area 203 by a predetermined ratio. The predetermined ratio is a value that is greater than 0 but less than 1. For example, when the predetermined ratio is 0.5, and swiping is performed just a distance that exceeds half the height of the first area 203, the graph is controlled to be shifted to that of the previous day. However, when swiping is performed a distance that is equal to or less than the half the height of the first area 203, the graph is controlled not to be shifted to that of the previous day.

Figure 44:
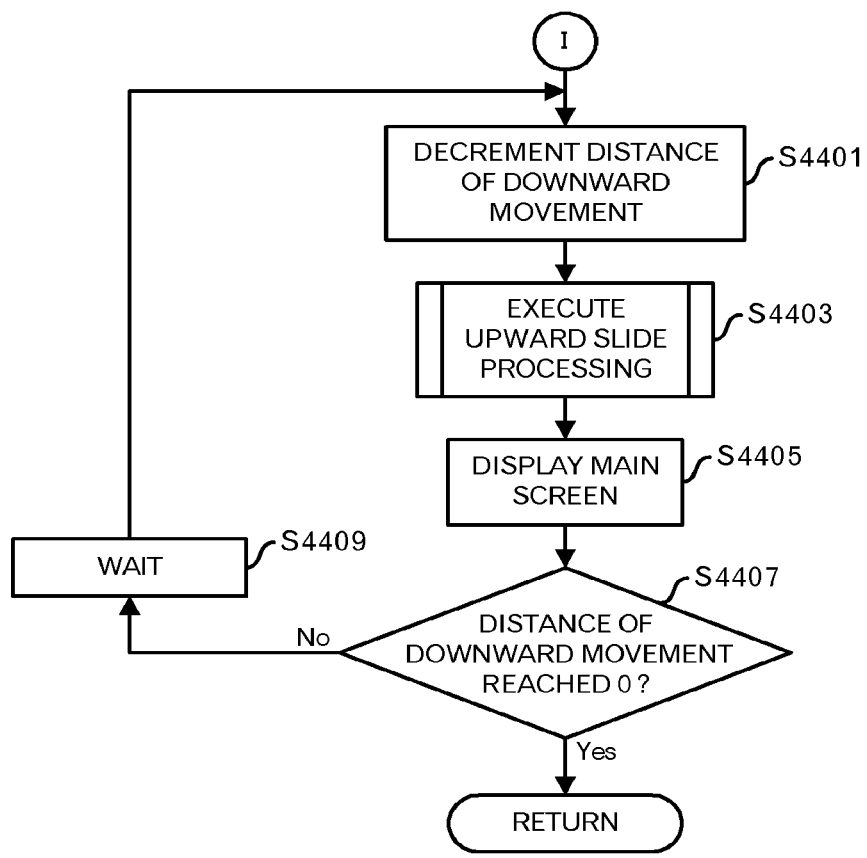
FIG. 44 is a diagram depicting an example of the upward scroll processing flow.

When it is determined that the distance of downward movement does not exceed the threshold value, the processing shifts to the processing of S4401 illustrated in FIG. 44 by way of terminal I. However, when it is determined that the distance of downward movement exceeds the threshold value, the processing shifts to the processing of S4501 illustrated in FIG. 45 by way of terminal J.

First, the processing illustrated in FIG. 44 will be explained. In the processing illustrated in FIG. 44, the display range that is slid upward automatically returns to the original position. Therefore, the screen is redisplayed while gradually reducing the distance of downward movement calculated in S4301.

The scroll unit 525 decrements the distance of downward movement (S4401). For example, the scroll unit 525 subtracts a predetermined length from the distance of downward movement to make the value of the distance of downward movement close to 0. Then, the scroll unit 525 executes the upward slide processing (S4403), and displays the main screen (S4405).

The scroll unit 525 determines whether or not the distance of downward movement has reached 0 (S4407). When it is determined that the distance of downward movement has not reached 0, the scroll unit 525 waits just a predetermined amount of time (S4409), and then the processing returns to S4401. The predetermined length in S4401 and the predetermined amount of time in S4409 are set, for example, so that the user feels that the screen flow is smooth.

However, when it is determined that the distance of downward movement has reached 0, the upward scroll processing ends. In this way, the graph returns to the state before the upward scroll processing started. Then, processing returns to the processing of the calling source in FIG. 30, and shifts to the processing of S3001.

Figure 45:
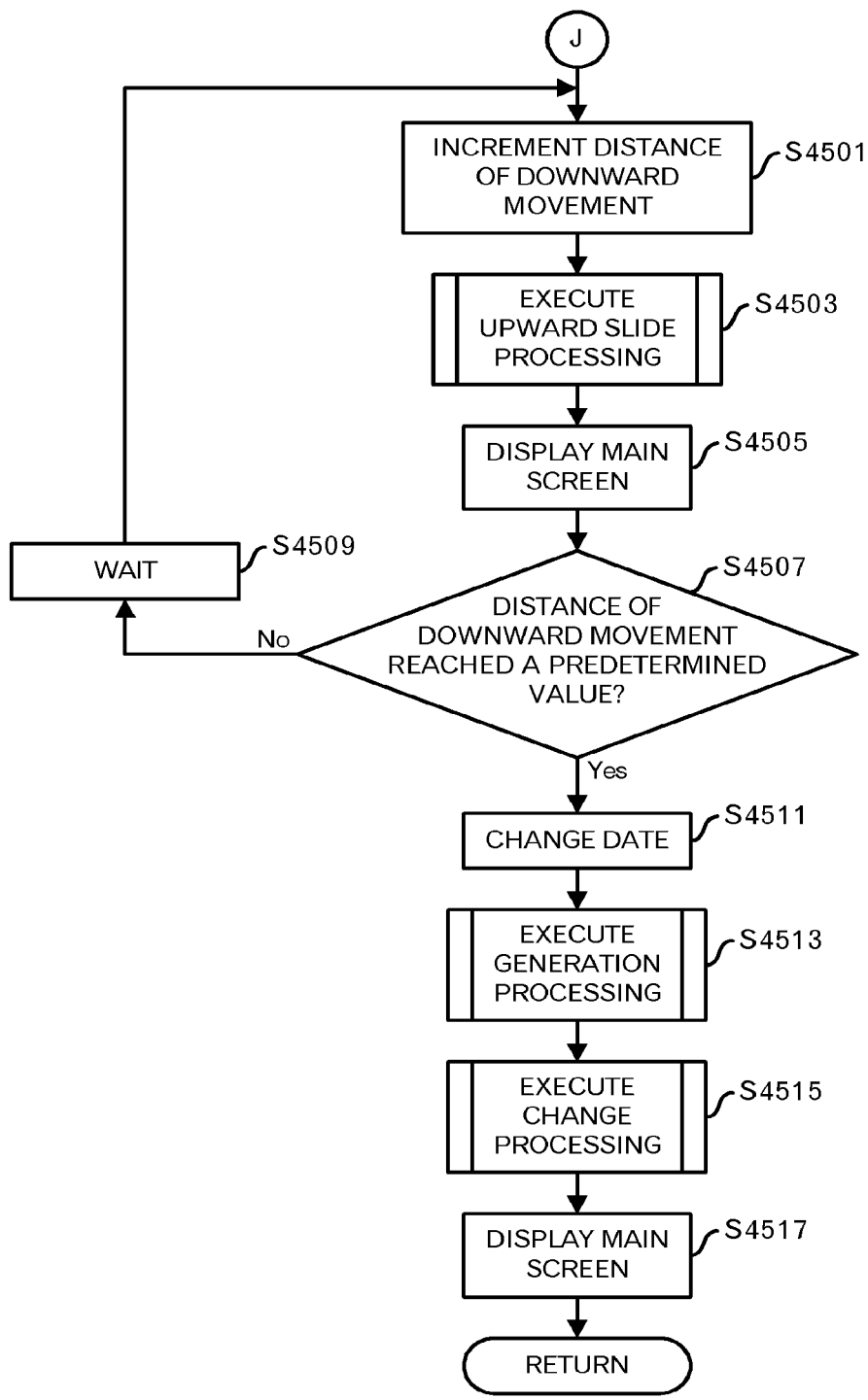
FIG. 45 is a diagram depicting an example of the upward scroll processing flow.

Next, the processing illustrated in FIG. 45 will be explained. In the processing illustrated in FIG. 45, the displayed range is automatically slid upward, and is shifted to the graph of the previous day. Therefore, the screen is redisplayed while gradually increasing the distance of downward movement calculated in S4101.

The scroll unit 525 increments the distance of downward movement (S4501). For example, the scroll unit 525 adds a predetermined length to the distance of downward movement to make the distance of downward movement close to a predetermined value. The predetermined value is set so that the display screen is slid to where the user can check a large portion of the graph of the previous day. Therefore, the predetermined value is a value that is equal to the height L of the first area 203, or is a value near the height L of the first area 203. The scroll unit 525 then executes the upward slide processing (S4503) and displays the main screen (S4505).

The scroll unit 525 determines whether or not the distance of downward movement has reached a predetermined value (S4507). When it is determined that the distance of downward movement has not reached a predetermined value, the scroll unit 525 waits for just a predetermined amount of time (S4509), and then the processing returns to the processing of S4501. The predetermined length in S4501 and the predetermined amount of time in S4509 are set, for example, so that the user feels that the flow of the screen is smooth.

However, when it is determined that the distance of downward movement has reach a predetermined value, the scroll unit 525 changes the dates that correspond to the previous day, that day and the next day (S4511). In other words, the each of the dates for the previous day, that day and the next day are shifted back one day. However, the center time is not changed.

The generator 511 executes the generation processing (S4513). By the generation processing, a new first graph image 1101 is expanded in the first graph buffer 553 according to the new date. Similarly, a new second graph image 1103 is expanded in the second graph buffer 555. Similarly, a new third graph image 1105 is expanded in the third graph buffer 557. The change unit 517 executes the change processing (S4515). The scroll unit 525 displays the main screen (S4517). By doing so, the main screen illustrated in FIG. 4 is displayed, for example. When the upward scroll processing ends, the processing returns to the processing of the calling source in FIG. 30, and shifts to the processing of S3001.

Next, the downward scroll processing mentioned above will be explained. In the downward scroll processing, the relationship and slide direction of the graph image is vertically reversed from that in the upward scroll processing, and the date is shifted forward. The basic idea is the same as in the upward scroll processing, and the processing will be simply described here.

Figure 46:
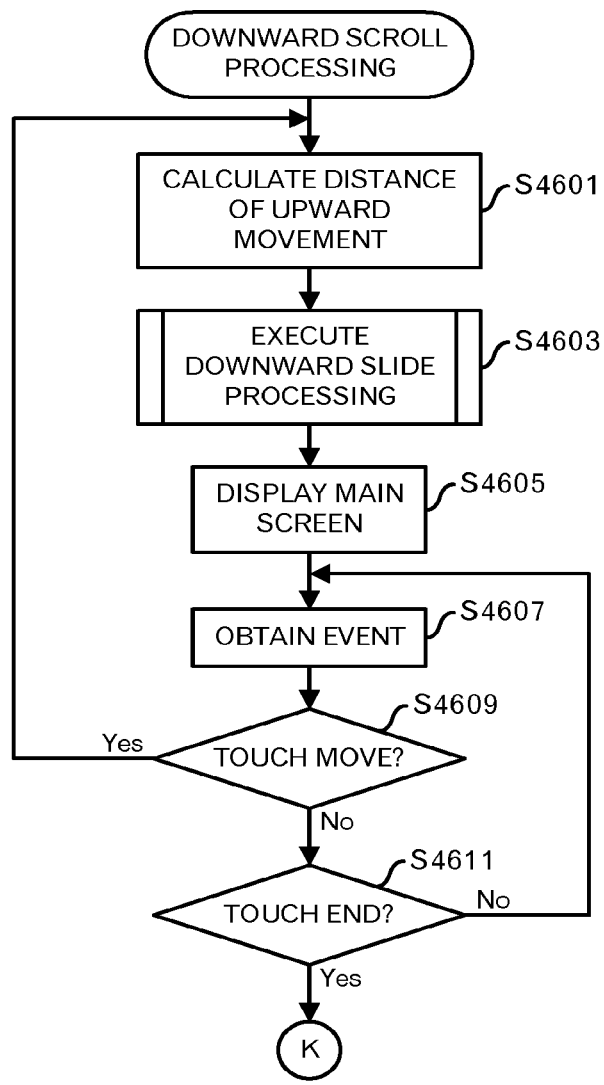
FIG. 46 is a diagram depicting an example of a downward scroll processing flow.

FIG. 46 illustrates an example of a downward scroll processing flow. The scroll unit 525 calculates the distance of upward movement from a touch position at a touch start to a touch position of the most recent touch move (S4601). The scroll unit 525 detects, for example, a movement vector from the previous touch position in each touch move, and finds the distance of upward movement by totaling the vertical components (Y-coordinate components) of those movement vectors. The distance of upward movement is a negative value.

Figure 47:
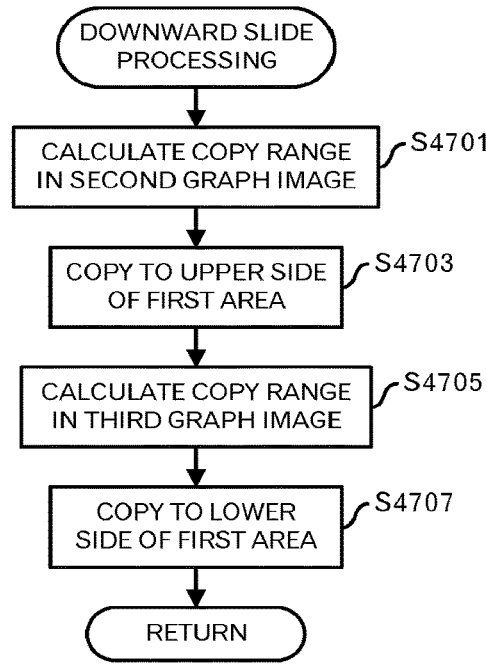
FIG. 47 is a diagram depicting an example of a downward slide processing flow.

The scroll unit 525 executes downward slide processing (S4603). FIG. 47 illustrates an example of the downward slide processing. The scroll unit 525 calculates anew copy range in the second graph image 1103 (S4701). The X coordinate of the upper-left end of the copy range is the same as the X coordinate of the lower-left end of the initial copy range. The Y coordinate of the upper-left end of the copy range is found by subtracting from the Y coordinate of the upper-left end of the initial copy range the distance of upward movement.

The X coordinate of the lower-right end of the copy range is the same as the X coordinate of the lower-right end of the initial copy range. The Y coordinate of the lower-right end of the copy range is the same as the Y coordinate of the lower-right end of the initial copy range.

The scroll unit 525 copies the image in the copy range in the second graph image 1103 to the upper side of the first area 203 in the frame buffer 551 (S4703).

The scroll unit 525 calculates the copy range in the third graph image 1105 (S4705). The X coordinate of the upper-left end of the copy range in the third graph image 1105 is the same as the X coordinate of the lower-left end of the initial copy range in the second graph image 1103. The Y coordinate of the upper-left end of the copy range in the third graph image 1105 is the same as the Y coordinate of the upper-left end of the initial copy range in the second graph image 1103.

The X coordinate of the lower-right end of the copy range in the third graph image 1105 is the same as the X coordinate of the lower-right end of the initial copy range in the second graph image 1103. The Y coordinate of the lower-right end of the copy range in the third graph image 1105 is found by subtracting from the Y coordinate of the upper-right end of the initial copy range in the second graph image 1103 the distance of upward movement.

The scroll unit 525 copies the image in the copy range in the third graph image 1105 to the lower side of the first area 203 in the frame buffer 551 (S4707).

The explanation will return to the explanation of FIG. 46. The scroll unit 525 performs processing for displaying a main screen (S4605). The detailed processing is the same as in the case of 5909 illustrated in FIG. 9.

The scroll unit 525 obtains an event that occurred due to user operation from the operating system 505 (S4607). The scroll unit 525 determines whether or not the obtained event is a touch move (S4609). When it is determined that the obtained event is a touch move, the processing returns to the processing of 54601, and the processing described above is repeated.

However, when it is determined that the obtained event is not a touch move, the scroll unit 525 determines whether or not the event obtained in S4607 is a touch end (S4611). When it is determined that the event obtained in S4607 is not a touch end, the processing returns to S4607, and an event is obtained again.

Figure 48:
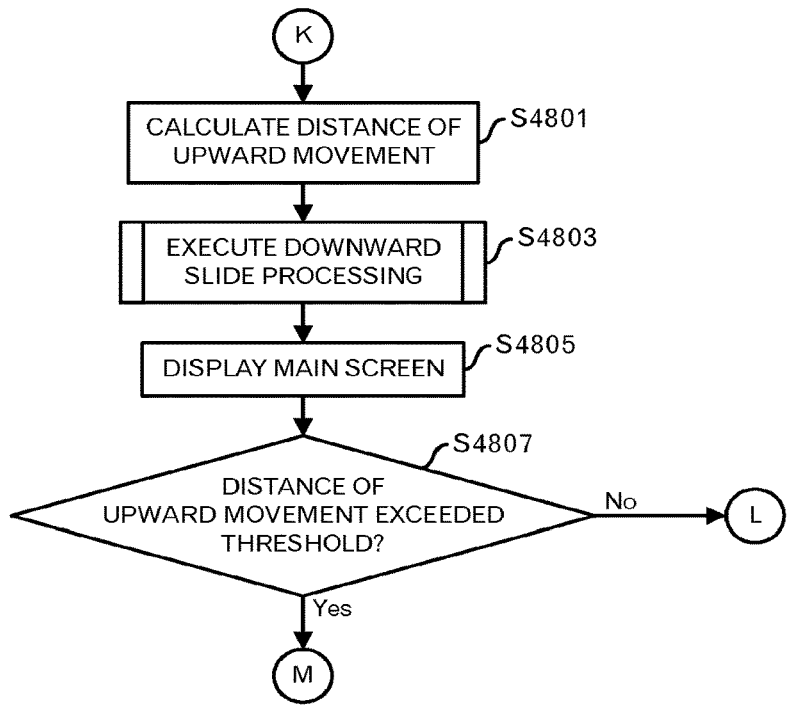
FIG. 48 is a diagram depicting an example of the downward scroll processing flow.

However, when it is determined that the event obtained in S4607 is a touch end, the processing shifts to the processing of S4801 illustrated in FIG. 48 by way of terminal K.

The explanation shifts to an explanation of FIG. 48. The processing from S4801 to S4805 is the same as the processing from S4601 to S4605 illustrated in FIG. 46.

The scroll unit 525 determines whether or not the distance of upward movement exceeds a threshold value (S4807). The threshold value is a value obtained by multiplying the height of the first area 203 by a predetermined ratio. The predetermined ratio is a value that is greater than 0 and less than 1. For example, when the predetermined ratio is 0.5 and swiping is performed for a distance that exceeds half of the height of the first area 203, it is controlled to be shift to the next day. However, when swiping is performed for a distance that is equal to or less than half of the height of the first area 203, it is controlled not to be shift to the next day.

Figure 49:
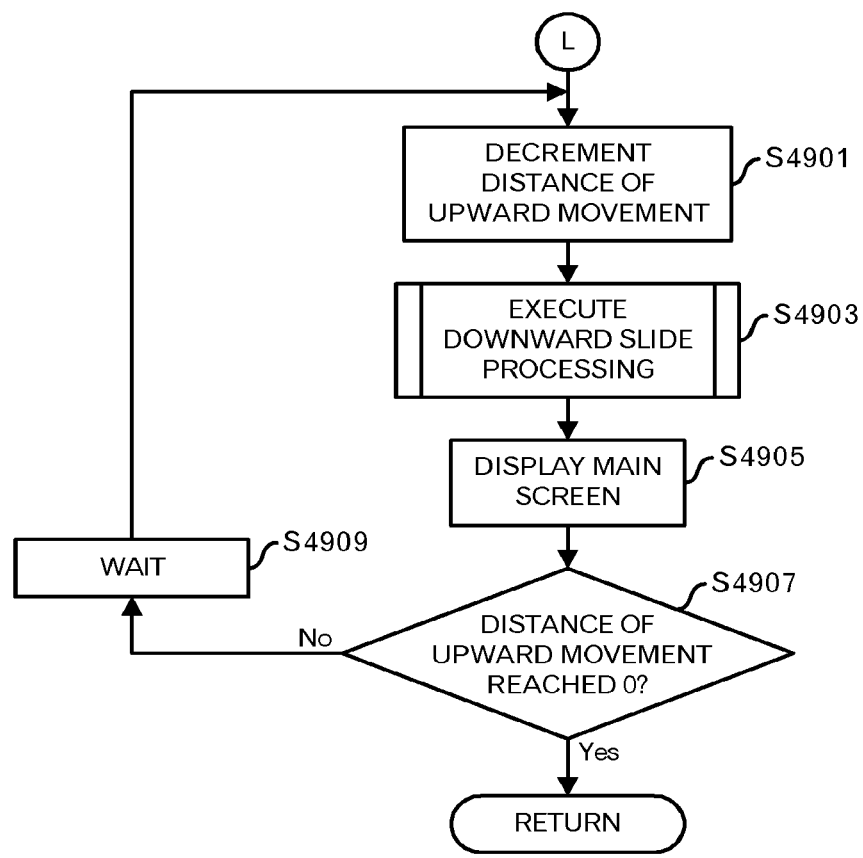
FIG. 49 is a diagram depicting an example of the downward scroll processing flow.

When it is determined that the distance of upward movement does not exceed a threshold value, the processing shifts to the processing of S4901 illustrated in FIG. 49 by way of terminal L. However, when it is determined that the distance of upward movement exceeds the threshold value, the processing shifts to the processing of S5001 illustrated in FIG. 50 by way of the terminal M.

First, the processing illustrated in FIG. 49 will be explained. In the processing illustrated in FIG. 49, the display range that is slid downward is automatically returned to the original position. Therefore, the screen is displayed again while gradually reducing the distance of upward movement that was calculated in S4801.

The scroll unit 525 decrements the distance of upward movement (S4901). For example, the scroll unit 525 subtracts a predetermined length from the distance of upward movement and makes the distance of upward movement to be toward zero. Then, the scroll unit 525 executes downward slide processing (S4903), and displays the main screen (S4905).

The scroll unit 525 determines whether or not the distance of upward movement has reached zero (S4907). When it is determined that the distance of upward movement has not reached zero, the scroll unit 525 waits a predetermined amount of time (S4909), then the processing returns to the processing of S4901. The predetermined length in S4901 and the predetermined amount of time in S4909 are set so that the user feels that the flow of the screen is smooth.

However, when it is determined that the distance of upward movement has reached zero, the downward scroll processing ends. By doing so, the graph returns to the state before beginning the downward scroll processing. Then, the processing returns to the processing of the calling source in FIG. 30, and shifts to the processing of S3001.

Figure 50:
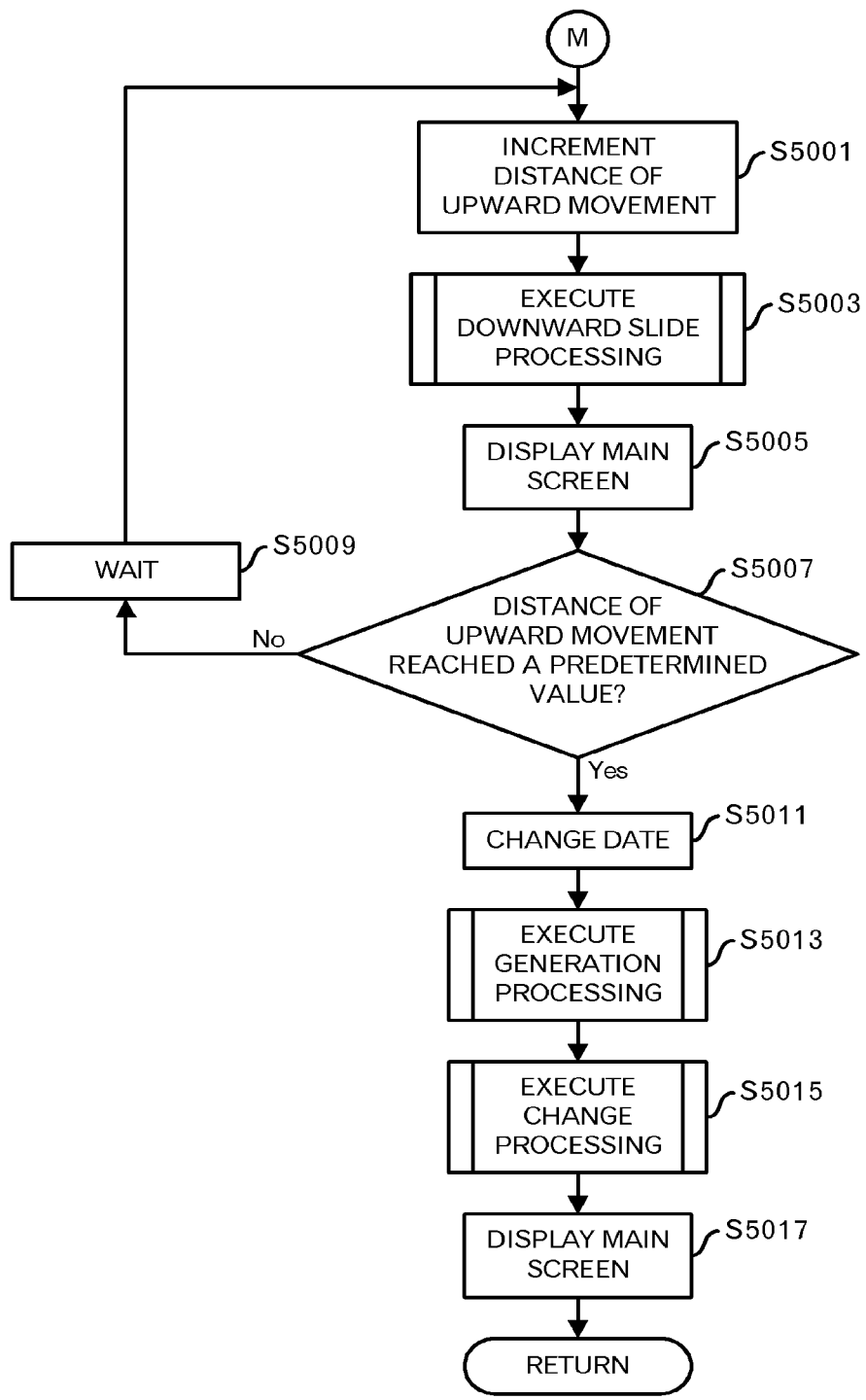
FIG. 50 is a diagram depicting an example of the downward scroll processing flow.

Next, the processing illustrated in FIG. 50 will be explained. In the processing illustrated in FIG. 50, the display range is automatically slid downward, and shifts to the graph of the next day. Therefore, the screen is displayed again while gradually increasing the distance of upward movement that was calculated in S4601.

The scroll unit 525 increments the distance of upward movement (S5001). The scroll unit 525 adds a predetermined length to the distance of upward movement, for example, and makes the distance of upward movement closer to a predetermined value. The predetermined value is set so that the display screen is slid to a position where a large portion of the next day can be checked by the user, for example. Therefore, the predetermined value is a value equal to the height L of the first area 203, or is a value near the height L of the first area 203. The scroll unit 525 then executes downward slide processing (S5003), and displays the main screen (S5005).

The scroll unit 525 determines whether or not the distance of upward movement has reached a predetermined value (S5007). When it is determined that the distance of upward movement has not reached a predetermined value, the scroll unit 525 waits a predetermined amount of time (S5009), and the processing returns to the processing of S5001. The predetermined length in S5001 and the predetermined amount of time in S5009 are set, for example, so that the user feels that the flow of the screen is smooth.

However, when it is determined that the distance of upward movement has reached a predetermined value, the scroll unit 525 changes the dates that correspond to the previous day, that day and the next day (S5011). In other words, dates that have elapsed one day only are assigned to each of the previous day, that day and the next day. However, the center time is not changed.

The generator 511 executes the generation processing (S5013). By the generation processing, a new first graph image 1101 is expanded in the first graph buffer 553 according to the new dates. Similarly, a new second graph image 1103 is expanded in the second graph buffer 555. Similarly, a new third graph image 1105 is expanded in the third graph buffer 557. The change unit 517 executes the change processing (S5015). The scroll unit 525 displays the main screen (S5017). When the downward scroll processing ends, the processing returns to the processing of the calling source in FIG. 30, and shifts to the processing of S3001.

By this embodiment, it is possible to provide a user with information that is suitable for the dominant state among the sleep state and non-sleep state.

Moreover, it is possible to provide information related to items according to the dominant state.

Furthermore, the user is able to intuitively know which of the sleep state and the non-sleep state is dominant.

Furthermore, the user is also able to know the non-sleep state other than the sleep state.

Furthermore, by performing a touch operation of the first area 203, the user is able to intuitively give an instruction to change the period.

Moreover, by this embodiment, the depth of sleep and the amount of activity (intensity of activity) is displayed as a series of states, and the user is able to chronologically know the relationship between the depth of sleep and the amount of activity (intensity of activity). Furthermore, the depth of sleep and the amount of activity (intensity of activity) are represented by the shading of colors that correspond to the sleep state and the non-sleep state, and it is easy to sensually know the transition of states that include switching between the sleep state and the non-sleep state.

Furthermore, it is helpful when considering the effect of the movement of the moon and the sun on a vital activity. For example, it is possible to know the time zone during which the sun shines, and it is helpful in considering the effect of sunlight on a vital activity. Moreover, the time zone during which the moon shines can be grasped, and it is helpful in considering the effect of moonlight on a vital activity.

Furthermore, it is helpful when considering the effect of the age of the moon on a vital activity.

Moreover, it is helpful when considering the effect of the change in temperature on a vital activity.

[Embodiment 2]

In the first embodiment, an example is given in which a state other than the sleep state is set as a non-sleep state, however, in this second embodiment, an example is given in which a state that is an awake state is set as a non-sleep state.

In the second embodiment, in S1307 illustrated in FIG. 13, determination processing (B) is executed instead of the determination processing (A) illustrated in FIG. 15.

Figure 51:
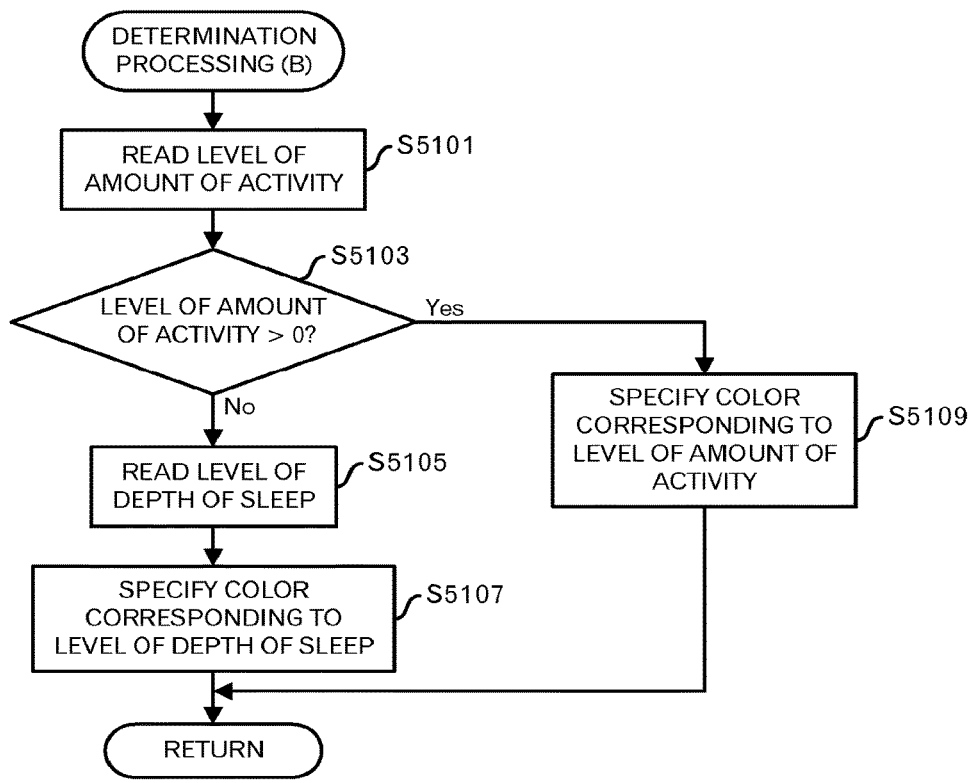
FIG. 51 is a diagram depicting an example of a determination processing (B) flow.

FIG. 51 illustrates an example of the flow of the determination processing (B). The first rendering unit 515 reads the level of the amount of activity that correspond to the measurement time zone that is specified in S1303 or S1315 illustrated in FIG. 13 from second data that is stored in the second data storage unit 533 (S5101).

The first rendering unit 515 determines whether or not the level of the amount of activity is greater than 0 (S5103). When it is determined that the level of the amount of activity is not greater than 0, or in other words, when the level of the amount of activity is 0, the first rendering unit 515 reads the level of the depth of sleep that corresponds to the measurement time zone that is specified in S1303 or S1315 illustrated in FIG. 13 from the first data that is stored in the first data storage unit 531 (S5105). The first rendering unit 515 specifies a color code that corresponds to the read level of the depth of sleep based on color data that is stored in the color data storage unit 537 (S5107). The color codes that are associated with each level of depth of sleep are the same as in the first embodiment.

However, when it is determined that the level of the amount of activity is greater than 0, the first rendering unit 515 specifies a color code that corresponds to that level of the amount of activity based on color data that is stored in the color data storage unit 537 (S5109). The color codes that are associated with each level of amount of activity are the same as in the first embodiment.

Moreover, in this second embodiment, in S2301 illustrated in FIG. 23, judgement processing (B) is executed instead of the judgement processing (A) illustrated in FIG. 24.

Figure 52:
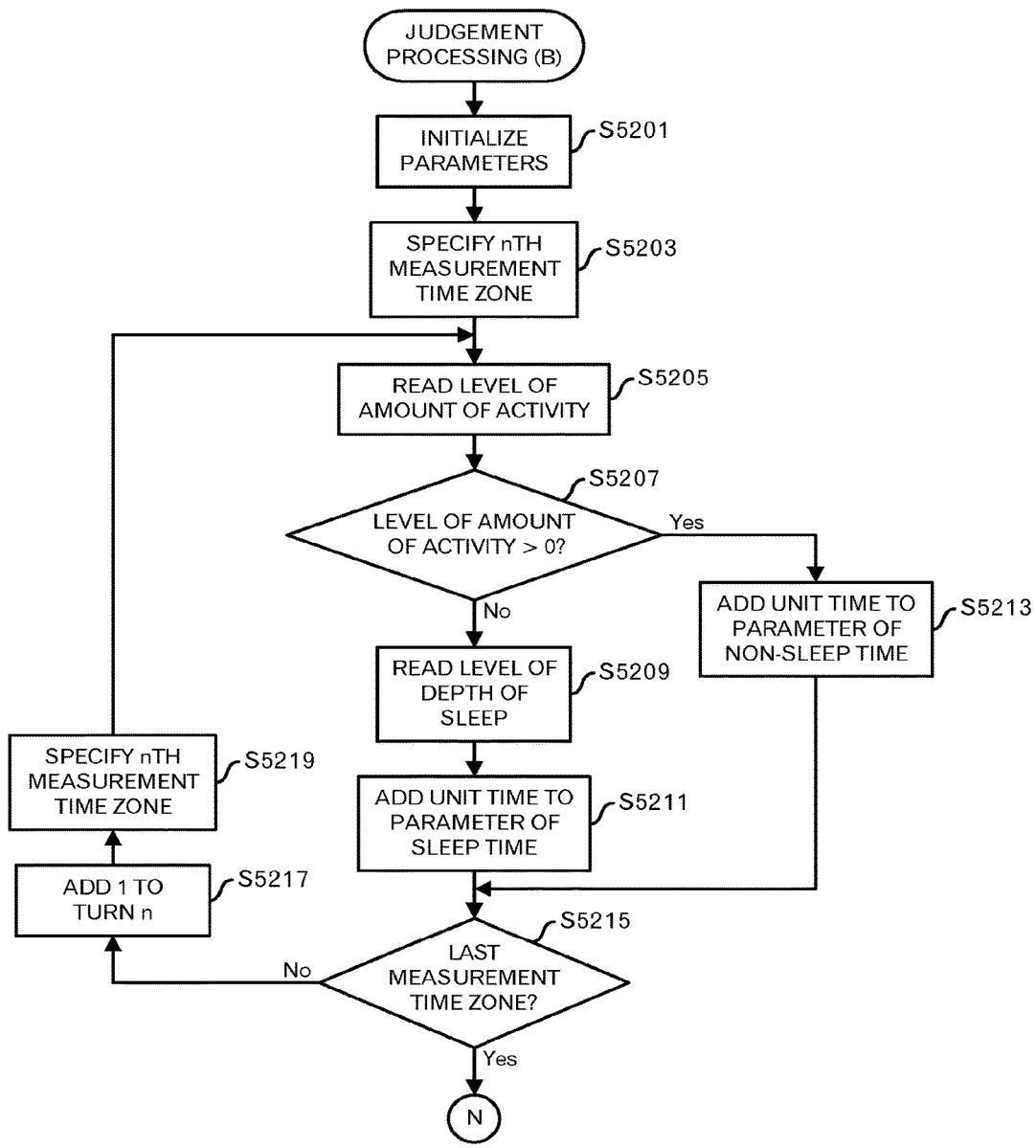
FIG. 52 is a diagram depicting an example of the judgement processing (B) flow.

FIG. 52 illustrates an example of a judgement processing (B) flow. In the judgement processing (B) as well, as in the judgement processing (A), the judgement unit 519 processes each measurement time zone that is included in the target period of the graph display in chronological order, and calculates the total of sleep time and the total of non-sleep time.

The judgement unit 519 initializes, as in S2401 in the judgement processing (A), parameters that are stored in the internal data storage unit 545 (S5201).

The judgement unit 519 specifies, as in S2403 in the judgement processing (A), a nth measurement time zone in the target period of the graph display (S5203).

The judgement unit 519 reads the level of the amount of activity that corresponds to the specified measurement time zone from the second data that is stored in the second data storage unit 533 (S5205).

The judgement unit 519 determines whether or not the level of the amount of activity is greater than 0 (S5207). When it is determined that the level of the amount of activity is not greater than 0, or in other words, when the level of the amount of activity is 0, the judgement unit 519 reads the level of the depth of sleep that corresponds to the specified measurement time zone from the first data that is stored in the first data storage unit 531 (S5209). The judgement unit 519 adds a unit time to the parameter of sleep time (S5211). The unit time corresponds to the length of a measurement time zone.

When it is determined that the level of the amount of activity is greater than 0, the judgement unit 519 adds a unit time to the parameter for non-sleep time (S5213). The unit time corresponds to the length of a measurement time zone.

The judgement unit 519 determines whether or not the processed measurement time zone corresponds to the end of the target period of the graph display (S5215). When it is determined that the processed measurement time zone does not correspond to the end of the target period of the graph display, the judgement unit 519 adds 1 to the parameter n that represents the turn (S5217). The judgement unit 519 specifies the nth measurement time zone (S5219). Then, processing returns to S5205, and the processing described above is repeated.

Figure 53:
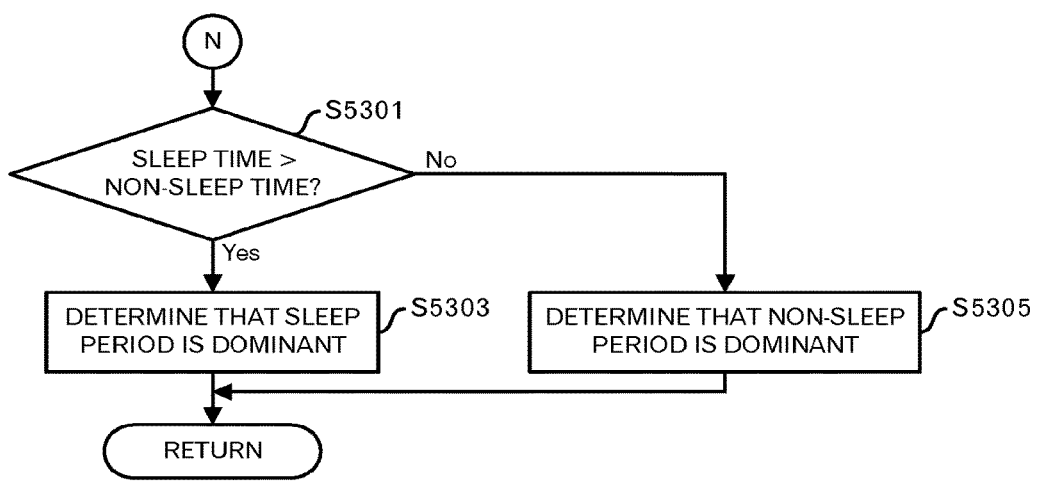
FIG. 53 is a diagram depicting an example of the judgement processing (B) flow.

When it is determined that the processed measurement time zone corresponds to the end of the target period of the graph display, the processing shifts to the processing of S5301 illustrated in FIG. 53 by way of the terminal N.

The explanation shifts to an explanation of FIG. 53. The judgement unit 519 determines, as in S2501 of the judgement processing (A) (FIG. 25), whether or not the value of the total of sleep time (value of the parameter for sleep time) is greater than the value of the total of non-sleep time (value of the parameter for non-sleep time) (S5301).

When it is determined that the value of the total of sleep time is greater than the value of the total of non-sleep time, the judgement unit 519 determines, as in S2503 in the judgement processing (A), that sleep period is dominant (S5303).

However, when it is determined that the value of the total of the sleep time is not greater than the value of the total of the non-sleep time, the judgement unit 519 determines, as in S2505 of the judgement processing (A), that the non-sleep period is dominant (S5305). When the judgement processing (B) ends, the processing shifts to the processing of S2303 illustrated in FIG. 23.

By this embodiment, the user is able to know the non-sleep state that is an awake state.

[Embodiment 3]

In this embodiment, an example will be explained in which the state of the vital activity of a subject for each day of a week is displayed on one screen.

Figure 54:
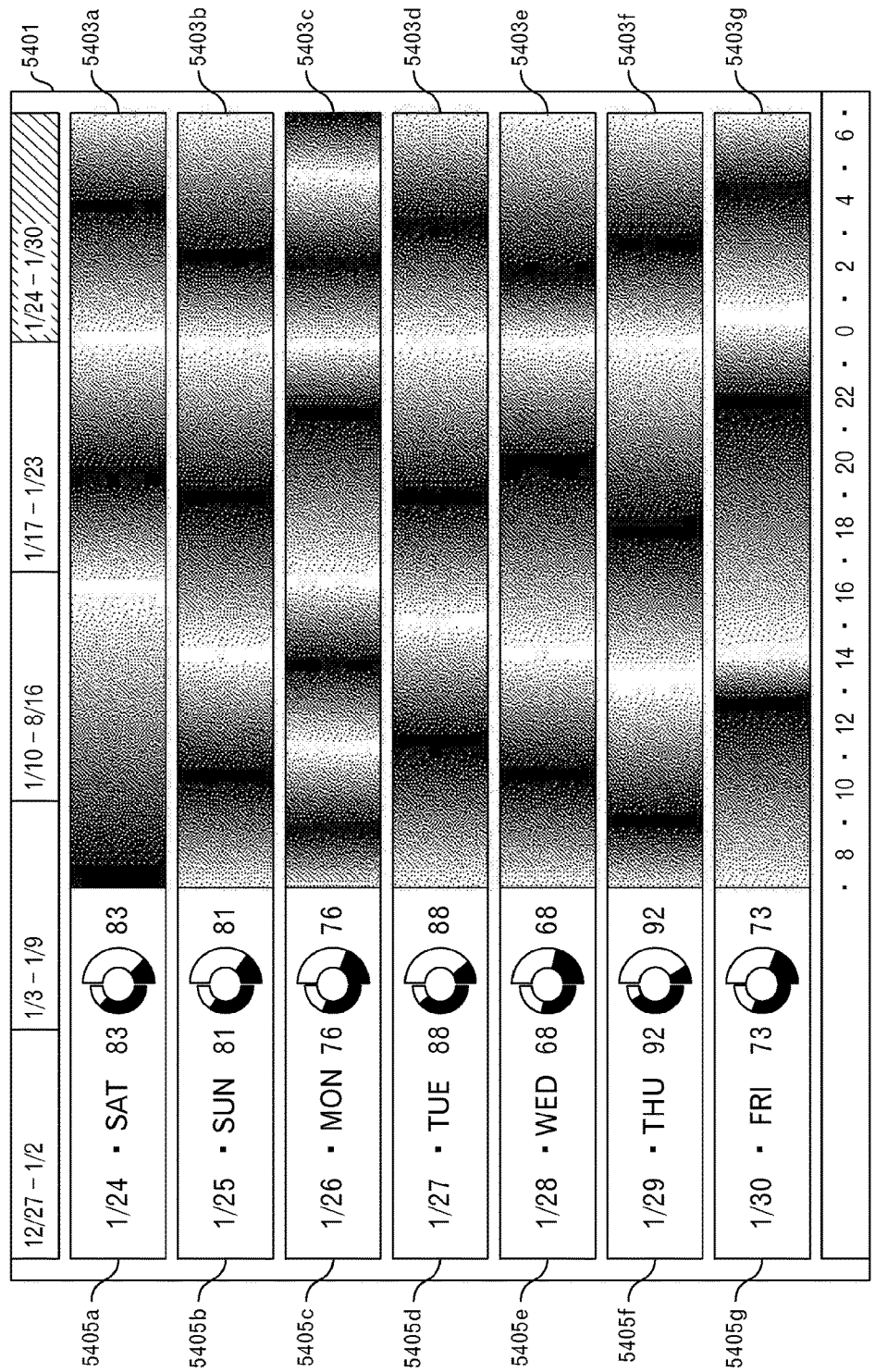
FIG. 54 is a diagram depicting an example of a weekly screen.

FIG. 54 illustrates an example of a week screen. In this example, the week screen 5401 illustrates the state of the vital activity for each day of a week. On the week screen 5401, a fourth area 5403 and a fifth area 5405 that correspond to each day are displayed. A heat map for one day is displayed in the fourth area 5403. The date, the activity index, and the sleep index are displayed in the fifth area 5405.

Figure 55:
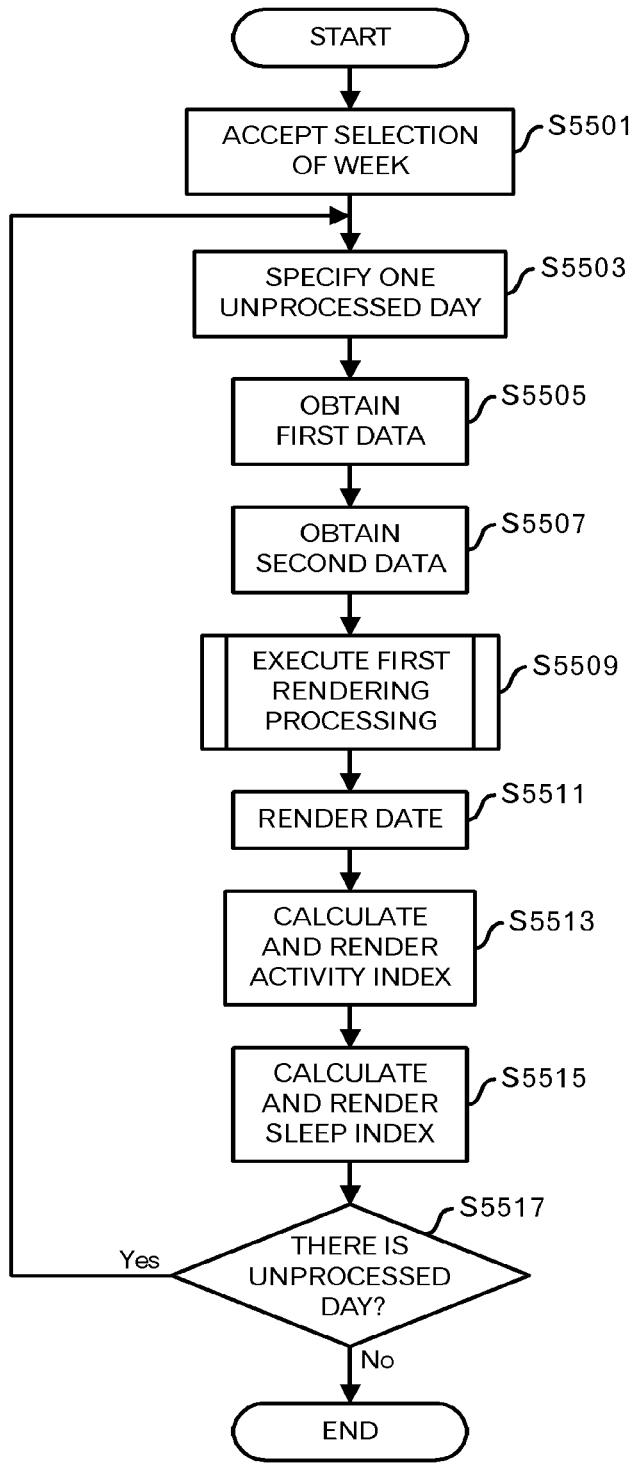
FIG. 55 is a diagram depicting an example of a display processing flow of the weekly screen.

FIG. 55 illustrates an example of a display processing flow for the week screen. The acceptance unit 501 accepts a week selection (S5501). The display processing unit 503 specifies one unprocessed day of the days included in the selected week (S5503). The first obtaining unit 513 obtains, as in the case of S1001 in FIG. 10, first data (S5505). The first obtaining unit 513 obtains, as in the case of S1003 in FIG. 10, second data (S5507).

The first rendering unit 515 executes first rendering processing (S5509). In the first rendering processing of the third embodiment, the first rendering unit 515 renders a graph image in the fourth area 5403 that corresponds to the day. Moreover, the displayed period is 24 hours. In other words, the entire second graph image 1103 is copied in the fourth area 5403.

The second rendering unit 521 renders the date of the day in the fifth area 5405 that corresponds to the day (S5511).

The second obtaining unit 523 obtains, as in the case of S2705 in FIG. 27, the activity index. Alternatively, the second rendering unit 521 calculates the activity index. The second rendering unit 521 renders the activity index in the fifth area 5405 that corresponds to the day (S5513).

The second obtaining unit 523 obtains, as in the case of S2603 in FIG. 26, the sleep index. Alternatively, the second rendering unit 521 calculates the sleep index. The second rendering unit 521 renders the sleep index in the fifth area 5405 that corresponds to the day (S5515).

The display processing unit 503 determines whether or not there is an unprocessed day (S5517). When it is determined that there is an unprocessed day, the processing returns to S5503, and the processing described above is repeated. When it is determined that there is no unprocessed day, the display processing for displaying the week screen ends.

By this embodiment, it is possible to display the state of the vital activity even for a comparatively long period. In other words, the state of the vital activity for one day is able to be displayed in a narrow vertical width, and it is possible to display data for plural days in the vertical direction. In the example in FIG. 54, an example was given in which the passage of time in one day is displayed in the horizontal direction of the screen, and the passage of days is displayed in the vertical direction, however, the display may be a display in which vertical and horizontal directions are interchanged.

Although the embodiments of this invention were explained above, this invention is not limited to those. For example, the aforementioned functional block configuration does not always correspond to actual program module configuration.

Moreover, the aforementioned configuration of each storage area is a mere example, and may be changed. Furthermore, as for the processing flow, as long as the processing results do not change, the turns of the steps may be exchanged or the steps may be executed in parallel.

Figure 56:
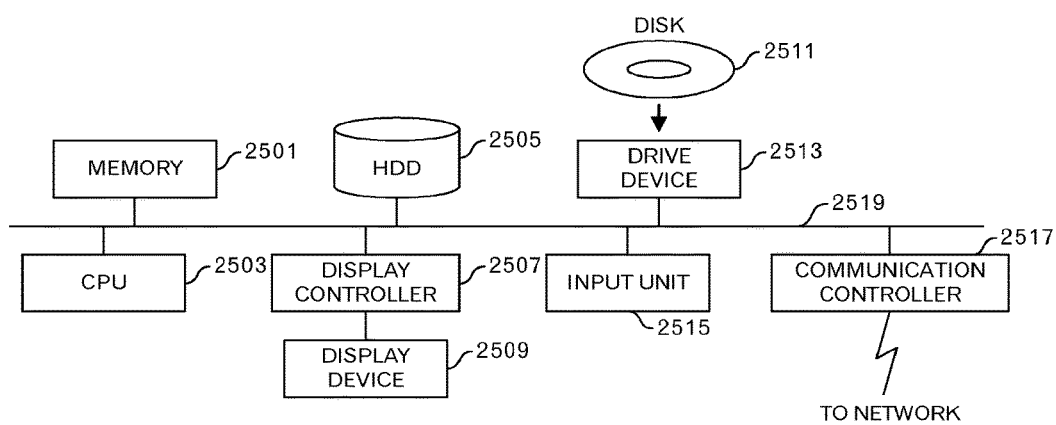
FIG. 56 is a functional block diagram of a computer.

In addition, the aforementioned display processing apparatus 101 is a computer apparatus as illustrated in FIG. 56. That is, a memory 2501, a CPU (central processing unit) 2503, a HDD (hard disk drive) 2505, a display controller 2507 connected to a display device 2509, a drive device 2513 for a removable disk 2511, an input unit 2515, and a communication controller 2517 for connection with a network are connected through a bus 2519 as illustrated in FIG. 56. An OS (operating system) and an application program for carrying out the foregoing processing in the embodiment, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform predetermined operations. Moreover, intermediate processing data is stored in the memory 2501, and if necessary, it is stored in the HDD 2505. In these embodiments of this invention, the application program to realize the aforementioned processing is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer apparatus as stated above, the hardware such as the CPU 2503 and the memory 2501, the OS and the application programs systematically cooperate with each other, so that various functions as described above in details are realized.

Figure 57:
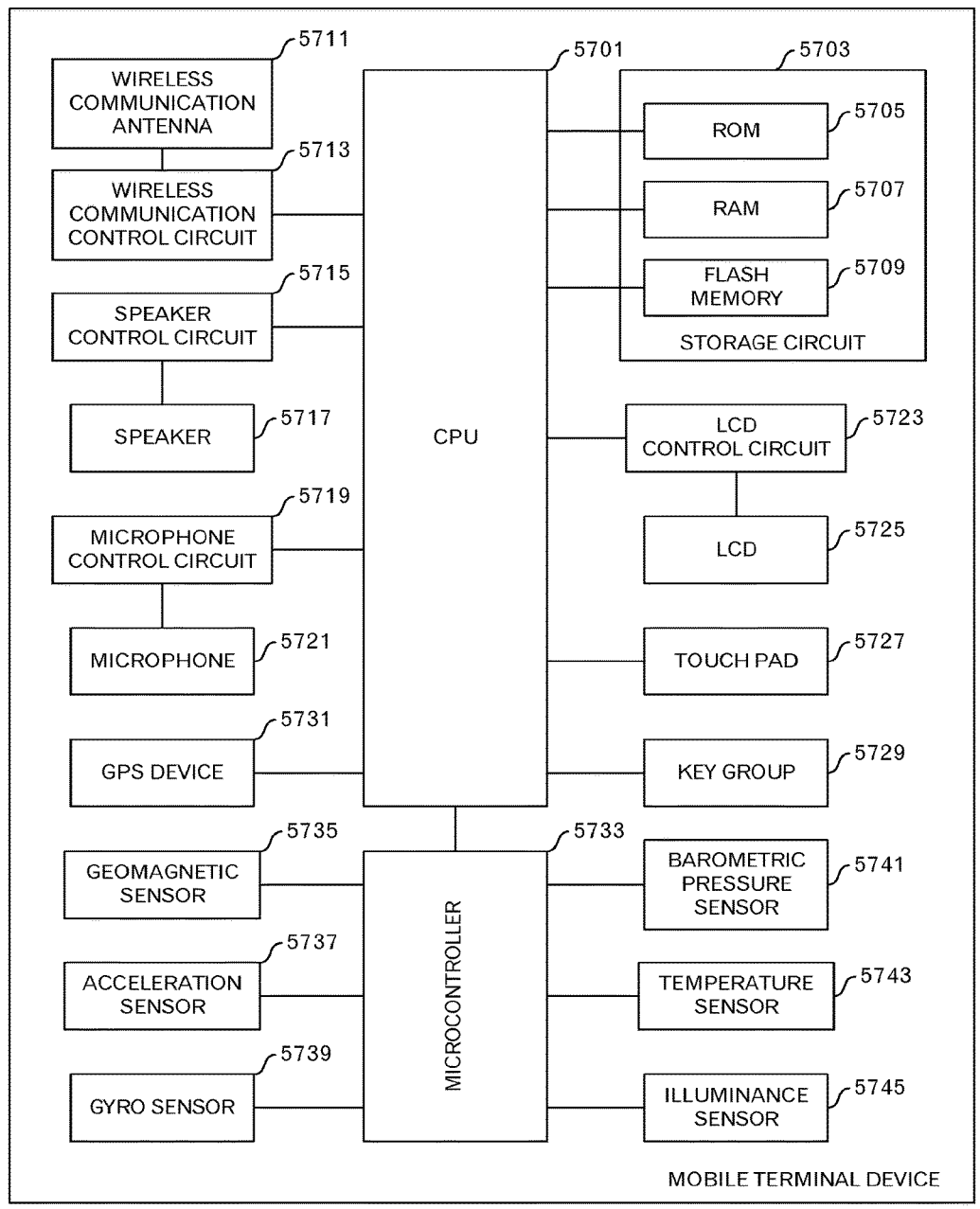
FIG. 57 is a diagram depicting an example of hardware configuration of a mobile terminal device.

Moreover, the display processing apparatus 101 described above may be a mobile terminal device. FIG. 57 illustrates an example of hardware configuration of a portable terminal device. A portable terminal device has a CPU (Central Processing Unit) 5701, a storage circuit 5703, a wireless communication antenna 5711, a wireless communication control circuit 5713, a speaker control circuit 5715, a speaker 5717, a microphone control circuit 5719, a microphone 5721, a LCD (Liquid Crystal Display) control circuit 5723, a LCD 5725, a touch pad 5727, a key group 5729, a GPS (Global Positioning System) device 5731, a microcontroller 5733, a geomagnetic sensor 5735, an acceleration sensor 5737, a gyro sensor 5739, a barometric pressure sensor 5741, a temperature sensor 5743 and an illuminance sensor 5745.

The CPU 5701 may also include a modem CPU and an application CPU. The storage circuit 5703 has, for example, a ROM (Read Only Memory) 5705, a RAM (Random Access Memory) 5707 and a flash memory 5709. The ROM 5705 stores, for example, a program and preset data for an operating system and the like. The RAM 5707 includes, for example, an area in which a program for an application or the like is expanded. The RAM 5707 also includes an area that temporarily stores data. The flash memory 5709 stores, for example, a program and data to be stored for an application and the like.

The LCD control circuit 5723 operates a clock circuit at a designated operating frequency, and drives an LCD 5725. The LCD 5725 displays a display screen. The touch pad 5727 is, for example, a panel-shaped sensor that is arranged on the display surface of the LCD 5725, and receives instructions by touch operation. More specifically, an integrated LCD 5725 and the touch pad 5727 are used as a touch panel. The hardware keys of the key group 5729 are all provided on part of the housing.

The wireless communication antenna 5711 receives, for example, radio waves according to the cellular communication format, the wireless LAN (Local Area Network) format, the short-range communication format and the like. The wireless communication control circuit 5713 performs control of wireless communication according to frequencies used by each communication format. By controlling wireless communication, audio communication for a phone call, or data communication via the Internet is performed.

The speaker control circuit 5715 performs digital/analog conversion related to audio data. The speaker 5717 outputs analog data as sound. The microphone control circuit 5719 performs analog/digital conversion related to audio data. The microphone 5721 converts sound to analog data.

The microcontroller 5733 is connected to the CPU 5701. The geomagnetic sensor 5735, the acceleration sensor 5737, the gyro sensor 5739, the barometric pressure sensor 5741, the temperature sensor 5743, and the illuminance sensor 5745 are connected to the microcontroller 5733. The microcontroller 5733 controls the geomagnetic sensor 5735, the acceleration sensor 5737, the gyro sensor 5739, the barometric pressure sensor 5741, the temperature sensor 5743, and the illuminance sensor 5745. The geomagnetic sensor 5735 measures a magnetic component that includes geomagnetism. The acceleration sensor 5737 measures acceleration. The gyro sensor 5739 detects an attitude of the portable terminal device. The barometric pressure sensor 5741 measures the atmospheric pressure. The temperature sensor 5743 measures the temperature. The illuminance sensor 5745 measures the illuminance.

The aforementioned embodiments are summarized as follows:

A state display method of one aspect includes: obtaining measurement results of vital activities of a subject; and displaying temporal transition of states of the subject by a one-dimensional heat map based on the measurement results. And the displaying includes: first displaying, in association with a first period in which the measurement results represent a sleep state, a first color that represents a depth of sleep by shading and has a first hue corresponding to the sleep state; and second displaying, in association with a second period in which the measurement results represent a non-sleep state, a second color that represents an intensity of an activity by the shading and has a second hue corresponding to the non-sleep state.

In this way, it enables a user to grasp chronologically a relation between a depth of sleep and an intensity of an activity, since the depth of sleep and the intensity of the activity are displayed as a series of states. Furthermore, in another aspect, it becomes possible to grasp sensuously a transition of states including switching of the sleep state and the non-sleep state, because the depth of sleep and the intensity of the activity are illustrated by shading of a color corresponding to each of the sleep state and the non-sleep state.

Furthermore, the displaying may further include third displaying, at a corresponding position, identification information for a time of at least one of moonrise, moonset, sunrise and sunset in a period displayed in the one-dimensional heat map.

In this way, it is helpful when considering an influence of movements of the sun and the moon on a vital activity. For example, it is helpful when considering an influence of sunlight on a vital activity, because it is possible to grasp a time zone during which the sun shines. Moreover, it is helpful when considering an influence of moonlight on a vital activity, because it is possible to grasp a time zone during which the moon shines.

Furthermore, the displaying may further include fourth displaying identification information for an age of a moon in a period displayed in the one-dimensional heat map.

In this way, it is helpful when considering an influence of the age of the moon on a vital activity.

Furthermore, the displaying may include fifth displaying change of outdoor temperature or indoor temperature around the subject in a period displayed in the one-dimensional heat map in a form in which a direction of an axis is different from a direction of a time axis in the one-dimensional heat map.

In this way, it is helpful when considering an influence of change of temperature on a vital activity.

Incidentally, it is possible to create a program causing a processor or a computer to execute the aforementioned processing, and such a program is stored in a computer readable storage medium or storage device such as a flexible disk, CD-ROM, DVD-ROM, magneto-optic disk, a semiconductor memory, and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:
1. A state display method, comprising:
obtaining, by using a computer, measurement results of vital activities of a subject; and
displaying, by using the computer, a temporal transition of states of the subject in a designated time period from a first time to a second time by a one-dimensional heat map based on the measurement results, and an analysis result obtained by analyzing the states of the subject in the designated time period from the first time to the second time, wherein the displaying comprises:

first displaying, in association with a first period in which the measurement results represent a sleep state, a first color that represents a depth of sleep by shading and has a first hue corresponding to the sleep state;

second displaying, in association with a second period in which the measurement results represent a non-sleep state, a second color that represents an intensity of an activity by the shading and has a second hue corresponding to the non-sleep state;

third displaying, upon detecting that a sleep section is longer than a non-sleep section in the designated time period from the first time to the second time, the analysis result regarding the sleep state of the subject; and fourth displaying, upon detecting that the non-sleep section is longer than the sleep section in the designated time period from the first time to the second time, the analysis result regarding the non-sleep state of the subject.

2. The state display method as set forth in claim 1, wherein the displaying further comprises displaying, at a corresponding position, identification information for a time of at least one of moonrise, moonset, sunrise and sunset in a period displayed in the one-dimensional heat map.

3. The state display method as set forth in claim 1, wherein the displaying further comprises displaying identification information for an age of a moon in a period displayed in the one-dimensional heat map.

4. The state display method as set forth in claim 1, wherein the displaying further comprises displaying a change of outdoor temperature or indoor temperature around the subject in a period displayed in the one-dimensional heat map in a form in which a direction of an axis is different from a direction of a time axis in the one -dimensional heat map.

5. A non-transitory computer-readable storage medium storing a program that causes a computer to execute a process, the process comprising;

obtaining measurement results of vital activities of a subject; and displaying a temporal transition of states of the subject in a designated time period from a first time to a second time by a one-dimensional heat map based on the measurement results, and an analysis result obtained by analyzing the states of the subject in the designated time period from the first time to the second time, wherein the displaying comprises:

first displaying, in association with a first period in which the measurement results represent a sleep state, a first color that represents a depth of sleep by shading and has a first hue corresponding to the sleep state;

second displaying, in association with a second period in which the measurement results represent a non-sleep state, a second color that represents an intensity of an activity by the shading and has a second hue corresponding to the non-sleep state;

third displaying, upon detecting that a sleep section is longer than a non-sleep section in the designated time period from the first time to the second time, the analysis result regarding the sleep state of the subject; and fourth displaying, upon detecting that the non-sleep section is longer than the sleep section in the designated time period from the first time to the second time, the analysis result regarding the non-sleep state of the subject.

6. A state display apparatus, comprising:

a memory; and a processor coupled to the memory and configured to:

obtain measurement results of vital activities of a subject; and display a temporal transition of states of the subject in a designated time period from a first time to a second time by a one-dimensional heat map based on the measurement results, and an analysis result obtained by analyzing the states of the subject in the designated time period from the first time to the second time, wherein to display the temporal transition of states of the subject and the analysis result, the processor is configured to:

first render, in association with a first period in which the measurement results represent a sleep state, a first color that represents a depth of sleep by shading and has a first hue corresponding to the sleep state;

second render, in association with a second period in which the measurement results represent a non-sleep state, a second color that represents an intensity of an activity by the shading and has a second hue corresponding to the non-sleep state;

third render, upon detecting that a sleep section is longer than a non-sleep section in the designated time period from the first time to the second time, the analysis result regarding the sleep state of the subject; and fourth render, upon detecting that the non-sleep section is longer than the sleep section in the designated time period from the first time to the second time, the analysis result regarding the non-sleep state of the subject.

* * * * *